(12) United States Patent
Kol et al.

(10) Patent No.: US 8,907,032 B2
(45) Date of Patent: Dec. 9, 2014

(54) SALALEN LIGANDS AND ORGANOMETALLIC COMPLEXES

(75) Inventors: Moshe Kol, Ramat Gan (IL);
Konstantin Press, Rishon-LeZion (IL);
Ad Cohen, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 13/805,011

(22) PCT Filed: Jun. 16, 2011

(86) PCT No.: PCT/IL2011/000482
§ 371 (c)(1),
(2), (4) Date: Dec. 18, 2012

(87) PCT Pub. No.: WO2011/158241
PCT Pub. Date: Dec. 22, 2011

(65) Prior Publication Data
US 2013/0096271 A1    Apr. 18, 2013

Related U.S. Application Data

(60) Provisional application No. 61/356,044, filed on Jun. 18, 2010.

(51) Int. Cl.
| | | |
|---|---|---|
| C08F 4/76 | (2006.01) |
| C07D 207/09 | (2006.01) |
| C07F 7/00 | (2006.01) |
| C07C 251/24 | (2006.01) |
| C07F 7/28 | (2006.01) |
| C08F 12/08 | (2006.01) |
| C08F 10/00 | (2006.01) |
| C07C 249/02 | (2006.01) |
| C08F 110/02 | (2006.01) |
| C08F 210/16 | (2006.01) |
| C08F 110/14 | (2006.01) |
| C08F 110/06 | (2006.01) |

(52) U.S. Cl.
CPC ........... *C07C 251/24* (2013.01); *C07C 2103/74* (2013.01); *C08F 110/02* (2013.01); *C08F 4/76* (2013.01); *C08F 210/16* (2013.01); *C08F 110/14* (2013.01); *C08F 110/06* (2013.01); *C07F 7/00* (2013.01); *C08F 12/08* (2013.01); *C07D 207/09* (2013.01); *C08F 10/00* (2013.01); *C07C 249/02* (2013.01); *C07F 7/28* (2013.01)
USPC ............. 526/172; 548/556; 548/403; 556/56; 564/274

(58) Field of Classification Search
None
See application file for complete search history.

(56) References Cited

U.S. PATENT DOCUMENTS

2009/0043100 A1 *   2/2009   Kondo et al. ................. 546/65

FOREIGN PATENT DOCUMENTS

| EP | 1849778 | 10/2007 |
| EP | 2003135 | 12/2008 |

(Continued)

OTHER PUBLICATIONS

International Search Report and the Written Opinion Dated Dec. 5, 2011 From the International Searching Authority Re. Application No. PCT/IL2011/000482.

(Continued)

*Primary Examiner* — Ling Choi
*Assistant Examiner* — Catherine S Branch

(57) ABSTRACT

Use of homogeneous catalytic systems which include as a pre-catalyst a complex of a Group IV metal and a salalen ligand in the polymerization of alpha-olefins, is disclosed. The alpha-olefin polymers obtained are characterized by controlled levels of tacticity. Also disclosed are novel salalen ligands and novel complexes thereof with Group IV metals.

41 Claims, 6 Drawing Sheets
(3 of 6 Drawing Sheet(s) Filed in Color)

(56) References Cited

FOREIGN PATENT DOCUMENTS

| JP | 2007-284438 | 11/2007 |
|---|---|---|
| WO | WO 2004/069881 | 8/2004 |
| WO | WO 2011/158241 | 12/2011 |

OTHER PUBLICATIONS

Berkessel et al. "A Practical and Versatile Access to Dihydrosalen (Salalen) Ligands: Highly Enantioselective Titanium in Situ Catalysts for Asymmetric Epoxidation With Aqueous Hydrogen Peroxide", Advanced Synthesis & Catalysis, XP002609532, 349: 2385-2391, Oct. 19, 2007.

Press et al. "Salalen Titanium Complexes in the Highly Isospecific Polymerization of 1-Hexene and Propylene", Angewandte Chemie, International Edition, XP009154260, 50(15): 3529-3532, Jan. 1, 2011.

Tshuva et al. "Isospecific Living Polymerization of 1-Hexene by a Readiliy Available Nonmetallocene C2-Symmetrical Zirconium Catalyst", Journal of the American Chemical SocietyXP002211306, 122: 10706-10707, Jan. 1, 2000.

Whitelaw et al. "Group 4 Salalen Complexes and Their Application for the Ring-Opening Polymerization of Rac-Lactide", Inorganic Chemistry, XP009154261, 49(15): 7176-7181, Jan. 1, 2010. p. 7177, Fig.1.

Yeori et al. "Salalen: A Hybrid Salan/Salen Tetradentate [ONNO]-Type Ligand and Its Coordination Behavior With Group IV Metals", Innorganic Chemistry Communications, XP003000296, 7: 280-282, Jan. 1, 2004. p. 281, Fig.2.

International Preliminary Report on Patentability Dated Jan. 3, 2013 From the International Bureau of WIPO Re. Application No. PCT/IL2011/000482.

Communication Pursuant to Article 94(3) EPC Dated Mar. 14, 2014 From the European Patent Office Re. Application No. 11736169.1.

* cited by examiner

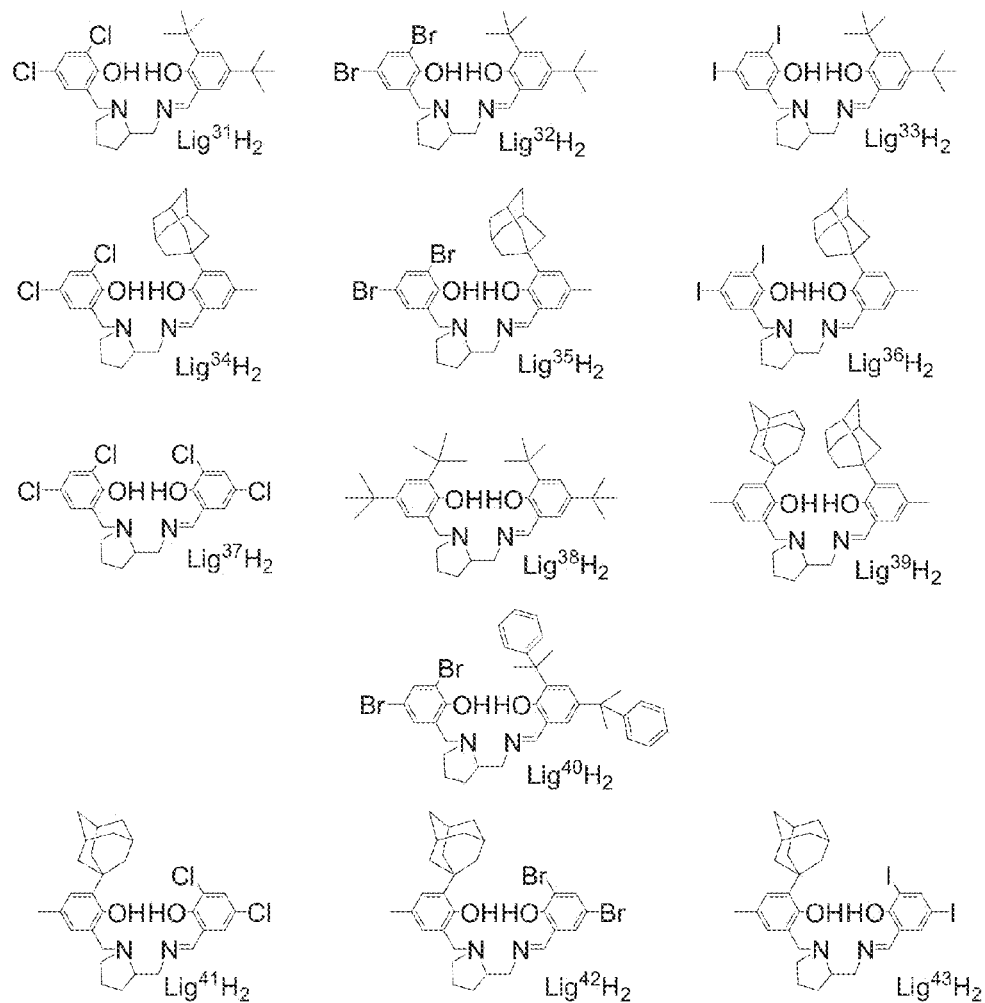
FIG. 6
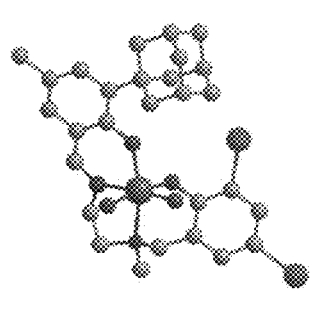
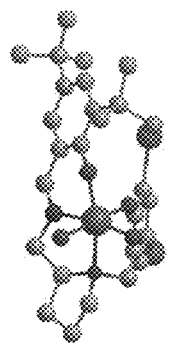
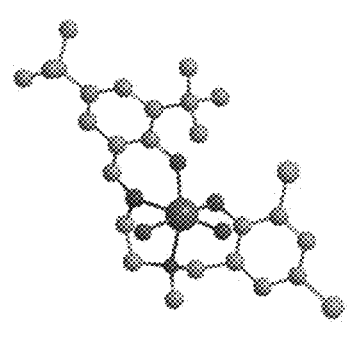
FIG. 7A      FIG. 7B      FIG. 7C

SALALEN LIGANDS AND ORGANOMETALLIC COMPLEXES

RELATED APPLICATIONS

This application is a National Phase of PCT Patent Application No. PCT/IL2011/000482 having International filing date of Jun. 16, 2011, which claims the benefit of priority under 35 USC §119(e) of U.S. Provisional Patent Application No. 61/356,044 filed on Jun. 18, 2010. The contents of the above applications are all incorporated by reference as if fully set forth herein in their entirety.

FIELD AND BACKGROUND OF THE INVENTION

The present invention, in some embodiments thereof, relates to chemistry and, more particularly, but not exclusively, to novel processes of tacticity-controlled olefin polymerization, to catalyst systems which comprise as a pre-catalyst novel complexes of Group IV metals which can be utilized in these processes, and to novel ligand precursors for preparing the pre-catalyst novel complexes.

The huge plastics industry produces a broad variety of polymeric materials having a broad range of properties. These plastic materials are derived from a small group of building blocks—monomers—including ethylene and propylene. The properties of the polymeric materials depend on the nature of these building blocks and on the process employed to assemble these building block. Most of these processes rely on catalytic polymerization.

The nature of the catalyst has a crucial role in determining the microstructure of the polymer, thus determining the physical properties of the resulting plastic. Molecular weight, molecular weight distribution, and above all, the type and degree of stereoregularity (tacticity) and regioregularity (head-to-tail enchainment) affect the properties of the resulting polymer. For example, three familiar forms of polypropylene are: isotactic, in which all methyl side groups are pointing in the same direction in the stretched chain; syndiotactic, in which the methyl side groups point at opposite directions alternatingly; and atactic, in which the methyl groups are pointing randomly in the two directions. A higher degree of stereoregularity (and regioregularity) leads to a better-defined polymer.

For example, isotactic polypropylene (iPP) is a thermoplastic material of vast importance and an ever-increasing demand derived from its useful physical properties and the availability of its feedstock—propylene. The most important microstructural property of polypropylene is the degree of isotacticity which, combined with sufficiently high molecular weight, determines its melting point ($T_m$) and thereby its possible applications. In an example, polypropylene having a very high degree of isotacticity has a melting transition of $T_m$=165° C. whereas an atactic polypropylene is a viscous oil.

The type and degree of tacticity are determined by the catalyst employed. Other properties determined by the catalyst include the polymer chain-lengths and chain-length distributions, backbone rearrangement, regio-regularity, ability to incorporate different monomers, etc. Successful catalysts need to be sufficiently active under industrially-relevant conditions.

Most of the industrial catalytic processes employed in ethylene and propylene polymerizations and copolymerizations rely on heterogeneous catalysis processes, and most of which, on heterogeneous Ziegler-Natta type catalysts. Ziegler-Natta catalysts, which are Group IV-metal compounds (and in particular titanium chloride adsorbed on magnesium chloride) activated with alkyl-aluminum co-catalysts, were invented in the 1950's. Ziegler-Natta catalysts of the current generation are highly active and enable the production of highly isotactic polypropylene (having a melting point of 165° C.). Yet, their heterogeneous nature leads to a broad molecular weight distribution ($PDI=M_w/M_n>3.5$), and to considerably lower activities towards higher olefins.

Homogeneous catalysts for olefin polymerization were developed in parallel. Most of these systems are based on Group IV transition metals (Ti, Zr, Hf) and feature cyclopentadienyl-type (Cp-type) rings as spectator ligands (groups that do not detach from the metal during the catalytic process). Systems that include two Cp-type rings are generally referred to as metallocenes, and systems that include a single Cp-type ring are referred to as half-metallocenes. Using Cp-type containing systems requires different co-catalysts for their activation, which include MAO (methyl aluminoxane) or various boron-based activators (often combined with aluminum based quenchers). When MAO is employed as a co-catalyst, it is usually taken in large excess relative to the pre-catalyst, with a typical ratio ranging from 1000:1 to 10000:1 MAO:pre-catalyst.

Metallocenes were investigated very intensively during the past three decades and have been the subject of numerous publications describing various structural modifications and their applications in propylene and other olefin polymerizations. Correlations between the symmetries of the catalysts and the tacticities of the resulting polymers were established (Ewen Rules). Yet, the commercial applications of the metallocenes are limited due to their high cost and oftentimes by an inferior isotacticity obtained for the resulting polypropylene.

In the past 15 years, there has been a worldwide interest in development of "cyclopentadienyl-free systems"—homogeneous pre-catalysts devoid of a cyclopentadienyl ring. This interest was driven by the over-crowdedness of the metallocene area, and by the realization that modified catalysts leading to polymers of new or improved properties could be developed. These non-metallocene systems include variable transition metals, and still, the most promising systems in terms of activities and stereospecificities are based on the Group IV transition metals. Some of these catalysts have shown remarkable activities, including living polymerization of high olefins at room temperature, highly active polymerization of ethylene, and the combination of living and isospecific polymerization of high olefins.

Octahedral complexes of Group IV metals have proven to be valuable catalysts for stereoregular olefin polymerization [Lamberti et al., C. *Coord. Chem. Rev.* 2009, 253, 2082]. In particular, $C_2$-symmetric catalysts of "sequential" tetradentate-dianionic ligands featuring the {ONNO}, {OOOO}, and {OSSO} cores were found to lead to isoselective polymerization of high-olefins and propylene [see, for example, Tshuva et al. *J. Am. Chem. Soc.* 2000, 122, 10706; Segal et al. *Organometallics*, 2005, 24, 200; Gendler et al. *J. Am. Chem. Soc.* 2008, 130, 2144; Cohen et al. *Macromolecules*, 2010, 43, 1689; Busico et al. *Proc. Natl. Acad. Sci. U.S.A.* 2006, 103, 15321; U.S. Pat. No. 7,241,714; Kiesewetter et al. *J. Am. Chem. Soc.* 2010, 132, 5566; Cohen et al. *Inorg. Chem.* 2007, 46, 8114; Ishii et al. *J. Am. Chem. Soc.* 2009, 131, 13566; and Capacchione et al. *J. Am. Chem. Soc.* 2003, 125, 4964].

Yet, the structural diversity of symmetric ligands is limited. The much broader variety of non-symmetric ligands should yield $C_1$-symmetric polymerization catalysts of superior performance.

For example, a family of catalysts recently developed by the Symyx company and found commercial application by the Dow company includes $C_1$-symmetric hafnium complexes having pyridyl-amido-type ligands (Boussie et al. *Angew. Chem. Int. Ed.* 2006, 45, 3278.). These catalysts polymerized propylene to a high-molecular weight polypropylene. Notably, the highest melting point described for these polymers was $T_m$ of approximately 150° C.

Thus, except for scarce cases, the tacticity induction in propylene polymerization by non-metallocenes is inferior in comparison to the best metallocenes and to the latest generation of heterogeneous Ziegler-Natta catalysts.

Salalen ligands are "sequential" tetradentate-dianionic ligands that include a neutral imine-donor, a neutral amine-donor, and two anionic phenolate groups. Salalen ligands may be regarded as half-Salan/half-Salen hybrid ligands. The coordination behavior of Salalen ligands was found to reflect that of its symmetric predecessors.

A preliminary report described a Salalen ligand featuring tert-butyl substituents on the two phenolate rings. This Salalen ligand was found to wrap around octahedral Group IV metal centers diastreoselectively so that the half-Salan O—N—N donors bound in a fac-mode and the half-Salen O—N—N donors bound in a mer-mode, yielding $C_1$-symmetric complexes with cis-related labile groups. The two labile groups experience different steric and electronic influence, as one of them is trans to the imine neutral N-donor while the other is trans to the phenolate ring O-donor (being proximal to the amine donor). Complexes of Salalen ligands were later reported to catalyze various transformations including asymmetric oxidations, and epoxide-$CO_2$ polymerization, but were never employed in olefin polymerization catalysis.

Exemplary additional publications include the following: Saito and Katsuki, Angew. Chem. Int. Ed., 2005, 44, 4600-4602; Shitama and Katsuki, Angew. Chem. Int. Ed., 2008, 47, 2450-2453; Yamaguchi et al., Angew. Chem. Int. Ed., 2007, 46, 4729-4731; Condo et al., Angew. Chem. Int. Ed., 2008, 47, 10195-10198; Suyama et al., Angew. Chem. Int. Ed., 2010, 49, 797-799; Berkessel et al., Adv. Synth. Catal., 2007, 349, 2385-2391; Berkessel et al., Adv. Synth. Catal., 2008, 350, 1287-1294; Matsumoto et al., Chem. Aaian J., 2008, 3, 351-358; Matsumoto et al., Chem. Comm., 2007, 3619-3627; Fujita et al, Chem. Lett., 2007, 36(9), 1092-1093; Takaki et al., Chem. Lett., 2008, 37(5), 502-503; Eno et al., Chem. Lett., 2008, 37(6), 632-633; Du et al., Inorg. Chim. Acta, 2008, 361, 3184-3192; Zeigler et al., Inorg. Chem., 2008, 48, 11290-11296; Kol et al., Inorg. Chem. Comm., 2004, 7, 280-282; Berkessel et al., J. Mol. Catal., 1996, 113, 321-342; Berkessel et al., J. Mol. Catal., 1997, 117, 339-346; Saito et al., J. Am. Chem. Soc., 2007, 129, 1978-1986; Xiong et al., Terahedon: Assymetry, 2010, 21, 374-378; Nakano et al., Macromolecules, 2009, 42, 6972-6980; and U.S. patent application having Publication Nos. 2009/0099381 and 2010/00081808.

SUMMARY OF THE INVENTION

There is a constant need to develop new catalytic systems for polymerizations of olefins such as ethylene, propylene, and higher olefins, as well as their copolymers, since these catalysts have substantial effect on the efficiency of the polymerization process and on the properties of the produced plastic materials.

Herein, the design and preparation of a novel family of non-metallocene catalysts for polymerization of alpha-olefins based on Group IV metal complexes (titanium, zirconium and hafnium) of "Salalen"-type ligands, is described.

Thus, a variety of Salalen ligand precursors (Salalen-$H_2$), and their metal complexes of the type [(Salalen)MXp] wherein M is a Group IV metal, X is a labile group and p is integer of 0 to 2, which can serve as pre-catalysts, are provided herein. These pre-catalysts, when activated in the presence of a co-catalyst, yield poly(alpha-olefin) polymers or copolymers when contacted with alpha-olefin(s), while enabling tuning of the polymer's or copolymer's properties by selecting the appropriate [(Salalen)MXp]-type complex.

In some embodiments, polymerization of propylene using pre-catalysts as described herein leads to highly isotactic polypropylene having high molecular weights and correspondingly very high melting points, that are among highest ever reported (e.g., $T_m$>168° C.).

Accordingly, according to an aspect of embodiments of the present invention there is provided a process of preparing a polypropylene having a melting transition temperature higher than 165° C.

In some embodiments, pre-catalysts as described herein, possessing different substituents lead to the provision of alpha-olefin polymers with various tacticities, controlled by the nature of the substituents.

According to an aspect of some embodiments of the present invention there is provided a process of polymerizing an alpha-olefin, the process comprising:

contacting the alpha-olefin with a catalyst system which comprises:

(i) a pre-catalyst comprising a Group IV metal atom and a Salalen ligand complexed therewith; and (ii) a co-catalyst, thereby producing a polymer of the alpha-olefin.

According to some embodiments of the present invention, the catalyst system comprises a pre-catalyst having the general Formula II:

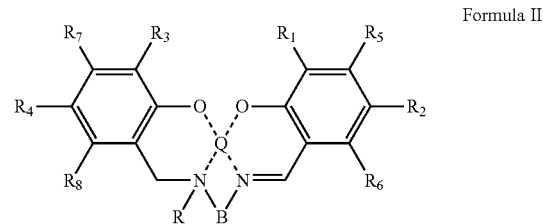

Formula II wherein:

Q is MXp, whereas M is a group IV element; X is a labile group; and p is an integer ranging from 0 to 4;

B is a bridging moiety being at least 2 carbon atoms in length;

R is hydrogen, alkyl, cycloalkyl, aryl, heteroaryl and heteroalicyclic, or, alternatively, forms a 5-membered or 6-membered cyclic or heterocyclic ring with a carbon atom of the bridging moiety; and $R_1$-$R_8$ are each independently selected from the group consisting of hydrogen, alkyl, cycloalkyl, aryl, halogen, alkoxy, aryloxy, heteroalicyclic, heteroaryl, and nitro, provided that at least one of $R_1$-$R_4$ is other than hydrogen.

According to some embodiments of the present invention, the alpha-olefin is selected from the group consisting of ethylene, propylene, 1-butene, 1-pentene, 4-methyl-1-pentene, 1-hexene, vinyl-cyclohexane, styrene, and any mixture thereof.

According to some embodiments of the present invention, the alpha-olefin is selected from the group consisting of ethylene, propylene, 1-hexene, styrene, and any mixture thereof.

According to some embodiments of the present invention, the alpha-olefin is propylene.

According to some embodiments of the present invention, the co-catalyst is selected from the group consisting of an aluminoxane, a boron Lewis acid, a boron salt and any mixture thereof.

According to some embodiments of the present invention, the co-catalyst is methylaluminoxane.

According to some embodiments of the present invention, the polymer of the alpha-olefin is characterized by an isotacticity degree of at least 50%.

According to some embodiments of the present invention, the isotacticity degree is higher than 70%.

According to some embodiments of the present invention, the isotacticity degree is higher than 90%.

According to some embodiments of the present invention, the isotacticity degree is higher than 99%.

According to some embodiments of the present invention, the polymer of the alpha-olefin is characterized by a molecular weight of at least $M_w = 200,000$ grams/mol.

According to some embodiments of the present invention, the polymer of the alpha-olefin is characterized by a molecular weight of at least $M_w = 400,000$ grams/mol.

According to some embodiments of the present invention, the polymer of the alpha-olefin is characterized by a molecular weight distribution (PDI) lower than 3.

According to some embodiments of the present invention, the polymer of the propylene is characterized by a melting transition temperature of at least 150° C.

According to some embodiments of the present invention, the polymer of the propylene is characterized by a transition temperature of at least 160° C.

According to some embodiments of the present invention, $R_5$-$R_8$ are each hydrogen.

According to some embodiments of the present invention, the bridging moiety has a general Formula IVA or IVB:

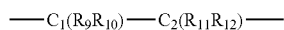

Formula IVA

—$C_1(R_9R_{10})$—$C_2(R_{11}R_{12})$—

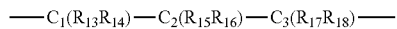

Formula IVB

—$C_1(R_{13}R_{14})$—$C_2(R_{15}R_{16})$—$C_3(R_{17}R_{18})$— wherein $R_9$-$R_{14}$, $R_{17}$ and $R_{18}$ are each independently selected from the group consisting of hydrogen, alkyl, cycloalkyl, aryl, heteroaryl and heteroalicyclic, $R_{15}$ and $R_{16}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of R and $R_9$-$R_{12}$ in Formula IVA or at least two of R and $R_{13}$-$R_{18}$ in Formula IVB form a 5-membered or 6-membered cyclic or heterocyclic ring.

According to some embodiments of the present invention, the bridging moiety has the general Formula IVA.

According to some embodiments of the present invention, each of $R_9$-$R_{12}$ is hydrogen.

According to some embodiments of the present invention, $R_9$ and R form the heterocyclic ring.

According to some embodiments of the present invention, the bridging moiety has the general Formula IVB.

According to some embodiments of the present invention, each of $R_{13}$-$R_{18}$ is hydrogen.

According to some embodiments of the present invention, at least two of $R_{13}$-$R_{18}$ form the cyclic ring.

According to some embodiments of the present invention, $R_{15}$-$R_{18}$ form together an aryl.

According to some embodiments of the present invention, R is alkyl.

According to some embodiments of the present invention, the alkyl is methyl.

According to some embodiments of the present invention, the alkyl is selected from the group consisting of alkaryl, ethyl and isopropyl.

According to some embodiments of the present invention, at least one of $R_1$-$R_4$ is an alkyl.

According to some embodiments of the present invention, each of $R_1$-$R_4$ is an alkyl.

According to some embodiments of the present invention, at least one of $R_1$ and $R_2$ is an alkyl.

According to some embodiments of the present invention, at least one of $R_3$ and $R_4$ is an alkyl.

According to some embodiments of the present invention, each of $R_1$ and $R_2$ is an alkyl.

According to some embodiments of the present invention, each of $R_3$ and $R_4$ is an alkyl.

According to some embodiments of the present invention, the alkyl is a bulky alkyl selected from the group consisting of tert-butyl, isobutyl, isopropyl, trityl, cumyl and tert-hexyl.

According to some embodiments of the present invention, at least one of $R_1$-$R_4$ is halogen.

According to some embodiments of the present invention, each of $R_1$-$R_4$ is halogen.

According to some embodiments of the present invention, at least one of $R_3$ and $R_4$ is halogen.

According to some embodiments of the present invention, each of $R_3$ and $R_4$ is halogen.

According to some embodiments of the present invention, at least one of $R_1$-$R_4$ is a bulky rigid group.

According to some embodiments of the present invention, the bulky rigid group is selected from the group consisting of aryl, heteroaryl, cycloalkyl and heteroalicyclic.

According to some embodiments of the present invention, at least one of $R_1$-$R_4$ is selected from the group consisting of aryl, heteroaryl, cycloalkyl and heteroalicyclic, each having at least 7 carbon atoms.

According to some embodiments of the present invention, $R_1$ is adamantyl.

According to an aspect of some embodiments of the present invention there is provided a polymer of an alpha-olefin, prepared by the process as described herein.

According to some embodiments of the present invention, the polymer is characterized by an isotacticity degree of at least 50%.

According to some embodiments of the present invention, the isotacticity degree is higher than 70%.

According to some embodiments of the present invention, the isotacticity degree is higher than 90%.

According to some embodiments of the present invention, the isotacticity degree is higher than 99%.

According to some embodiments of the present invention, the polymer is characterized by a molecular weight of at least $M_w = 200,000$ grams/mol.

According to some embodiments of the present invention, the polymer is characterized by a molecular weight of at least $M_w = 400,000$ grams/mol.

According to some embodiments of the present invention, the polymer is characterized by a molecular weight distribution (PDI) lower than 3.

According to some embodiments of the present invention, the alpha-olefin is propylene.

According to some embodiments of the present invention, the polymer is a polypropylene characterized by a melting transition temperature of at least 160° C.

According to some embodiments of the present invention, the melting transition temperature is at least 168° C.

According to an aspect of some embodiments of the present invention there is provided a process of preparing a polypropylene characterized by a melting transition temperature of at least 165° C., the process comprising polymerizing propylene in the presence of a catalyst system that comprises a ligand-metal complex.

According to some embodiments of the present invention, the polypropylene is characterized by a melting transition temperature of at least 168° C.

According to some embodiments of the present invention, the polypropylene is characterized by a molecular weight distribution (PDI) lower than 3.

According to some embodiments of the present invention, the catalyst system is a homogeneous catalyst system.

According to some embodiments of the present invention, the metal-ligand complex comprises a Group IV metal and a Salalen ligand complexed therewith.

According to an aspect of some embodiments of the present invention there is provided a polypropylene characterized by a melting transition temperature of at least 165° C., prepared by the process as described herein.

According to an aspect of some embodiments of the present invention there is provided a polypropylene characterized by a melting transition temperature of at least 168° C., and by a PDI lower than 3 (e.g., a PDI of about 2 or lower).

According to an aspect of some embodiments of the present invention there is provided a metal complex having the general formula II*:

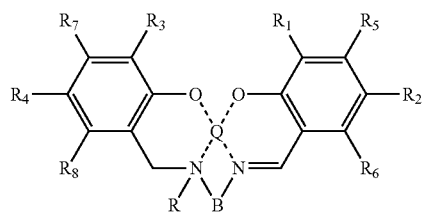

Formula II* wherein:

Q is MXp, whereas M is a group IV element; X is a labile group; and p is an integer ranging from 0 to 4;

B is a bridging moiety being at least 2 carbon atoms in length;

R is hydrogen, alkyl, cycloalkyl, aryl, heteroaryl and heteroalicyclic, or, alternatively, forms a 5-membered or 6-membered heterocyclic ring with a carbon atom of the bridging moiety; and $R_1$-$R_8$ are each independently selected from the group consisting of hydrogen, alkyl, cycloalkyl, aryl, halogen, alkoxy, aryloxy, heteroalicyclic, heteroaryl, and nitro, provided that:

(i) at least one of $R_1$-$R_4$ is independently a rigid bulky group;

(ii) each of $R_1$-$R_4$ is independently a halogen; and/or (iii) the R forms a 5-membered or 6-membered heterocyclic ring with a carbon atom of the bridging moiety.

According to an aspect of some embodiments of the present invention there is provided a compound having the general Formula I*:

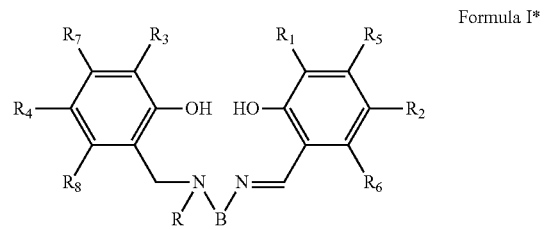

Formula I* wherein:

B is a bridging moiety being at least 2 carbon atoms in length;

R is hydrogen, alkyl, cycloalkyl, aryl, heteroaryl and heteroalicyclic, or, alternatively, forms a 5-membered or 6-membered heterocyclic ring with a carbon atom of the bridging moiety; and $R_1$-$R_8$ are each independently selected from the group consisting of hydrogen, alkyl, cycloalkyl, aryl, halogen, alkoxy, aryloxy, heteroalicyclic, heteroaryl, and nitro, provided that:

(i) at least one of $R_1$-$R_4$ is independently a rigid bulky group;

(ii) each of $R_1$-$R_4$ is independently a halogen; and/or (iii) the R forms a 5-membered or 6-membered heterocyclic ring with a carbon atom of the bridging moiety.

According to some embodiments of the present invention, $R_5$-$R_8$ are each hydrogen.

According to some embodiments of the present invention, the bridging moiety has a general Formula IVA or IVB:

 Formula IVA

 Formula IVB wherein $R_9$-$R_{14}$, $R_{17}$ and $R_{18}$ are each independently selected from the group consisting of hydrogen, alkyl, cycloalkyl, aryl, heteroaryl and heteroalicyclic, $R_{15}$ and $R_{16}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of R and $R_9$-$R_{12}$ in Formula IVA or at least two of R and $R_{13}$-$R_{18}$ in Formula IVB form a 5-membered or 6-membered cyclic or heterocyclic ring.

According to some embodiments of the present invention, the bridging moiety has the general Formula IVA.

According to some embodiments of the present invention, each of $R_9$-$R_{12}$ is hydrogen.

According to some embodiments of the present invention, $R_9$ and R form the heterocyclic ring.

According to some embodiments of the present invention, the bridging moiety has the general Formula IVB.

According to some embodiments of the present invention, each of $R_{13}$-$R_{18}$ is hydrogen.

According to some embodiments of the present invention, at least two of $R_{13}$-$R_{18}$ form the cyclic ring.

According to some embodiments of the present invention, $R_{15}$-$R_{18}$ form together an aryl.

According to some embodiments of the present invention, R is alkyl.

According to some embodiments of the present invention, the alkyl is methyl.

According to some embodiments of the present invention, the alkyl is selected from the group consisting of alkaryl, ethyl and isopropyl.

According to some embodiments of the present invention, the bulky rigid group is selected from the group consisting of a cycloalkyl and a heteroalicyclic, each having at least 7 carbon atoms.

According to some embodiments of the present invention, $R_1$ is the bulky rigid group.

According to some embodiments of the present invention, at least one of $R_1$ and $R_3$ is the bulky rigid group.

According to some embodiments of the present invention, the bulky rigid group is adamantyl.

According to an aspect of some embodiments of the present invention there is provided a process of preparing a salalen ligand having the general Formula I, as described herein, the process being effected as described hereinafter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
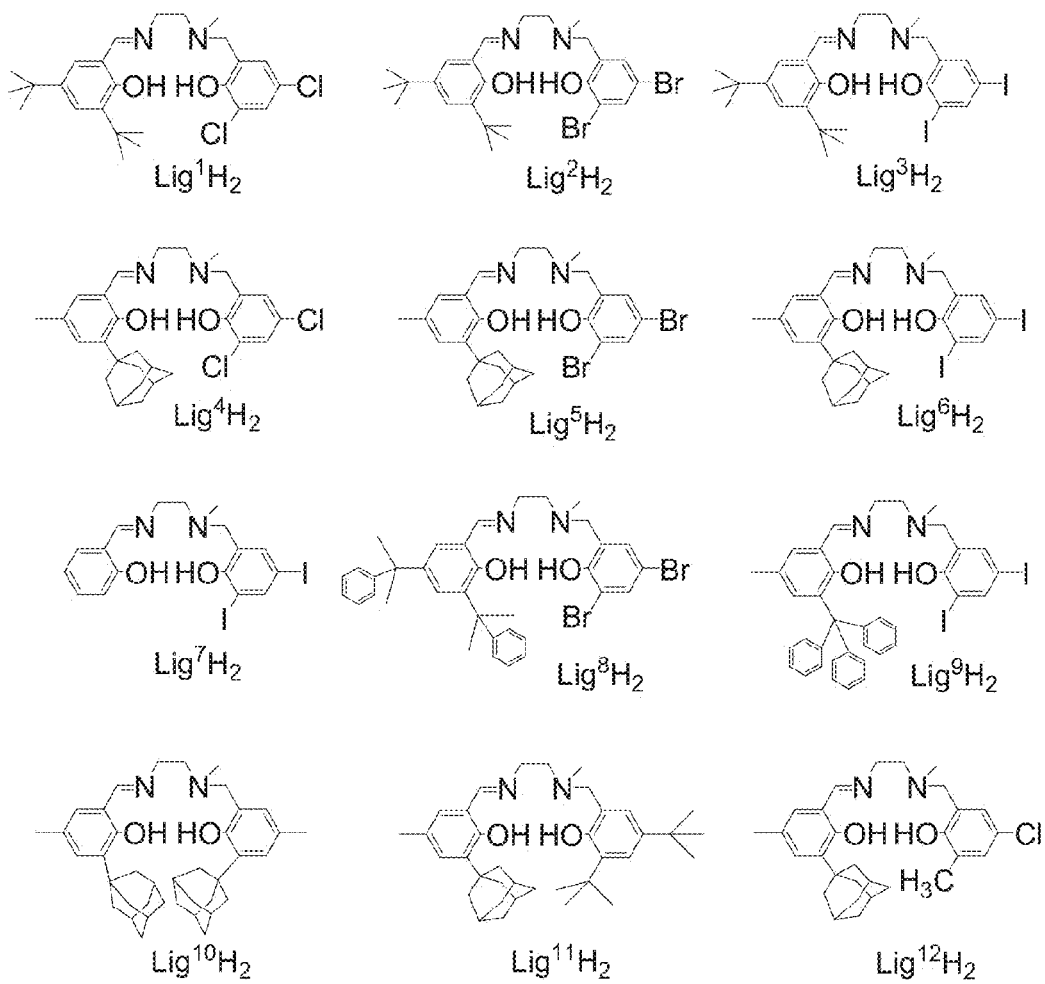
Figure 2:
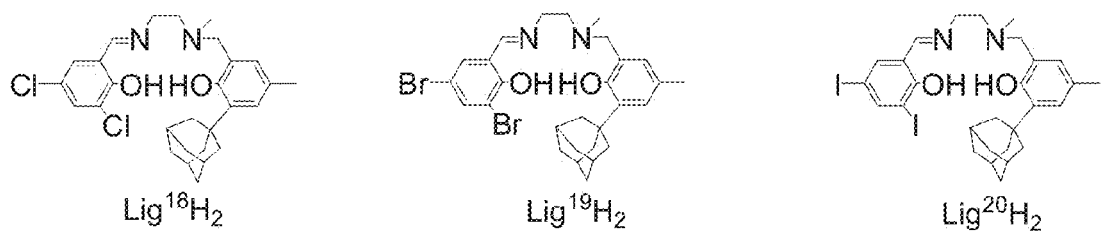
Figure 3:
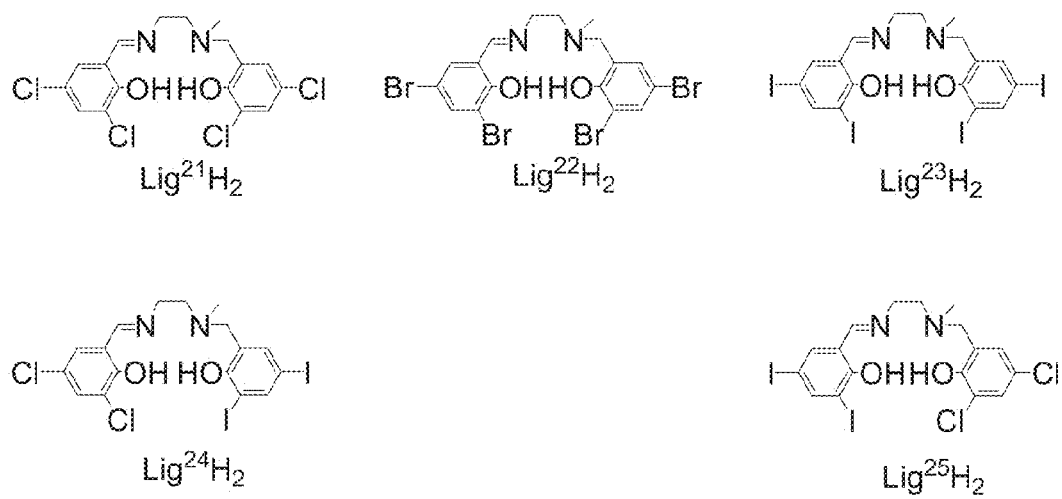
Figure 4:
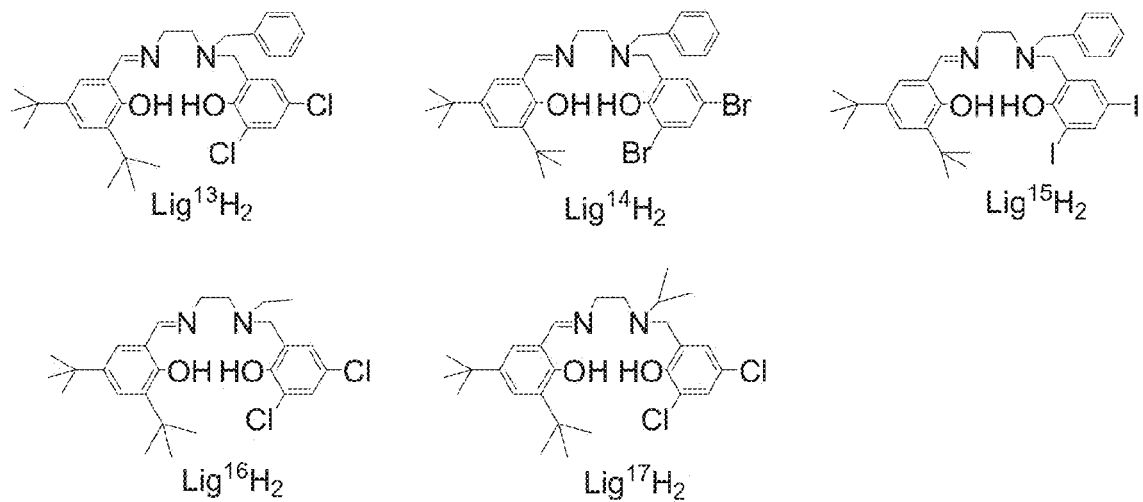
Figure 5:
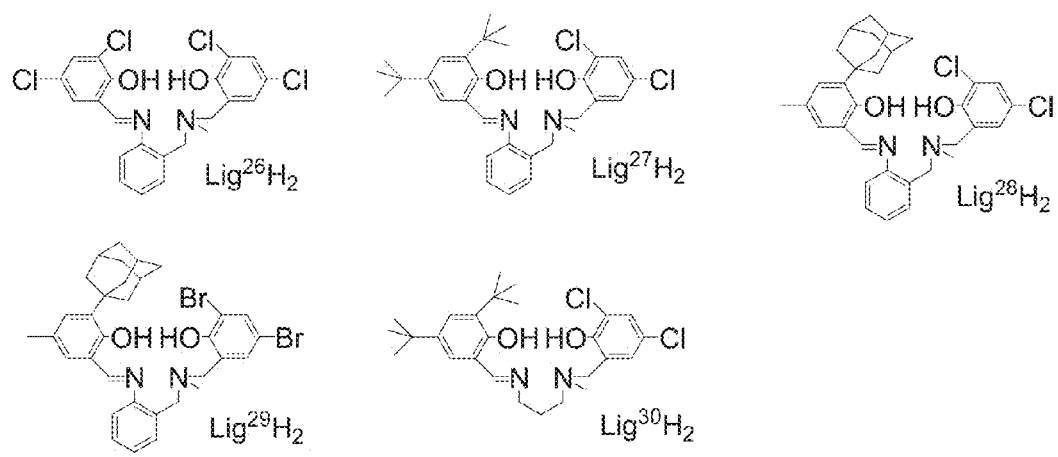
Figure 8A:
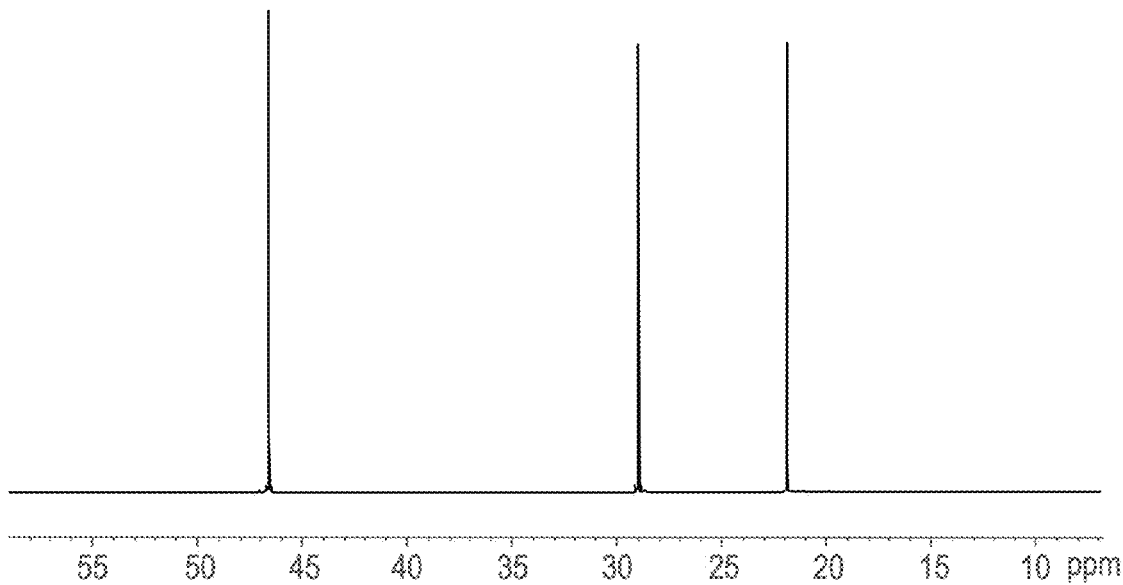
Figure 8B:
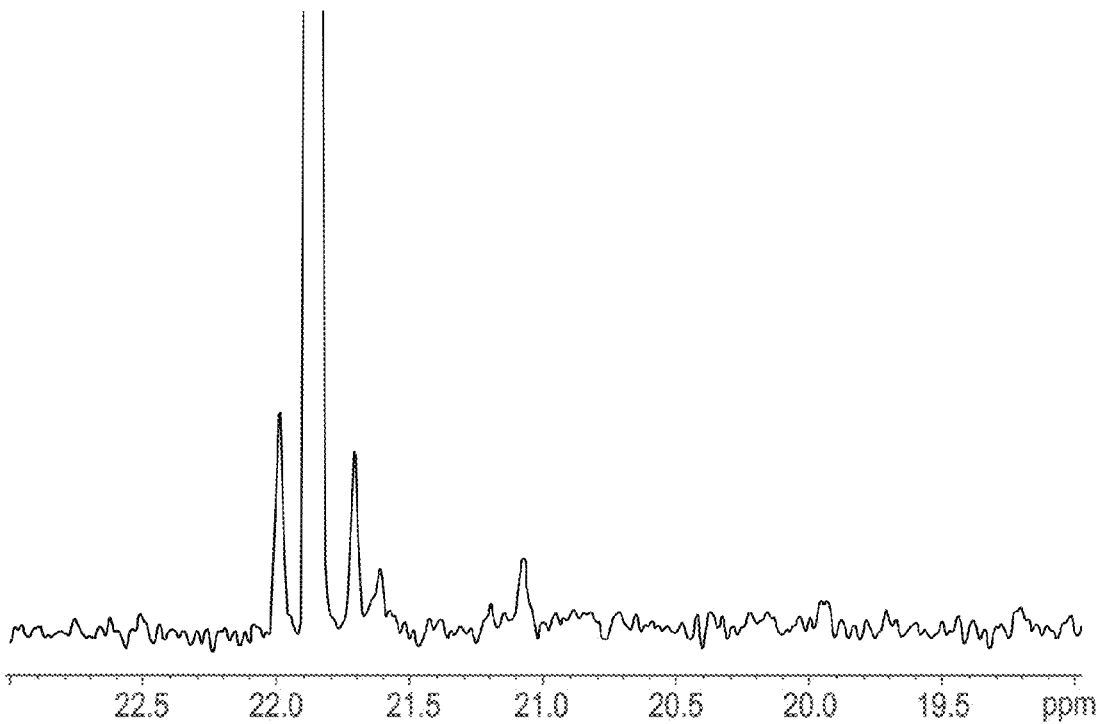
Figure 9:
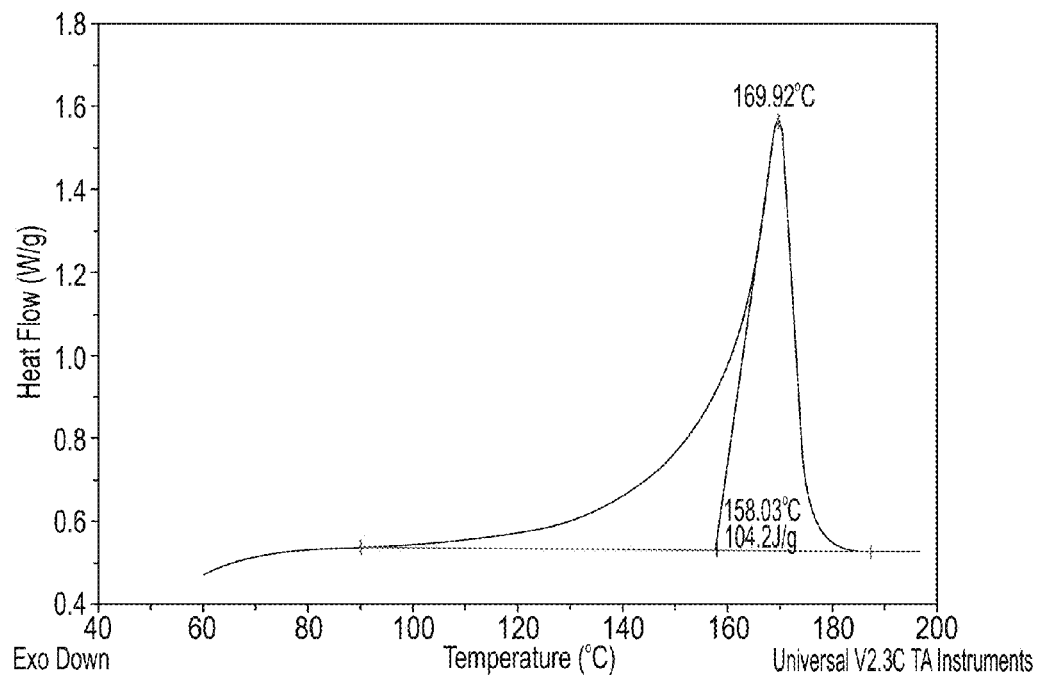
Figure 10:
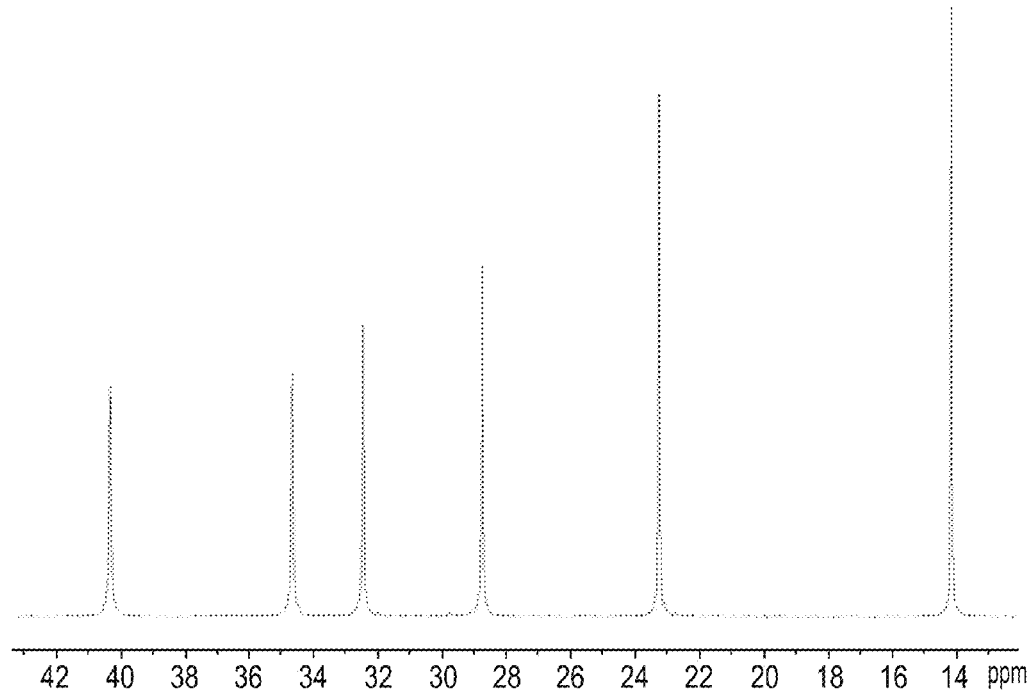

FIG. 1 presents the chemical structures of exemplary Salalen ligand precursors according to some embodiments of the present invention, having a substitution pattern of bulky substituents on one or both the imine-phenol arm and amine-phenol arm and optionally electron-withdrawing substituents (e.g., halogen) on the amine-phenol arm;

FIG. 2 presents the chemical structures of exemplary Salalen ligand precursors according to some embodiments of the present invention, having a reverse substitution pattern of halo-substituents on the imine-arm phenol, and bulky substituents on the amine-arm phenol;

FIG. 3 presents the chemical structures of exemplary Salalen ligand precursors according to some embodiments of the present invention, having halo-substituents on both of the phenol arms;

FIG. 4 presents the chemical structures of exemplary Salalen ligand precursors according to some embodiments of the present invention, based on an N-alkyl-ethylenediamine skeleton;

FIG. 5 presents the chemical structures of exemplary Salalen ligand precursors according to some embodiments of the present invention, based on a 3-carbon atoms-containing bridging moiety;

FIG. 6 presents the chemical structures of exemplary Salalen ligand precursors according to some embodiments of the present invention, based on a 2-aminomethyl-pyrrolidine skeleton;

FIGS. 7A-C present a Chem3d representation of the crystallographic structures of [Ti(Lig$^6$)(O-i-Pr)$_2$] (FIG. 7A), [Ti(Lig$^{28}$)(O-i-Pr)$_2$] (FIG. 7B), and [Hf(Lig$^1$)(O-t-Bu)$_2$] (FIG. 7C), in which the alkyl groups on the labile alkoxo groups, and the hydrogen atoms were omitted for clarity;

FIGS. 8A-B present a $^{13}$C-NMR spectrum (in $C_6D_4Cl_2$) of polypropylene prepared with Lig$^{35}$TiBn$_2$/neat propylene/MAO, in which the lack of observable peaks in the region of 30-45 ppm signifies a very high degree of regioregularity: [mmmm]=99.6% (FIG. 8A) and an expanded Methyl-region of the spectrum presented in FIG. 8A, in which the peaks in the vicinity of the mmmm peak are the $^{13}$C-satellites;

FIG. 9 presents a DSC analysis of a polypropylene prepared with Lig$^{35}$TiBn$_2$ in toluene solution; and FIG. 10 presents a $^{13}$CNMR spectrum (in CDCl$_3$) of poly(1-hexene) prepared with Lig$^6$TiBn$_2$/50 equiv MAO.

DESCRIPTION OF SPECIFIC EMBODIMENTS OF THE INVENTION

The present invention, in some embodiments thereof, relates to chemistry and, more particularly, but not exclusively, to novel processes of tacticity-controlled olefin polymerization, to catalyst systems which comprise as a pre-catalyst novel complexes of Group IV metals which can be utilized in these processes, and to novel ligand precursors for preparing the pre-catalyst novel complexes.

Embodiments of the invention describe the application of Group IV transition metal complexes of Salalen ligands as pre-catalysts in polymerization of olefins following activation with an appropriate co-catalyst. Complexes of Salalen ligands were never employed in such polymerizations in the past.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, a need exists to develop novel methodologies for producing polyolefins with controlled properties, and with controlled tacticity in particular.

In general, isospecific catalysts are capable of discriminating between the two enantiotopic faces of an incoming olefin. This is achieved by the different interactions of these faces with the preferred conformation of the bound polymeryl chain oriented by its interactions with substituents in the vicinity of the chiral metal environment. $C_2$-symmetric catalysts are relatively accessible and their two coordination sites are homotopic, so their isospecificity induction is independent of possible epimerization events of the polymeryl chain. $C_1$-symmetric complexes are structurally more diverse, however, the directing abilities of their two diastereotopic sites are usually different. It has been recognized that isospecific $C_1$-symmetric catalysts should include a directional polymeryl chain migration to the more selective site [Busico et al., *Macromolecules* 1997, 30, 4786-4790].

The present inventors have recognized that Salalen ligands preferably wrap around octahedral Group IV metal centers such that the half-Salan O—N—N donors bind in a fac-mode and the half-Salen O—N—N donors bind in a mer-mode around the octahedral metal center, and places one coordination site trans to the neutral imine N-donor, and the other site trans to the anionic phenoxy O-donor.

The present inventors have envisioned the unique fac-mer wrapping mode of Salalen ligands around Group IV metals, which leads to different environments of the two labile groups, may affect the activities and stereoregulating abilities of potential polymerization catalysts. More specifically, the present inventors have envisioned that the different electronic character of the two labile positions induced by their different trans-donors (a neutral imine N-donor, and an anionic phenoxy O-donor) may encourage a directional polymeryl site epimerization that could enable a tighter control of polymer tacticity and catalyst activity.

While reducing the present invention to practice, a novel methodology for preparing Salalen ligands featuring varying electronic and steric properties has been devised and practiced. Salalen ligands possessing a broad variety of substituents and various diamine skeletons, and Group IV metal complexes obtained therewith, were prepared, and the application of such complexes in polymerization of various polyolefins was demonstrated.

As described in detail in the Examples section that follows, it was uncovered that not only that the Salalen-Group IV metal complexes serve as efficient catalysts, when activated, in the polymerization of various alpha-olefins, the nature of the Salalen ligand affects the activity of the derived catalyst and the properties of the obtained polymer. Notably, it has been uncovered that by controlling the nature of Salalen ligand, the tacticity of the obtained polymer can be controlled, and that catalytic systems based on Salalen-Group IV metal complexes can be used to produce polymers of alpha-olefins, such as polypropylene, having very high isotacticities and regio-regularities which result in high melting transitions (e.g., $T_m$>165° C. for polypropylene). An exemplary titanium-Salalen complex led to polypropylene with isotacticity degree of [mmmm]>99% and $T_m$ higher than 168° C., which is the highest melting temperature ever reported for non-metallocene catalysts, the highest ever reported for a homogeneous titanium-based catalyst, and among the highest ever reported for any catalyst.

It is to be noted that the catalyst systems described herein exhibit controlled-tacticity in polymerization of alpha-olefins, such that the degree and nature of stereoregularity can be pre-determined by the catalyst system of choice. These catalysts therefore can be utilized for producing isotactic polymers as well as elastomers of alpha-olefins, as desired.

It is to be further noted that the degree of chain elongation can be pre-determined by the catalyst system of choice. These catalysts therefore can be utilized for producing polymers of alpha-olefins with varying molecular weights.

It is to be further noted that unlike reports in the art, according to which catalysts that lead to poly(1-hexene) of very high isotacticities lead to polypropylene of considerably lower isotacticity, which is an inferior-grade plastic (see, for example Lamberti et al. *Macromol. Rapid Commun.* 2005, 26, 1866-1871), the catalyst systems described herein show very high stereocontrol in polymerization of both higher olefin monomers such as 1-hexene and styrene and the "slimmer" monomer—propylene.

The readily accessible family of Salalen-Group IV metal complexes introduced herein in exemplary embodiments of the invention represents the most isoselective homogeneous catalyst system reported to date (matching or even exceeding the latest generation heterogeneous Ziegler-Natta catalysts), and includes some of the most isoselective catalysts ever described.

According to an aspect of some embodiments of the present invention, there is provided a process of polymerizing an alpha-olefin, which is effected by contacting the alpha-olefin with a catalyst system which comprises a pre-catalyst comprising a Group IV metal atom and a Salalen ligand complexed therewith and a co-catalyst.

The term "alpha-olefin" is used herein to generally describe unsaturated compounds having a terminal double bond, namely, on the alpha carbon, which can be represented, for example, as $H_2C$=$CRaRb$, wherein Ra and Rb can each independently be hydrogen, alkyl, cycloalkyl and aryl, as defined herein. This term is used herein in the context of monomers used in the polymerization processes described herein, and is referred to herein interchangeably also as "alpha-olefin monomer" or simply as "monomer".

By "contacting" it is meant bringing the pre-catalyst, the co-catalyst and the olefin in such proximity that enables electronic interactions between the metal and the olefin.

In some embodiments, the process is effected in the presence of a solvent, and the contacting encompasses contacting the indicated components (e.g., pre-catalyst, co-catalyst and alpha-olefin) and the solvent.

In some embodiments, the process is effected without a solvent, and is thus a solvent-less process.

In some of these embodiments, the alpha-olefin is in a liquid form. Alpha-olefins suitable for use in such embodiments include any alpha-olefin that is liquid at the temperature at which the polymerization reaction is performed. Exemplary alpha-olefins that are liquid at room temperature include, but are not limited to, 1-pentene, 1-hexene, 1-octene, vinylcyclohexane, and styrene. Other such alpha-olefins are recognizable by any person skilled in the art.

In some embodiments, contacting is effected by placing the alpha-olefin, the pre-catalyst and the co-catalyst in a chemical reactor, with or without a solvent.

Contacting the catalyst system and the alpha-olefin monomers can be effected simply by adding to a reactor the pre-catalyst, the co-catalyst, the monomer and optionally a solvent.

Alternatively, the pre-catalyst may be formed in situ by placing in the reactor a ligand precursor (Salalen ligand precursor as described herein), prior to the formation of a complex with the metal), and a suitable metallic reagent (such as MXp+2, as described herein), which form together the metal complex.

The contacting can thus be effected by placing in the reactor a Salalen ligand precursor, a metallic reagent, the co-catalyst and the alpha-olefin.

Suitable metallic reagents include, but are not limited to, tetrachlorotitanium, tetrabenzyltitanium, tetrakis(dimethylamido)titanium, tetra(iso-propoxy)titanium as well as related complexes of titanium, or related complexes of the other Group IV metals, with or without additional reagents (e.g., a base such as triethylamine).

This in situ pre-catalyst may be activated by the addition of a co-catalyst to afford an active polymerization catalyst, without the previous isolation of the pre-catalyst.

Optionally, contacting is further effected by mixing (e.g., by mechanical or magnetic stirring, shaking, etc.) the alpha-olefin, the pre-catalyst (or the Salalen ligand precursor and the metallic reagent) and the co-catalyst, and optionally the solvent.

The chemical reactor can be, for example, a continuous flow chemical reactor, a batch chemical reactor, and a plugflow chemical reactor, where the size of the chemical reactor can range from a micro-scale laboratory chemical reactor, through a product/process development scale chemical reactor, and up to a large scale commercial chemical reactor.

In some embodiments, the process is effected by placing an alpha-olefin in a liquid form, a pre-catalyst as described herein and a co-catalyst in a chemical reactor, and mixing the components, as described herein. Optionally, an organic solvent is also placed in the reactor.

Suitable organic solvents include, but are not limited to, any non-protic organic solvent which is capable of suspending or dissolving, without decomposing, the pre-catalyst described herein. Examples include, without limitation, alkanes such as pentane, heptane, hexane, dichloromethane and petroleum ether, and aromatic solvents such as benzene, toluene, and chlorobenzene.

In some embodiments, the process is effected while utilizing an alpha-olefin in a gaseous form. Alpha-olefins suitable for use in these embodiments are propylene, ethylene, and 1-butene, or any other alpha-olefin that is gaseous at least at ambient conditions.

In some embodiments, the process is effected by placing a pre-catalyst, a co-catalyst and a solvent, as described herein, in the chemical reactor and charging the reactor with the gaseous alpha-olefin.

In these embodiments, the gaseous alpha-olefin can be flowed into the reactor continuously, batch-wise or in one batch at the beginning of the process. Monitoring the pressure in the reactor can be performed during the process. In some embodiments, the polymerization process proceeds while maintaining a certain pressure in the chemical reactor (e.g., while purging some of the gas during the process and/or by continuously or batch-wise flowing gaseous alpha-olefin to the reactor). Alternatively, the polymerization process is effected by introducing a gaseous alpha-olefin up to a certain pressure, without further controlling the reaction pressure.

In some embodiments, the polymerization is effected at a pressure that ranges from 1 bar to 20 bars, although higher pressures are also contemplated.

In these embodiments, the solvent is optionally selected such that the alpha-olefin is dissolvable therein. Suitable solvents are as described hereinabove.

The above described reactants can be placed in the reactor in any order. In some embodiments, the alpha-olefin or a solution containing same is first added, the pre-catalyst or the Salalen ligand precursor and the metallic reagent are added to the solution and the co-catalyst in then added, optionally in a solution together with the alpha-olefin, with or without a solvent. Optionally, when the alpha-olefin is in a gaseous form, the pre-catalyst or the Salalen ligand precursor and the metallic reagent are added to a solvent, the gaseous alpha-olefin is introduced to the reactor and the reactor is then sealed, and then the co-catalyst is injected into the sealed reactor.

In some embodiments, the polymerization process is effected at a temperature within a range of from 0° C. to above ambient temperature, for example, at 50° C., 60° C., 70° C. and even higher temperatures. In some embodiments, the process is effected at ambient temperature (e.g., room temperature). The process can be effected within a range of temperatures, for example, at a temperature range of 0-5° C., 5-10° C., 0-10° C., 10-15° C., 10-20° C., 20-25° C., 20-30° C., 25-30° C., 30-40° C., 40-50° C., 50-60° C. or 60-70° C. Any temperature or temperature range between 0° C. and 100° C. are contemplated.

The reaction temperature can be controlled as desired, by cooling, chilling or heating the reactor or the components added to the reactor (e.g., the alpha-olefin, a solution containing the pre-catalysts and/or a solution containing the co-catalyst). In some cases, the process involves exothermic reactions.

In some embodiments, contacting is effected by for a time period that ranges from a few seconds (e.g., 5-10 seconds) to a few hours (e.g., 2-24 hours), and may also last for several days (e.g., 2-7 days).

In some embodiments, polymerization is effected for a time period of 2-24 hours.

In some embodiments, the polymerization reaction is terminated by adding an external quencher such as a protic solvent (e.g., methanol), or by otherwise deactivating the active catalyst. Optionally, the process terminates once the alpha-olefin is completely consumed.

Once the process terminates, the formed polymer can be isolated from the reaction mixture. Isolating the polymer can be performed by routine work-up, using methods well-recognized by any person skilled in the art.

Analyzing physicochemical properties and characteristics of the poly(alpha-olefin) products produced by the process can thereafter be effected by various techniques, such as melting point, spectroscopy such as NMR, X-ray crystallography, mechanical strength such as elasticity measurements, etc. Structural information and molecular weight information relating to polymer molecular weight and molecular weight distribution via the polydispersity index (PDI), are also determined.

Exemplary methodologies for implementing the process as described herein are presented in further detail the Examples section that follows.

In some embodiments, the catalyst system described herein is a homogeneous catalyst system.

As used herein throughout, the term "homogeneous catalyst system", or "homogeneous catalysis", refer to catalytic reactions in which the active catalyst is characterized by a homogeneous catalytic site, namely, each molecule has the same catalytic site, as opposed to heterogeneous catalyses, which are characterized by variable catalytic sites.

According to some embodiments of the present invention, the homogeneous catalyst system can be such that the co-catalyst, the pre-catalyst and the alpha-olefin are all in the same phase, typically a liquid phase.

As demonstrated herein, the catalyst system described herein performs efficiently as a homogeneous system, in which at least the pre-catalyst is dissolved in the alpha-olefin or in a solution containing the alpha-olefin.

Optionally, the pre-catalyst and/or the co-catalyst can be adsorbed on a solid support.

The solid support can be, for example, composed of particles onto which the pre-catalyst and/or the co-catalyst are adsorbed. The particles can be, for example, made of silica, magnesia or alumina particles, and can be suspended/dispersed in the reaction medium (the alpha-olefin or a solution containing the same).

As used herein, the term "catalyst system" describes a chemical entity that functions as a catalyst for a polymerization reaction of an alpha-olefin. Herein, the chemical entity is comprised of a pre-catalyst and a co-catalyst which together form an active catalyst for the polymerization reaction.

Hereinafter, the term "pre-catalyst" refers to a chemical entity, in general, and to a chemical compound, in particular, which, when activated by at least one "co-catalyst", becomes part of a catalyst system functional for catalytic polymerization of an alpha-olefin monomer, under proper polymerization reaction conditions. In general, without the presence of at least one co-catalyst, a pre-catalyst is ineffective for catalytic polymerization of an alpha-olefin monomer, and consequently exhibits essentially no catalytic activity for polymerization of an alpha-olefin monomer. Here, when referring to catalytic activity during a polymerization reaction, reference is with respect to the catalytic activity of a pre-catalyst, and it is to be understood that the pre-catalyst functions in concert with at least one co-catalyst for effecting catalytic polymerization of an alpha-olefin monomer.

In some embodiments, as described in further detail hereinbelow, the pre-catalyst comprises labile groups and activation of the pre-catalyst is effected by removing at least one of the labile groups.

Suitable co-catalysts include, but are not limited to, boron Lewis acids such as tris(pentafluorophenyl)boron, $B(C_6F_5)_3$, boron salts such as N,N'-dimethyl anilinium tetrakis(pentafluoro-phenyl)borate, $[PhNH(CH_3)_2][B(C_6F_5)_4]$, and aluminoxanes such as methylaluminoxane (MAO).

In some embodiments, the co-catalyst is methylaluminoxane.

The amount of the co-catalyst used can range from 1 molequivalent to 10,000 molequivalents of a co-catalyst per mol of the pre-catalyst, or from 1 to 1,000 or from 1 to 500 or from 10 to 500, or from 50 to 500 molequivalents of the co-catalyst per mol of the pre-catalyst.

The pre-catalyst is a metal complex of a Group IV metal and a Salalen ligand. In some embodiments, the complex comprises one Salalen ligand per one metal atom.

The expressions "a metal complex of a Group IV transition metal and a Salalen ligand", "a Salalen-Group IV metal complex" and "a Group IV metal atom having a Salalen ligand complexed therewith" and other grammatical combinations of a metal and Salalen are used interchangeably.

In some embodiments, the Group IV metal is a Group IV transition metal such as titanium (Ti), zirconium (Zr) or Hafnium (Hf). Lanthanides with suitable valence can also be employed.

In some embodiments, the metal complex used as a pre-catalyst in embodiments of the present invention can be represented as [Salalen]MXp, wherein M is a Group IV metal as described herein, X is a labile group and p is an integer of 0-4.

The oxidation state of the metal in the metal complex can be 0 to 4, and in some embodiments is 4. A Salalen ligand is typically coordinated to the metal atom via two covalent bonds (via the phenolate oxygens) and two coordinative bonds (via the amine-nitrogen and the imine-nitrogen). Labile groups, denoted herein as X, and which are typically anionic groups, as well as neutral groups, may complete the coordination sphere of the metal.

Hence "p" is an integer that describes the number of labile groups that are attached to the metal atom, whereby additional groups can be present in case "p" labile groups do not complete the coordination sphere of the metal.

As used herein, the term "labile group" encompasses chemical groups which are attached to the metal atom, and which can be removed or replaced in the presence of a co-catalyst. Labile groups are typically univalent anionic groups. A "labile group" can be regarded as a ligand that participates in the catalytic reaction, as is sometimes referred to in the art as an "actor" ligand.

Exemplary labile groups include, but are not limited to, univalent anionic ligands such as a halide, a hydride, a saturated or unsaturated hydrocarbyl, an alkoxide, an aryloxide, a dialkylamide, or an arylamide, as well as divalent anionic ligands such as a cyclometallated hydrocarbyl.

In some embodiments, the oxidation state of the metal is 4, and the number of labile groups "p" is 2. In some embodiments, the oxidation state of the metal is 4, and the number of labile groups "p" is 1. In these embodiments, an additional group is attached to the metal.

The additional group(s) can be, for example, neutral univalent ligands such as, but not limited to, THF or toluene.

In some embodiments, the pre-catalyst utilized in the process described herein is prepared from a Salalen ligand precursor (Salalen-$H_2$) having general Formula I as follows:

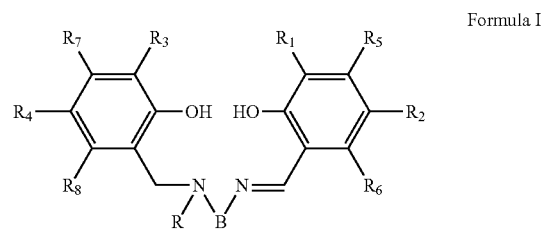

Formula I wherein:

B is a bridging moiety being at least 2 carbon atoms in length;

R is hydrogen, alkyl, cycloalkyl, aryl, heteroaryl and heteroalicyclic, or, alternatively, forms a 5-membered or 6-membered cyclic or heterocyclic ring with a carbon atom of said bridging moiety; and $R_1$-$R_8$ are each independently selected from the group consisting of hydrogen, alkyl, cycloalkyl, aryl, halogen, alkoxy, aryloxy, heteroalicyclic, heteroaryl, and nitro, provided that at least one of $R_1$-$R_4$ is other than hydrogen.

It is to be noted that when the expression Salalen-$H_2$ describes a ligand precursor, when not complexed to the metal atom, whereby upon complexation, the phenolic functions are converted to phenolates (each looses a proton).

The pre-catalyst according to these embodiments, can thus be represented by the general Formula II, as follows:

Formula II wherein:

Q is MXp,

M is a group IV element, e.g., a Group IV transition metal atom as described herein; X is a labile group as described herein; and p is an integer ranging from 0 to 4, as described herein, and all other variables are as described for the Salalen ligand precursor.

The dashed lines represent the complexation between the metal atom and the Salalen ligand. In some embodiments, the dashed lines represent covalent bonds formed between each of the phenolate oxygens and the metal atom and each of the nitrogen atoms and the metal atom.

M can be Ti, Zr or Hf. In some embodiments, M is Ti. The selected metal can affect the properties of the produced polymer. In some embodiments, metal complexes containing Ti are used to produce polymers with higher degree of tacticity while metal complexes containing Zr or Hf can be used to produce polymers with lower tacticity, such as rubbery or otherwise elastic polymers.

The Salalen ligands and the pre-catalyst metal complexes containing same include a diamino skeleton composed of an amine-nitrogen and an imine-nitrogen, each possessing a phenol arm attached thereto (via a one-carbon moiety).

B in Formulae I and II hereinabove denotes a bridging moiety linking the two nitrogen atoms.

In some embodiments, the bridging moiety comprises a chain of 2 or more carbon atoms, optionally, yet less preferably, interrupted by one or more heteroatoms.

The —RN—B—N=moiety in Formulae I and II above denotes what is referred to herein as the "skeleton" or "diamino skeleton" of the Salalen ligand (and of the metal complexes formed therewith).

In some embodiments, the bridging moiety comprises a chain of 2 carbon atoms, or 3 carbon atoms. However, longer chains, of 4, 5, 6, or more carbon atoms are contemplated, optionally interrupted by an aryl, cycloalkyl, heteroalicyclic and heteroaryl groups.

The bridging moiety can include asymmetric centers, such as in the case of trans-1,2-diaminocyclohexane, or 2-aminomethyl-pyrrolidine, thus making the whole Salalen ligand chiral, as is further detailed hereinbelow.

In some embodiments, the bridging moiety comprises a 2 carbon atoms-chain and can be represented by general Formula IVA:

$$—C_1(R_9R_{10})—C_2(R_{11}R_{12})—\qquad \text{Formula IVA}$$

wherein $R_9$-$R_{12}$ are each independently selected from the group consisting of hydrogen, alkyl, cycloalkyl, aryl, heteroaryl and heteroalicyclic or, alternatively, at least two of R and $R_9$-$R_{12}$ form a 5-membered or 6-membered cyclic or heterocyclic ring.

A "cyclic ring" encompasses an all-carbon ring structure, such as aryl or cycloalkyl, as defined herein, and further encompasses structures containing more than one ring (e.g., bicyclic structures).

A "heterocyclic ring" encompasses a ring structure that contains one or more heteroatoms such as nitrogen, oxygen, sulfur, and the like, such as heteroalicyclic and heteroaryl, as defined herein, and further encompasses structures containing more than one ring (e.g., bicyclic structures).

In some embodiments, each of $R_9$-$R_{12}$ is hydrogen, and the bridging moiety is simply an ethane bridging the two nitrogens.

In some embodiments, one of $R_9$-$R_{12}$ is other than hydrogen.

In some embodiments, two of $R_9$-$R_{12}$ form together a ring, for example, a cycloalkyl, as described herein, and optionally a heteroalicyclic (e.g., in cases where one of $R_9$-$R_{12}$ is a substituent that is further substituted by functionalities such as amine or hydroxyl). As noted hereinabove, two of $R_9$-$R_{12}$ can form, for example, a trans-cyclohexane, and a skeleton of trans-1,2-diaminocyclohexane, which imparts chirality to the ligand and the complex containing same. $R_9$-$R_{12}$ can optionally form together an aryl.

In some embodiments, $R_9$ and R form a heterocyclic ring which includes the amine-nitrogen of the skeleton, thus forming, for example, a pyrrolidine, and a skeleton of 2-aminomethyl-pyrrolidine, which imparts chirality to the ligand and the complex containing same. Alternatively, $R_9$ and R can form a heterocyclic ring such as piperidine, morpholine, piperazine, tetrahydroazepine and the like.

Other substituents on the bridging moiety, denoted $R_9$-$R_{12}$ in Formula IVA, are also contemplated, as long as they do not interfere with the stability of the ligand and/or the complex formed therewith.

In some embodiments, the bridging moiety has 3 carbon atoms and can be represented by the general Formula IVB:

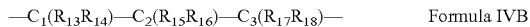

$$—C_1(R_{13}R_{14})—C_2(R_{15}R_{16})—C_3(R_{17}R_{18})—\qquad \text{Formula IVB}$$

wherein $R_{13}$, $R_{14}$, $R_{17}$ and $R_{18}$ are each independently selected from the group consisting of hydrogen, alkyl, cycloalkyl, aryl, heteroaryl and heteroalicyclic, $R_{15}$ and $R_{16}$ are each independently selected from the group consisting of hydrogen, alkyl, cycloalkyl, aryl, heteroaryl, heteroalicyclic, hydroxyl, alkoxy, thiol, thioalkoxy, aryloxy, and amine, or, alternatively, at least two of R and $R_{13}$-$R_{18}$ in Formula IVB form a 5-membered or 6-membered cyclic or heterocyclic ring.

In some embodiments, each of $R_{13}$-$R_{18}$ is hydrogen.

In some embodiments, one or more of $R_{13}$-$R_{18}$ is other than hydrogen.

In some embodiments, at least two of $R_{13}$-$R_{18}$ form a cyclic ring, such as a cycloalkyl or an aryl, as defined herein.

In some embodiments, $R_{15}$-$R_{18}$ form together an aryl such as phenyl, and optionally a higher aryl such as naphthalenyl. Alternatively, $R_{13}$-$R_{16}$ form together an aryl.

In some embodiments, one or more of $R_{13}$-$R_{18}$ and R form together a heterocylic ring, as described herein.

As shown in the Examples section that follows, exceptional activity and control on the tacticity of the formed polymer was obtained while utilizing pre-catalysts in which the bridging unit was a chiral unit, for example, in the form of 2-aminomethyl-pyrrolidine.

In some embodiments, the amine-nitrogen in the skeleton, denoted R in Formulae I and II herein, is alkyl.

The alkyl can be methyl, ethyl, propyl, isopropyl, or a higher alkyl (e.g., of 4, 5, 6 or more carbon atoms), or can be an alkaryl (an alkyl substituted by an aryl, as defined herein) such as benzyl.

As noted herein, the performance of the pre-catalyst, in terms of e.g., the catalytic activity of the active catalyst and the characteristics of the obtained polymer, is affected by the electronic and steric nature of the substituents of the phenolate rings of the Salalen ligand of the pre-catalyst complex, denoted as $R_1$-$R_8$ in Formulae I and II hereinabove.

In some embodiments, the nature of the substituents at positions ortho and para to the phenolate function affects the performance of the catalyst system.

Accordingly, in some embodiments, at least one of $R_1$-$R_4$ is other than hydrogen.

In some embodiments, $R_5$-$R_8$ are each hydrogen, although other substituents at these positions are also contemplated.

It has been surprisingly uncovered herein that pre-catalysts possessing bulky substituents on one or more of the phenolate rings provide for polymers with improved characteristics.

In some embodiments, each of $R_1$-$R_4$ is independently an alkyl.

In some embodiments, the alkyl is a bulky alkyl.

As used herein, the phrase "bulky", in the context of a group or an alkyl in particular, describes a group that occupies a large volume. A bulkiness of a group or an alkyl is determined by the number and size of the atoms composing the group, by their arrangement, and by the interactions between the atoms (e.g., bond lengths, repulsive interactions). Typically, lower, linear alkyls are less bulky than branched alkyls; bicyclic molecules are more bulky than cycloalkyls, etc.

Exemplary bulky alkyls include, but are not limited to, branched alkyls such as tert-butyl, isobutyl, isopropyl and tert-hexyl, as well as substituted alkyls such as triphenylmethane (trityl) and cumyl.

In some embodiments, the alkyl is tert-butyl, such that at least one, at least two, at least three or each of $R_1$-$R_4$ is tert-butyl.

In some embodiments, at least one of $R_1$ and $R_2$ is tert-butyl and/or other bulky alkyl.

In some embodiments, each of $R_1$ and $R_2$ is tert-butyl and/or other bulky alkyl.

In embodiments where at least one of $R_1$-$R_4$ or $R_1$ and $R_2$ is a bulky alkyl or is tert-butyl, other substituents at these positions ($R_1$-$R_4$) can be for example, lower alkyl (e.g., methyl), another bulky group, as described hereinafter, or one or more electron-withdrawing groups such as halogen.

In some embodiments, each of $R_1$ and $R_2$ is tert-butyl and/or other bulky alkyl and at least one, or both, of $R_3$ and $R_4$, is halogen.

In other embodiments, at least one of $R_1$-$R_4$ is halogen.

In some embodiments, each of $R_1$-$R_4$ is halogen.

In some embodiments, at least one of $R_3$ and $R_4$ is halogen.

In some embodiments, each of $R_3$ and $R_4$ is halogen.

The halogen can be chloro, bromo, and iodo, and any combination thereof.

In some embodiments, each of $R_1$-$R_4$ is chloro, each of $R_1$-$R_4$ is bromo, or each of $R_1$-$R_4$ is iodo.

In some embodiments, each of $R_3$ and $R_4$ is chloro, each of $R_3$ and $R_4$ is bromo, or each of $R_3$ and $R_4$ is iodo.

In some embodiments, at least one of $R_1$-$R_4$ is a bulky rigid group.

As used herein, the phrase "bulky rigid group" describes a bulky group, as defined herein, with reduced number of free-rotating bonds. Such a group, unlike bulky alkyls, are rigid in terms of free rotation. Exemplary bulky rigid groups that are suitable for use in the context of embodiments of the invention include, but are not limited to, aryl, heteroaryl, cycloalkyl and/or heteroalicyclic, as defined herein.

In some embodiments, the rigid bulky group is such that has a total of 7 carbon atoms or more, each being substituted or unsubstituted.

In some embodiments, the bulky rigid group is a bicyclic group, comprising two or more of a cycloalkyl, aryl, heteroalicyclic or heteroaryl fused or linked to one another.

An exemplary bulky rigid group is adamantyl, for example, 1-adamantyl.

In some embodiments, $R_1$ is a bulky rigid (e.g., cyclic) group. In some embodiments $R_3$ is a bulky rigid group.

In some embodiments, $R_1$ is adamantyl (e.g., 1-adamantyl).

In some embodiments, $R_1$ is adamantyl (e.g., 1-adamantyl), $R_2$ is alkyl (e.g., methyl) and one or both of $R_3$ and $R_4$ is halogen (e.g., chloro, bromo and/or iodo).

In some embodiments, $R_3$ is adamantyl (e.g., 1-adamantyl), $R_4$ is alkyl (e.g., methyl) and one or both of $R_1$ and $R_2$ is halogen (e.g., chloro, bromo or iodo).

The substituents on the imine-side phenol ring ($R_1$ and $R_2$) and on the amine-side phenol ring ($R_3$ and $R_4$) can be modified by choice of the starting materials used for preparing the precursor ligand, as is further detailed hereinafter.

The pre-catalyst metal complex can be prepared by any methods known in the art. An exemplary method is described in the Examples section that follows. Alternatively, it can be prepared in situ, as described hereinabove.

While embodiments of invention relate to a pre-catalyst having general Formula I as above, it is to be noted that pre-catalysts having other Salalen ligands are also contemplated.

Various types of homo-polymerization and co-polymerization processes of different types of alpha-olefins can be performed using the catalyst system described herein, under different polymerization conditions.

Exemplary alpha-olefin monomers that can be utilized include, but are not limited to, ethylene, propylene, 1-butene, 1-pentene, 1-hexene, vinyl-cyclohexane, 4-methyl-1-pentene, as well as higher olefins (containing more than 6 carbon atoms and being branched or unbranched) and aromatic olefins such as styrene.

Mixtures of alpha-olefins, such as, but not limited to, the alpha-olefins described herein, can be utilized in the process described herein, so as to produce co-polymers.

The term "polymerization" therefore encompasses both "homo-polymerization" and "co-polymerization".

In some embodiments, the alpha-olefin is propylene.

In some embodiments, the process is utilized for producing tacticity-controlled polymerization of alpha-olefins.

Thus, by selecting a suitable pre-catalyst, highly stereo-regular (e.g., highly isotactic) polymers can be produced, if so desired. Alternatively, the pre-catalyst of choice is such that produces less steroregular polymers, if so desired.

Similarly, the molecular weight of the polymer can be controlled by virtue of the pre-catalyst used.

The control on the polymer's characteristics can be made by virtue of either the Salalen ligand precursor, the metal M and/or the labile groups X, guidelines for which are exemplified in the Examples section that follows.

In some embodiments, the obtained polymer of the alpha-olefin is characterized by an isotacticity degree of at least 50%.

As noted hereinabove, in some embodiments, the isotacticity degree [mmmm] is higher than 70%, higher than 90% and in some cases even higher than 99%.

In some embodiments, the polymer of the alpha-olefin is characterized by a molecular weight of $M_w$=at least 300,000 grams/mol, or of at least $M_w$=400,000 grams/mol. Polymer molecular weights as high as $M_w$=800,000, 1,000,000 and even 2,000,000 grams/mol and higher are contemplated.

In some embodiments, the polymer of the alpha-olefin is characterized by a molecular weight distribution (PDI) lower than 3, lower than 2 and in some cases lower than 1.5 or lower than 1.1.

In some embodiments, the alpha-olefin is propylene and the obtained polypropylene is characterized by a melting transition temperature of at least 150° C. and even of at least 160° C. In some embodiments, the obtained polypropylene is characterized by a melting transition temperature of at least 165° C., and even of at least 168° C.

The above described characteristics of the obtained polymers are in line with most of the industrial requirements of alpha-olefin polymers, and in some cases are superior to the characteristics of currently produced polymers of alpha-olefins.

Accordingly, in some embodiments, there is provided a process of preparing a polypropylene having a melting transition temperature of at least 165° C., or of at least 168° C., as is further detailed hereinunder.

Further according to embodiments of the present invention, there is provided a polymer (or co-polymer) of an alpha-olefin (or of a mixture of two or more alpha-olefins), as described herein, which is prepared by the process as described herein.

Further according to embodiments of the present invention there is provided a polymer of an alpha-olefin, as described herein, which is characterized by an isotacticity degree of at least 50%, at least 70%, at least 90%, at least 95% and even of 99% and higher.

Further according to embodiments of the present invention there is provided a polymer of an alpha-olefin, as described herein, which is characterized by a molecular weight of at least $M_w=200,000$ grams/mol, or of at least $M_w=400,000$ grams/mol, as described herein.

Further according to embodiments of the present invention there is provided a polymer of an alpha-olefin, as described herein, which is characterized by a molecular weight distribution (PDI) lower than 3, as described herein.

Further according to embodiments of the present invention there is provided a polymer of an alpha-olefin, as described herein, which is characterized by a high tacticity, high molecular weight and low PDI, as described herein. In some embodiments, the polymer is produced by a process as described herein.

Accordingly, embodiments of the present invention are of a method of controlling a tacticity, a molecular weight and/or a PDI of a polymer of an alpha-olefin, which is effected by contacting the alpha-olefin with a suitable pre-catalyst according to the guidelines provided herein for a Salalen-Group IV metal complex pre-catalysts.

Further according to embodiments of the present invention there is provided a polymer of propylene (a polypropylene), characterized by a high tacticity, high molecular weight and low PDI, as described herein. In some embodiments, there is provided a polypropylene, characterized by a melting transition temperature of at least 165° C., or of at least 168° C.

According to another aspect of some embodiments of the present invention there is provided a process of preparing a polypropylene which is characterized by a melting transition temperature of at least 165° C., the process comprising polymerizing propylene in the presence of a catalyst system that comprises a ligand-metal complex.

The phrase "ligand-metal complex" is used herein to describe an inorganic complex which comprises one or more non-labile ligands (spectator ligands), as defined herein.

Catalyst systems comprising a ligand-metal complex are typically characterized as "single site" catalysts, featuring a homogeneous catalytic site, as defined herein.

In some embodiments, the ligand-metal complex is an inorganic complex of a Group IV metal, e.g., of Ti.

In some embodiments, the ligand-metal complex is a non-metallocene complex, namely, it does not include a cyclopentadienyl ligand.

In some embodiments, the catalyst system is a homogeneous catalyst system, as defined herein.

In some embodiments, the polypropylene is characterized by a melting transition temperature of at least 168° C.

In some embodiments, the polypropylene is characterized by a molecular weight distribution (PDI) lower than 3 and even by a PDI of 2 or lower.

It is noted that current processes of preparing polypropylene by polymerizing propylene typically involve either metallocene complexes, which are disadvantageous as discussed hereinabove, or heterogeneous catalysis, which typically result in a polymer having a PDI of 3 or higher, due to the non-homogenous nature of the catalytic sites therein.

In some embodiments, the polypropylene is prepared while utilizing a catalyst system which is a homogeneous catalyst system, as defined herein, and in which the pre-catalyst and/or co-catalyst are either dissolvable in a liquid or are adsorbed to particles that are dispersible/suspendable in a liquid.

In some embodiments, the metal-ligand complex comprises a Group IV metal and a Salalen ligand complexed therewith, as described herein.

Further according to an aspect of some embodiments of the present invention there is provided a polypropylene characterized by a melting transition temperature of at least 165° C., or of at least 168° C., prepared by the process described hereinabove.

Further according to an aspect of some embodiments of the present invention there is provided a polypropylene characterized by a melting transition temperature of at least 168° C. (e.g., of 169° C. or higher), and by a PDI lower than 3 (e.g., of about 2 or lower).

It is to be noted that currently produced polypropylenes are either characterized by high melting transition temperature yet by high PDI, or by lower melting transition temperature.

As noted hereinabove, the present inventors have designed and successfully prepared and practiced novel Salalen ligands which were successfully used in preparing metal complexes suitable for use as pre-catalysts for polymerizing alpha-olefins.

Accordingly, according to an aspect of some embodiments of the present invention there is provided a compound having the general Formula I*:

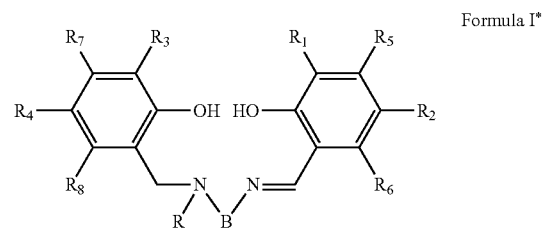

Formula I* wherein:

B is a bridging moiety being at least 2 carbon atoms in length, as described herein;

R is hydrogen, alkyl, cycloalkyl, aryl, heteroaryl and heteroalicyclic, or, alternatively, forms a 5-membered or 6-membered heterocyclic ring with a carbon atom of said bridging moiety; as described herein, and $R_1$-$R_8$ are each independently selected from the group consisting of hydrogen, alkyl, cycloalkyl, aryl, halogen, alkoxy, aryloxy, heteroalicyclic, heteroaryl, and nitro, as described herein, provided that:

(i) at least one of $R_1$-$R_4$ is independently a rigid bulky group, as defined herein;

(ii) each of $R_1$-$R_4$ is independently a halogen, as described herein; and/or (iii) said R forms a 5-membered or 6-membered heterocyclic ring with a carbon atom of said bridging moiety, as described herein.

Further according to an aspect of some embodiments of the present invention there is provided a metal complex having the general formula II*:

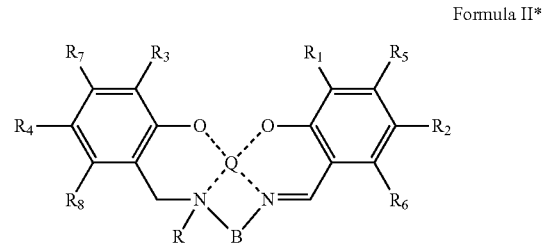

Formula II* wherein:

Q is MXp, as defined herein, and all other variables are as defined for Formula I* hereinabove.

In some embodiments, the bridging moiety has a general Formula IVA, as described herein, and $R_9$ and R form said heterocyclic ring.

In these embodiments, $R_1$-$R_8$ are as described hereinabove for Formula I.

In some embodiments, $R_1$ and/or $R_3$ is a bulky rigid group, as described herein. (e.g., adamantyl).

While it is demonstrated herein that the choice of the Salalen ligand precursor can affect the performance of the catalyst system in the polymerization of alpha-olefins, designing suitable ligand precursors can be readily effected while utilizing the novel methodology designed by the present inventors, which enable to control the nature of the skeleton of the ligand precursor and/or the nature of the substituents of the phenolate rings by virtue of the starting material.

According to an aspect of some embodiments of the present invention, there is provided a process of preparing a Salalen ligand having the general Formula I:

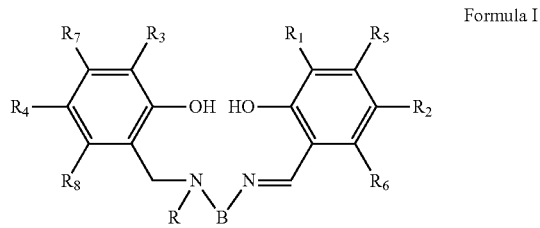

Formula I with the variables being as described hereinabove.

The process is effected by reacting a diamino compound having the formula R—NH—B—NH$_2$, wherein B and R are as defined herein for Formula I, with a carbonyl-containing compound having the formula:

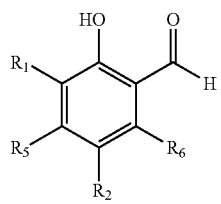

(a substituted salicylaldehyde or 2-hydroxybenzalaldehyde), to thereby obtain an imino-containing compound of the formula:

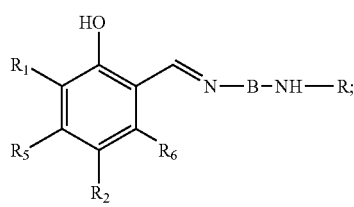

and reacting said imino-containing compound with a compound having the formula:

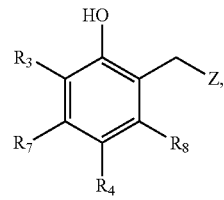

wherein Z is a leaving group.

As used herein throughout, and is well known in the art, the phrase "leaving group" refers to a chemical moiety that can be easily replaced by a nucleophilic moiety in a nucleophilic reaction. Representative examples of leaving groups include, without limitation, halogen, alkoxy, aryloxy, thioalkoxy, thioaryloxy, sulfinyl, sulfonyl, carboxy and carbamyl, as these terms are defined hereinabove, with halogen and alkoxy being the presently most preferred. Additional examples of leaving groups include, without limitation, azide, sulfonamide, phosphonyl and phosphinyl.

In some embodiments, the leaving group Z is halogen such as bromo.

The reaction of forming the imine-containing compound is performed under conditions for performing a Schiff reaction, as known in the art, whereby the following reaction is performed under conditions suitable for performing a nucleophilic addition reaction, as known in the art.

The substituents $R_1$-$R_8$ of the reactant determine the substitution pattern of the Salalen ligand precursor and the metal complex formed therewith, described herein.

The methodology described herein can be further utilized for preparing any Salalen-metal complex, including the Salalen-Group IV metal complexes described herein.

Accordingly, in some embodiments, the process described herein further comprises reacting the compound having Formula I as prepared by the process described hereinabove, with a metallic reagent, as described herein. In some embodiments, such a process is used for preparing a metal complex having general Formula II, as described herein.

The term "alkyl", as used herein, describes a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a lower alkyl having 1 to 4 carbon atoms. The alkyl group may be substituted or unsubstituted, as indicated herein.

The term "alkenyl", as used herein, describes an alkyl, as defined herein, which contains a carbon-to-carbon double bond.

The term "alkynyl", as used herein, describes an alkyl, as defined herein, which contains carbon-to-carbon triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halogen, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatived thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" group describes an —S(=O)$_2$—R' group, where Rx is as defined herein.

A "carbamyl" group describes an —OC(=O)—NR'R" group, where R' is as defined herein and R" is defined for R'.

A "nitro" group refers to a —NO$_2$ group.

A "cyano" or "nitrile" group refers to a —C≡N group.

The term "piperazine" refers to a

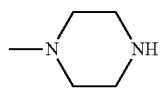

group or a

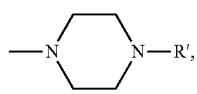

where R' as defined hereinabove.

The term "piperidine" refers to a

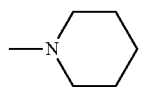

group.

The term "pyrrolidine" refers to a

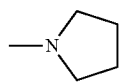

group.

The term "pyridine" refers to a

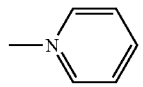

group.

The term "morpholine" refers to a

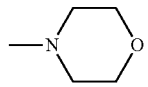

group, and encompasses also thiomorpholine.

The term "thiomorpholine" refers to a

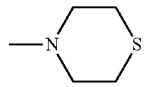

group.

The term "hexahydroazepine" refers to a

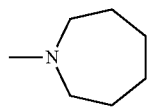

group.

As used herein, the term "azide" refers to a —$N_3$ group.

The term "sulfonamide" refers to a —S(=O)$_2$—NR'R" group, with R' and R" as defined herein.

The term "phosphonyl" describes an —O—P(=O)(OR')$_2$ group, with R' as defined hereinabove.

The term "phosphinyl" describes a —PR'R" group, with R' and R" as defined hereinabove.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

All experiments employing metal complexes were performed under an atmosphere of dry nitrogen in a nitrogen-filled glovebox.

All reagents were of analytical grade.

Pentane purchased from J. T. Baker was washed with $HNO_3/H_2SO_4$ prior to distillation from Na/benzophenone/tetraglyme under argon atmosphere.

Diethylether purchased from Gadot was refluxed over Na/benzophenone and distilled under argon atmosphere.

Toluene purchased from Bio-Lab was refluxed over Na and distilled under argon atmosphere.

Benzene purchased from Loba-Chemie, Methanol purchased from Gadot, and tetrahydrofuran purchased from Bio-Lab were used as received.

Benzyl magnesium chloride, salicylaldehyde, 3,5-dichlorosalicylaldehyde, 3,5-dibromosalicylaldehyde, 3,5-diiodosalicylaldehyde, N-Methylethylenediamine, N-benzylethylenediamine, N-isopropylethylenediamine, triethylamine, N-methyl-1,3-propane diamine, 4-chloro-2-methylphenol, $TiCl_4$, Ti(IV) iso-propoxide, Tetrakis(dimethylamido)titanium, and Zirconium (IV) tert-butoxide, were purchased from Aldrich and used as received.

Hafnium (IV) tert-butoxide, and tetrabenzylhafnium were purchased from Strem were used as received.

S-(2)-Pyrrolidinemethanamine.2HCl, and 2-Amino-N-methyl-benzenemethanamine.2HCl were purchased from Amatek Chemical and used as received.

Formaldehyde (37% in water) was purchased from Gadot and used as received.

N-ethylethylenediamine and sodium borohydride were purchased from Fluka and used as received.

3,5-di-tert-butyl-2-hydroxybenzaldehyde was purchased from Appolo and used as received.

1-Hexene purchased from Aldrich, and styrene purchased from Fluka, were passed through alumina prior to use.

Polymerization grade propylene (99.5%) purchased from Maxima, and ethylene (99.5%) purchased from Gas-Ron, were passed through molecular sieves prior to use.

Tetrabenzyltitanium and tetrabenzyl zirconium were synthesized according to a published procedure [U. Zucchini, et al., *J. Organomet. Chem.* 1971, 26, 357-372]. and the titanium complex was used shortly after.

Tris(pentafluorophenyl)borane was obtained from Strem Chemicals.

Solid Methylaluminoxane (MAO) was obtained by solvent removal from a 10 wt % solution in toluene purchased from Aldrich.

3-Adamantyl-2-hydroxy-5-methylbenzaldehyde, 3-trityl-2-hydroxy-5-methylbenzaldehyde, 3,5-cumyl-2-hydroxybenzaldehyde [K. P. Bryliakov, et. al., *Eur. J. Org. Chem.*

2008, 3369-3376], 2-((methylamino)ethylimino)methyl)-4,6-di-tert-butylphenol [Yeori et al. *Inorg. Chem. Commun.* 2004, 7, 280-282], 2-(bromomethyl)-4,6-dichlorophenol [Gendler et al., *J. Am. Chem. Soc.* 2008, 130, 2144-2145], 2-(bromomethyl)-4-adamantyl-6-methyl-phenol, 2-(bromomethyl)-4-trityl-6-methyl-phenol, 2-(bromomethyl)-4,6-tert-butyl-phenol [Cohen et al., *Organometallics* 2009, 28, 1391-1405], and 2-(bromomethyl)-4,6-diiodophenol [Cohen et al., *Macromolecules* 2010, 43, 1689-1691] were synthesized according to published procedures.

NMR data for the intermediate organic compounds, ligand precursors, titanium complexes, and poly(1-hexene) samples were recorded on a Bruker AC-400 spectrometer. $C_6D_6$ was employed as solvent for the Group IV metal complexes for $^1H$ NMR and $^{13}C$ NMR analyses (impurities in benzene-$d_6$ at δ 7.15 and $^{13}C$ chemical shift of benzene at δ 128.70 were used as reference). $CDCl_3$ was used as solvent for the other samples (chemical shift of TMS at δ=0.00, and $^{13}C$ NMR chemical shift of the solvent at δ=77.16 were used as reference).

X-ray diffraction measurements for complexes [Ti(Lig$^6$)(O-i-Pr)$_2$], [Ti(Lig$^{28}$)(O-i-Pr)$_2$], and [Hf(Lig$^1$)(O-t-Bu)$_2$] were performed on a Nonius Kappa CCD diffractometer system, using MoKα (λ=0.7107 Å) radiation. The analyzed crystals grown from chilled solutions at −35° C. were embedded within a drop of viscous oil and freeze-cooled to ca. 110 K. The structures were solved by a combination of direct methods and Fourier techniques using SIR-97 software, and were refined by full-matrix least squares with SHELXL-97.

Elemental analyses were performed in the microanalytical laboratory in the Hebrew University of Jerusalem.

Example 1

Salalen Ligand Precursors

A variety of Salalen ligand precursors were prepared. The ligand precursors were designed to include a broad variety of structural modifications that lead to controlled variation of the structures of catalyst systems containing same, and thereby may control the catalytic activity of these catalyst systems, for example, by means of controlling the properties of polymers produced by catalytic polymerization.

The prepared Salalen ligand precursors include the following structural variations: variations of the diamine backbone forming the bridging moiety, including, for example, different lengths, rigidities and chemical character; and different substituents of the tertiary amine donor, including, for example, alkyl groups of different bulk and nature such as methyl, ethyl, isopropyl or benzyl; and variation of the substitution patterns on the two phenol rings, by means of, for example, alkyl, cycloalkyl or aryl substituents of different bulk, and halo groups of different electron withdrawing abilities and bulk.

Some of the Salalen ligand precursors described herein have never been described heretofore.

In a search for a straightforward, high-yielding, synthetic pathway for preparing such a broad variety of Salalen ligand precursors, the present inventors have conceived a synthetic pathway that employs readily available starting materials, and involves a minimal number of steps and diminished formation of impurities that may hamper catalyst performance and require tedious purification steps.

A general synthetic method was developed to this effect and was found suitable for all Salalen ligand precursors. The synthetic pathway is generally illustrated in Scheme 1 below:

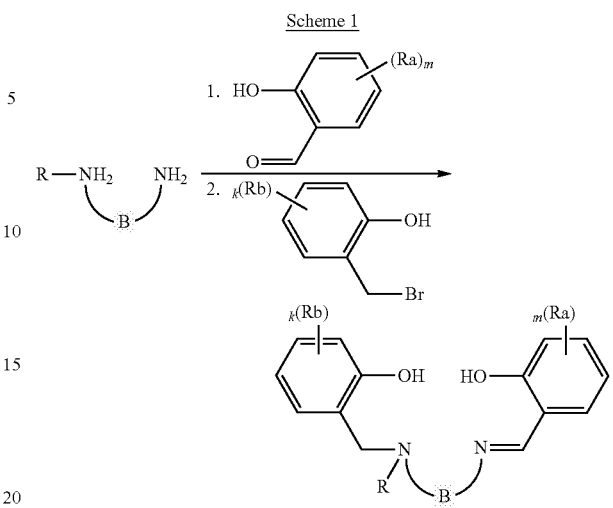

Scheme 1 wherein: B is a "bridge" linking the two amines in the diamine central building block; R is a substituent on the tertiary amine and Ra and Rb generally represent the substitution pattern on each phenol ring.

As used herein, the terms "bridge" and "bridging unit" are used interchangeably.

The diamine central building block is also referred to herein as the "diamine skeleton" or simply "skeleton".

As can be seen in Scheme 1, the general synthetic pathway involves a two-step reaction sequence of the diamine central building block: a condensation reaction with a carbonyl functionality of the appropriately substituted phenol (e.g., a substituted salicyladehyde), followed by nucleophilic attack of the formed intermediate on the halo-methyl derivative (bromo-methyl being accessible and performing satisfactorily) of an appropriately substituted second phenol. The starting materials are either commercially available or easily synthesized. The condensation reaction may involve either the two amine groups of the starting diamine to form an aminal/ketal functionality or may involve only the primary amine of the starting diamine, so as to form an imine intermediate. For convenience, herein throughout, both these intermediates are referred to as an imine intermediate. The following nucleophilic substitution on the halomethyl group of a second substituted phenol leads selectively to the ligand precursor for any form of the intermediate produced in the condensation.

It is noteworthy that, in comparison to common synthetic schemes published in the art, the synthetic pathway presented herein circumvents the application of protecting groups and their removal. Use of expensive metal-mediated cross-coupling reactions is also circumvented. Nonetheless, other synthetic methodologies, such as, for example, those described in the art for preparing Salalen ligand precursors, are also contemplated and can be used for preparing the Salalen ligand precursors described herein, by selecting suitable reagents. Such a selection should be recognized by any person skilled in the art.

Using the above-described general synthetic pathway, various Salalen ligand precursors were synthesized. All syntheses required two steps from either commercially available or readily available materials.

The following describes in more detail general and exemplary procedures of preparing Salalen ligands of several subfamilies, categorized either by the nature of the diamino skeleton (and the bridging moiety) and/or by the nature of the substituent(s) on one or both of the phenol rings.

I. Syntheses of Ligand Precursors from a Methylaminoethylamine Skeleton:

A general synthetic pathway of preparing Salalen ligand precursors from a methylaminoethylamine skeleton is presented in Scheme 2 below.

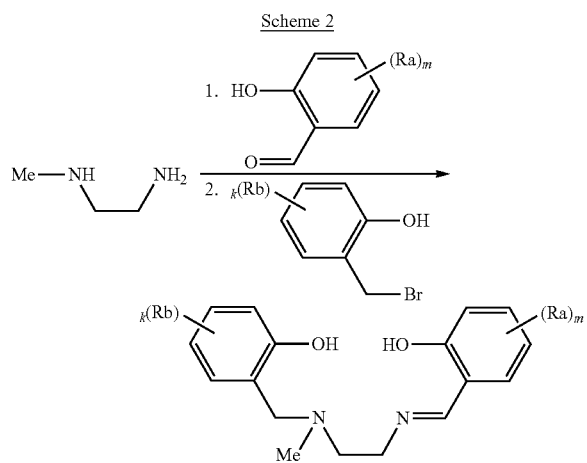

N-Methylethylenediamine (1 molequivalent) is added to a solution of a substituted 2-hydroxy-benzaldehyde in an organic non-polar solvent (e.g., benzene) and the reaction mixture is refluxed for 2 hours. The solvent is thereafter removed under vacuum, yielding a solid residue (>90% yield). The obtained substituted 2-((methylamino)ethylimino)methyl)phenol is dissolved in THF, triethylamine as an exemplary base is added, and to the obtained solution a solution of a substituted 2-(bromomethyl)phenol (1 molequivalent) in THF is added dropwise and the reaction mixture is stirred for 2 hours. The formed solid is thereafter filtered out and the solvent is removed under vacuum. The crude product can be re-crystallized from a cold solvent (e.g., methanol) yielding the respective ligand precursor as a solid, typically in about quantitative yield. Typically, no further purification steps are required.

In a typical general procedure, ligand precursors having the following general Formula IA were prepared:

Formula IA

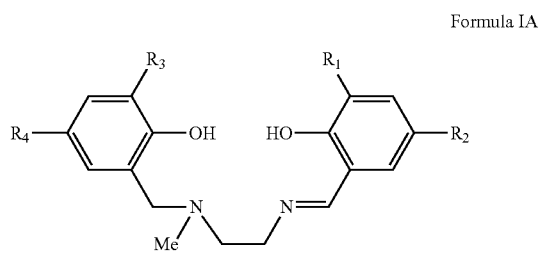

such that "m" in scheme 2 above is 2; Ra denotes the substituents $R_1$ and $R_2$; and Rb denotes the substituents $R_3$ and $R_4$.

Using the above-described general procedure (see, Scheme 2), Salalen ligand precursors referred to herein as $Lig^{1-12}H_2$ were prepared, as representative ligand precursors having a (methylamino)ethylimino bridging unit. These ligands are all characterized by one or more bulky groups on the phenol proximal to the imine nitrogen (e.g., $R_1$ and $R_2$ in the above general Formula 1A), except for $Lig^7H_2$ synthesized and studied for comparison. The chemical structures of $Lig^{1-12}H_2$ are presented in FIG. 1.

The structure of all intermediates and final products was verified by NMR measurements and in some cases also by elemental analysis.

The following describes in detail the procedures used for preparing exemplary such ligand precursors.

Syntheses of $Lig^1H_2$ ($R_1=R_2=$t-Bu; $R_3=R_4=$Cl in Formula IA); $Lig^2H_2$ ($R_1=R_2=$t-Bu; $R_3=R_4=$Br in Formula IA); and $Lig^3H_2$ ($R_1=R_2=$t-Bu; $R_3=R_4=$I in Formula IA):

Synthesis of 2-hydroxy-3,5-dibromobenzenemethanol: To a stirred solution of 3,5-dibromosalicylaldehyde (10.6 grams, 38 mmol) in MeOH (70 mL), was added $NaBH_4$ (4.3 grams, 115 mmol) in small portions and the solution was stirred for 1.5 hours. Another batch of $NaBH_4$ (2.0 grams, 52 mmol) was added in small portions and the mixture was stirred for another 2 hours. The solvent was removed under vacuum and the resulting white solid was re-precipitated in water. The product was collected as a white solid by vacuum filtration (10.1 grams, 94% yield).

$^1$H NMR ($CDCl_3$): δ=7.41 (d, J=2.3 Hz, 1H), 7.30 (d, J=2.3 Hz, 1H), 5.81 (s, 1H), 4.78 (d, J=5.7 Hz, 1H).

Synthesis of 2-(bromomethyl)-4,6-dibromophenol: To 2-(hydroxymethyl)-4,6-dibromophenol (9.0 grams, 31.9 mmol) was added 120 mL of HBr (33% solution in acetic acid) and 5 mL of concentrated $H_2SO_4$ solution. The flask was heated to 80° C. and allowed to stir overnight. The flask was cooled to room temperature and a white precipitate formed. The white solid was collected by vacuum filtration and was washed with cold water (9.2 grams, 84% yield).

$^1$H NMR ($CDCl_3$) δ 7.57 (d, J=2.2 Hz, 1H), 7.41 (d, J=2.2 Hz, 1H), 5.82 (s, 1H), 4.50 (s, 1H); $^{13}$C NMR δ 152.4 (CO), 141.4 (CH), 140.9 (CH), 135.7 (C), 121.8 (C), 118.7 (C), 27.1 ($CH_2$).

Synthesis of the ligand precursor $Lig^1H_2$: A solution of 2-(bromomethyl)-4,6-dichlorophenol (0.44 gram, 1.7 mmol) in THF (20 mL) was added dropwise to a solution of 2-((methylamino)ethylimino)methyl)-4,6-di-tert-butylphenol (0.50 gram, 1.7 mmol) and triethylamine (3 mL) in THF (20 mL) and the reaction mixture was stirred for 2 hours. The formed solid was filtered out and the solvent was removed under vacuum. The crude product was re-crystallized from cold methanol yielding the ligand precursor $Lig^1H_2$ as a yellow solid quantitatively.

$^1$H NMR ($CDCl_3$, 400 MHz): δ=8.39 (s, 1H, NCH), 7.39 (d, 1H, J=2.1 Hz, ArH), 7.24 (d, 1H, J=2.2 Hz, ArH), 7.08 (d, 1H, J=2.1 Hz, ArH), 6.86 (d, 1H, J=2.2 Hz, ArH), 3.77 (t, 2H, J=6.7 Hz, $NCH_2$), 3.76 (s, 2H, $ArCH_2N$), 2.88 (t, 2H, J=6.7 Hz, $NCH_2$), 2.40 (s, 3H, $NCH_3$), 1.43 (s, 9H, $C(CH_3)_3$), 1.31 (s, 9H, $C(CH_3)_3$).

$^{13}$C NMR ($CDCl_3$, 100.67 MHz): δ=168.4 (CN), 158.6 (CO), 153.5 (CO), 140.9 (C), 137.4 (C), 129.5 (CH), 128.0 (CH), 127.3 (CH), 126.8 (CH), 124.4 (C), 124.1 (C), 122.3 (C), 118.4 (C), 61.8 ($CH_2$), 58.1 ($CH_2$), 57.8 ($CH_2$), 42.7 ($NCH_3$), 35.7 (C), 34.8 (C), 32.2 ($C(CH_3)_3$), 30.1 ($C(CH_3)_3$).

MS (FAB): Calc for $C_{25}H_{34}N_2O_2Cl_2$: 464.2. found: 465.1 ($MH^+$).

Anal. Calcd for $C_{25}H_{34}N_2Cl_2O_2$: C, 64.51; H, 7.36; N, 6.02. Found: C, 64.56; H, 7.26; N, 6.16.

Synthesis of the ligand precursor $Lig^2H_2$: A solution of 2-(bromomethyl)-4,6-dibromophenol (1.36 gram, 3.9 mmol) in THF (20 mL) was added dropwise to a solution of 2-((methylamino)ethylimino)methyl)-4,6-di-tert-butylphenol (1.14 gram, 3.9 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor Lig²H₂ as a yellow solid quantitatively.

¹H NMR (CDCl₃, 400 MHz): δ=8.39 (s, 1H, NCH), 7.53 (d, 1H, J=2.2 Hz, ArH), 7.39 (d, 1H, J=2.4 Hz, ArH), 7.09 (d, 1H, J=2.4 Hz, ArH), 7.05 (d, 1H, J=2.2 Hz, ArH), 3.79 (t, 2H, J=6.7 Hz, NCH₂), 3.77 (s, 2H, ArCH₂N), 2.89 (t, 2H, J=6.7 Hz, NCH₂), 2.41 (s, 3H, NCH₃), 1.44 (s, 9H, C(CH₃)₃), 1.30 (s, 9H, C(CH₃)₃).

¹³C NMR (CDCl₃, 100.67 MHz): δ=167.8 (CN), 157.9 (CO), 154.3 (CO), 140.3 (C), 136.7 (C), 134.2 (CH), 130.2 (CH), 126.9 (CH), 125.8 (CH), 124.3 (C), 117.7 (C), 111.1 (C), 110.6 (C), 61.0 (CH₂), 57.4 (CH₂), 57.1 (CH₂), 41.9 (NCH₃), 35.1 (C), 34.2 (C), 31.6 (C(CH₃)₃), 29.5 (C(CH₃)₃).

Anal. Calcd for $C_{25}H_{34}N_2Br_2O_2$: C, 54.16; H, 6.18; N, 5.05. Found: C, 53.20; H, 5.79; N, 5.01.

Synthesis of the ligand precursor Lig³H₂: A solution of 2-(bromomethyl)-4,6-diiodophenol (0.94 gram, 2.1 mmol) in THF (20 mL) was added dropwise to a solution of 2-((methylamino)ethylimino)methyl)-4,6-di-tert-butylphenol (0.62 gram, 2.1 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor Lig³H₂ as a yellow solid quantitatively.

¹H NMR (CDCl₃, 400 MHz): δ=8.37 (s, 1H, NCH), 7.89 (d, 1H, J=2.2 Hz, ArH), 7.39 (d, 1H, J=2.4 Hz, ArH), 7.20 (d, 1H, J=2.4 Hz, ArH), 7.09 (d, 1H, J=2.2 Hz, ArH), 3.74 (t, 2H, J=7.6 Hz, NCH₂), 3.68 (s, 2H, ArCH₂N), 2.85 (t, 2H, J=7.6 Hz, NCH₂), 2.36 (s, 3H, NCH₃), 1.45 (s, 9H, C(CH₃)₃), 1.31 (s, 9H, C(CH₃)₃).

¹³C NMR (CDCl₃, 100.67 MHz): δ=167.8 (CN), 157.9 (CO), 157.4 (CO), 145.3 (CH), 140.3 (C), 136.9 (CH), 136.7 (C), 127.3 (CH), 126.2 (CH), 123.9 (C), 117.7 (C), 86.3 (C), 80.8 (C), 60.8 (CH₂), 57.4 (CH₂), 57.1 (CH₂), 41.9 (NCH₃), 35.1 (C), 34.2 (C), 31.6 (C(CH₃)₃), 29.6 (C(CH₃)₃).

Anal. Calcd for $C_{25}H_{34}N_2I_2O_2$: C, 46.31; H, 5.29; N, 4.32. Found: C, 47.04; H, 5.28; N, 4.43.

Syntheses of Lig⁴H₂ (R₁=Adamantyl, R₂=Me; R₃=R₄=Cl in Formula IA); Lig⁵H₂ (R₁=Adamantyl, R₂=Me; R₃=R₄=Br in Formula IA); and Lig⁶H₂ (R₁=Adamantyl, R₂=Me; R₃=R₄=I in Formula IA):

Synthesis of 2-((methylamino)ethylimino)methyl)-4-methyl-6-adamantylphenol: N-Methylethylenediamine (0.56 gram, 7.6 mmol) was added to a solution of 3-Adamantyl-2-hydroxy-5-methylbenzaldehyde (2.06 gram, 7.6 mmol) in benzene and refluxed for 2 hours. The solvent was removed under vacuum yielding a yellow solid (2.41 grams, 97%).

¹H NMR (CDCl₃, 400 MHz): δ=8.32 (s, 1H, NCH), 7.07 (d, 1H, J=2.0 Hz ArH), 6.88 (d, 1H, J=2.0 Hz ArH), 3.69 (t, 2H, J=5.9 Hz, NCH₂), 2.90 (t, 2H, J=5.9 Hz, NCH₂), 2.46 (s, 3H, NCH₃), 2.27 (s, 3H, ArCH₃), 2.16 (bs, 6H, Adamantyl), 2.07 (bs, 3H, Adamantyl), 1.78 (m, 6H, Adamantyl).

¹³C NMR (CDCl₃, 100.67 MHz): δ=167.7 (CN), 159.1 (CO), 138.1 (C), 131.2 (CH), 130.2 (CH), 127.4 (C), 119.0 (C), 60.2 (CH₂), 52.6 (CH₂), 41.0 (NCH₃), 37.9 (CH₂), 37.6 (CH₂), 37.0 (C), 29.8 (ArCH₃), 21.4 (CH).

Synthesis of the Ligand Precursor: A solution of 2-(bromomethyl)-4,6-dihalophenol [1.12 gram, 2.5 mmol, of 2-(bromomethyl)-4,6-diiodophenol for Lig⁶H₂ or a molequivalent amount of 2-(bromomethyl)-4,6-dichlorophenol for Lig⁴H₂ or 2-(bromomethyl)-4,6-dibromophenol for Lig⁵H₂] in THF (20 mL) was added dropwise to a solution of 2-((methylamino)ethylimino)methyl)-4-methyl-6-adamantylphenol (0.83 gram, 2.5 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor as a bright yellow solid in quantitative yield. No further purification steps were required.

The following presents the analytical data for Lig⁶H₂:

¹H NMR (CDCl₃, 400 MHz): δ=8.32 (s, 1H, NCH), 7.91 (d, 1H, J=2.1 Hz, ArH), 7.22 (d, 1H, J=2.0 Hz, ArH), 7.07 (d, 1H, J=2.1 Hz, ArH), 6.89 (d, 1H, J=2.0 Hz, ArH), 3.78 (t, 2H, J=6.6 Hz, NCH₂), 3.71 (s, 2H, ArCH₂N), 2.88 (t, 2H, J=6.6 Hz, NCH₂), 2.39 (s, 3H, NCH₃), 2.27 (s, 3H, ArCH₃), 2.17 (bs, 6H, Adamantyl), 2.07 (bs, 3H, Adamantyl), 1.78 (m, 6H, Adamantyl).

¹³C NMR (CDCl₃, 100.67 MHz): δ=167.5 (CN), 158.2 (CO), 157.4 (CO), 145.3 (CH), 137.5 (C), 136.9 (CH), 130.9 (CH), 129.6 (CH), 126.9 (C), 123.8 (C), 118.2 (C), 86.2 (C), 80.6 (C), 60.9 (CH₂), 57.3 (CH₂), 57.1 (CH₂), 41.9 (NCH₃), 40.3 (CH₂), 37.2 (CH₂), 36.9 (C), 29.1 (ArCH₃), 20.7 (CH).

Elemental analysis calculated for $C_{28}H_{34}N_2I_2O_2$: C, 49.14; H, 5.01; N, 4.09. Found: C, 49.04; H, 4.86; N, 4.20.

The following presents the analytical data for Lig⁴H₂:

¹H NMR (CDCl₃, 400 MHz): δ=8.33 (s, 1H, NCH), 7.24 (d, 1H, J=1.5 Hz, ArH), 7.08 (d, 1H, J=2.5 Hz, ArH), 6.89 (d, 1H, J=1.5 Hz, ArH), 6.86 (d, 1H, J=1.5 Hz, ArH), 3.77 (t, 2H, J=6.9 Hz, NCH₂), 3.76 (s, 2H, ArCH₂N), 2.89 (t, 2H, J=6.9 Hz, NCH₂), 2.40 (s, 3H, NCH₃), 2.27 (s, 3H, ArCH₃), 2.16 (bs, 6H, Adamantyl), 2.07 (bs, 3H, Adamantyl), 1.78 (m, 6H, Adamantyl).

¹³C NMR (CDCl₃, 100.67 MHz): δ=167.4 (CN), 158.6 (CO), 157.9 (CO), 137.4 (CH), 130.9 (C), 129.6 (CH), 128.8 (CH), 126.9 (CH), 126.6 (C), 123.7 (C), 123.4 (C), 121.7 (C), 118.2 (C), 61.1 (CH₂), 57.3 (CH₂), 57.2 (CH₂), 42.0 (NCH₃), 40.3 (CH₂), 37.2 (CH₂), 36.9 (C), 29.1 (ArCH₃), 20.7 (CH).

The following presents the analytical data for Lig⁵H₂:

¹H NMR (CDCl₃, 400 MHz): δ=8.33 (s, 1H, NCH), 7.54 (d, 1H, J=2.2 Hz, ArH), 7.08 (d, 1H, J=1.8 Hz, ArH), 7.02 (d, 1H, J=2.5 Hz, ArH), 6.88 (d, 1H, J=1.8 Hz, ArH), 3.78 (t, 2H, J=6.8 Hz, NCH₂), 3.71 (s, 2H, ArCH₂N), 2.86 (t, 2H, J=6.8 Hz, NCH₂), 2.38 (s, 3H, NCH₃), 2.30 (s, 3H, ArCH₃), 2.22 (bs, 6H, Adamantyl), 2.15 (bs, 3H, Adamantyl), 1.77 (m, 6H, Adamantyl).

¹³C NMR (CDCl₃, 100.67 MHz): δ=167.3 (CN), 158.1 (CO), 154.1 (CO), 137.3 (CH), 134.1 (C), 130.7 (CH), 130.0 (CH), 129.5 (CH), 126.8 (C), 124.0 (C), 118.1 (C), 110.9 (C), 110.4 (C), 60.9 (CH₂), 57.1 (CH₂), 57.0 (CH₂), 41.7 (NCH₃), 40.2 (CH₂), 37.1 (CH₂), 36.8 (C), 29.0 (ArCH₃), 20.6 (CH).

Synthesis of Lig⁷H₂ (R₁=R₂=H; R₃=R₄=I in Formula IA):

Synthesis of 2-((methylamino)ethylimino)methyl)-phenol: N-Methylethylenediamine (3.91 grams, 52.7 mmol) was added to a solution of salicylaldehyde (6.44 grams, 52.7 mmol) in benzene and the reaction mixture was refluxed for 2 hours. The solvent was thereafter evaporated yielding yellow oil 9.1 grams, 98%).

¹H NMR (CDCl₃, 400 MHz): δ=8.21 (s, 1H, NCH), 7.21-7.08 (m, 2H, ArH), 6.79-6.71 (m, 2H, ArH), 3.28 (t, 2H, J=5.1 Hz, NCH₂), 2.74 (t, 2H, J=5.1 Hz, NCH₂), 2.14 (s, 3H, NCH₃).

¹³C NMR (CDCl₃, 100.67 MHz): δ=168.7 (CN), 161.2 (CO), 132.9 (CH), 131.9 (CH), 130.5 (CH), 119.3 (CH), 117.6 (CH), 60.1 (CH₂), 52.5 (CH₂), 36.9 (NCH₃).

Synthesis of the ligand precursor Lig⁷H₂: A solution of 2-(bromomethyl)-4,6-diiodophenol (1.77 gram, 4.0 mmol) in THF (20 mL) was added dropwise to a solution of 2-((methylamino)ethylimino)methyl)-phenol (0.72 gram, 4.0 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor Lig$^7$H$_2$ as a yellow solid quantitatively.

$^1$H NMR (CDCl$_3$, 400 MHz): δ=8.36 (s, 1H, NCH), 7.90 (d, 1H, J=2.2 Hz, ArH), 7.33-7.25 (m, 2H, ArH), 7.22 (d, 1H, J=2.2 Hz, ArH), 6.96 (d, 1H, J=8.3 Hz, ArH), 6.88 (t, 1H, J=7.6 Hz, ArH), 3.78 (t, 2H, J=6.4 Hz, NCH$_2$), 3.70 (s, 2H, ArCH$_2$N), 2.87 (t, 2H, J=6.4 Hz, NCH$_2$), 2.39 (s, 3H, NCH$_3$).

$^{13}$C NMR (CDCl$_3$, 100.67 MHz): δ=166.7 (CN), 160.9 (CO), 157.3 (CO), 145.3 (CH), 136.9 (CH), 132.6 (CH), 130.9 (CH), 123.9 (C), 119.2 (CH), 118.7 (C), 117.1 (CH), 86.3 (C), 80.8 (C), 60.8 (CH$_2$), 57.2 (2CH$_2$), 42.0 (NCH$_3$).

Anal. Calcd for C$_{17}$H$_{18}$N$_2$I$_2$O$_2$: C, 38.08; H, 3.38; N, 5.22. Found: C, 37.10; H, 3.17; N, 5.51.

Synthesis of Lig$^8$H$_2$ (R$_1$=R$_2$=2-phenylpropyl; R$_3$=R$_4$=Br in Formula IA):

A solution of 2-(bromomethyl)-4,6-dibromophenol (0.49 gram, 1.4 mmol) in THF (20 mL) was added dropwise to a solution of 2-((methylamino)ethylimino)methyl)-4,6-di-2-phenylpropyl (0.59 gram, 1.4 mmol) and triethylamine (3 mL) in THF (20 mL) and the reaction mixture was stirred for 2 hours. The formed solid was filtered out and the solvent was removed under vacuum. The crude product was re-crystallized from cold methanol yielding the ligand precursor Lig$^8$H$_2$ as a yellow solid quantitatively.

$^1$H NMR (CDCl$_3$, 400 MHz): δ=8.39 (s, 1H, NCH), 7.38 (d, 1H, J=2.5 Hz, ArH), 7.32-7.25 (m, 10H, ArH), 7.24 (d, 1H, J=2.5 Hz, ArH), 7.08 (d, 1H, J=2.0 Hz, ArH), 6.87 (d, 1H, J=2.0 Hz, ArH), 3.81 (t, 2H, J=6.6 Hz, NCH$_2$), 3.70 (s, 2H, ArCH$_2$N), 2.92 (t, 2H, J=6.6 Hz, NCH$_2$), 2.40 (s, 3H, NCH$_3$), 1.63 (s, 6H, C(CH$_3$)$_2$), 1.59 (s, 6H, C(CH$_3$)$_2$).

Synthesis of Lig$^9$H$_2$ (R$_1$=triphenylmethyl, R$_2$=Me; R$_3$=R$_4$=I in Formula IA):

A solution of 2-(bromomethyl)-4,6-diiodophenol (0.61 gram, 1.4 mmol) in THF (20 mL) was added dropwise to a solution of 2-((methylamino)ethylimino)methyl)-4-triphenyl-6-methylphenol (0.61 gram, 1.4 mmol) and triethylamine (3 mL) in THF (20 mL) and the reaction mixture was stirred for 2 hours. The formed solid was filtered out and the solvent was removed under vacuum. The crude product was re-crystallized from cold methanol yielding the ligand precursor Lig$^9$H$_2$ as a yellow solid quantitatively.

$^1$H NMR (CDCl$_3$, 400 MHz): δ=8.27 (s, 1H, NCH), 7.83 (d, 1H, J=2.1 Hz, ArH), 7.33 (d, 1H, J=2.0 Hz, ArH), 7.31-7.13 (m, 15H, ArH), 7.01 (d, 1H, J=2.1 Hz, ArH), 6.87 (d, 1H, J=2.0 Hz, ArH), 3.80 (t, 2H, J=6.7 Hz, NCH$_2$), 3.75 (s, 2H, ArCH$_2$N), 2.87 (t, 2H, J=6.7 Hz, NCH$_2$), 2.39 (s, 3H, NCH$_3$), 2.24 (s, 3H, ArCH$_3$).

Synthesis of Lig$^{19}$H$_2$ (R$_1$=adamantyl, R$_2$=Me; R$_3$=adamantyl, R$_4$=Me in Formula IA):

A solution of 2-(bromomethyl)-4-adamantyl-6-methylphenol (0.41 gram, 1.2 mmol) in THF (20 mL) was added dropwise to a solution of 2-((methylamino)ethylimino)methyl)-4-methyl-6-adamantylphenol (0.40 gram, 1.2 mmol) and triethylamine (3 mL) in THF (20 mL) and the reaction mixture was stirred for 2 hours. The formed solid was filtered out and the solvent was removed under vacuum. The crude product was re-crystallized from cold methanol yielding the ligand precursor Lig$^{10}$H$_2$ as a yellow solid quantitatively.

$^1$H NMR (CDCl$_3$, 400 MHz): δ=8.29 (s, 1H, NCH), 7.61 (d, 1H, J=1.6 Hz, ArH), 7.21 (d, 1H, J=1.6 Hz, ArH), 6.94 (d, 1H, J=1.6 Hz, ArH), 6.73 (d, 1H, J=1.6 Hz, ArH), 3.80 (t, 2H, J=6.9 Hz, NCH$_2$), 3.76 (s, 2H, ArCH$_2$N), 2.88 (t, 2H, J=6.9 Hz, NCH$_2$), 2.40 (s, 3H, NCH$_3$), 2.27 (s, 3H, ArCH$_3$), 2.25 (s, 3H, ArCH$_3$), 2.18-2.12 (bs, 12H, Adamantyl), 2.10-2.05 (bs, 6H, Adamantyl), 1.81-1.73 (m, 12H, Adamantyl).

Synthesis of Lig$^{11}$H$_2$ (R$_1$=adamantyl, R$_2$=Me; R$_3$=R$_4$=t-Bu in Formula IA):

A solution of 2-(bromomethyl)-4,6-ditertbutylphenol (0.28 gram, 1.0 mmol) in THF (20 mL) was added dropwise to a solution of 2-((methylamino)ethylimino)methyl)-4-methyl-6-adamantylphenol (0.31 gram, 1.0 mmol) and triethylamine (3 mL) in THF (20 mL) and the reaction mixture was stirred for 2 hours. The formed solid was filtered out and the solvent was removed under vacuum. The crude product was re-crystallized from cold methanol yielding the ligand precursor Lig$^{11}$H$_2$ as a yellow solid quantitatively.

$^1$H NMR (CDCl$_3$, 400 MHz): δ=8.37 (s, 1H, NCH), 7.88 (d, 1H, J=1.8 Hz, ArH), 7.11 (d, 1H, J=1.8 Hz, ArH), 6.95 (d, 1H, J=1.2 Hz, ArH), 6.65 (d, 1H, J=1.2 Hz, ArH), 3.71 (t, 2H, J=6.3 Hz, NCH$_2$), 3.64 (s, 2H, ArCH$_2$N), 2.74 (t, 2H, J=6.3 Hz, NCH$_2$), 2.36 (s, 3H, NCH$_3$), 2.26 (s, 3H, ArCH$_3$), 2.07 (bs, 6H, Adamantyl), 2.02 (bs, 3H, Adamantyl), 1.79 (s, 9H, C(CH$_3$)$_3$), 1.75 (m, 6H, Adamantyl), 1.51 (s, 9H, C(CH$_3$)$_3$).

Synthesis of Lig$^{12}$H$_2$ (R$_1$=adamantyl, R$_2$=Me; R$_3$=Me, R$_4$=Cl in Formula IA):

A solution of 2-((methylamino)ethylimino)methyl)-4-methyl-6-adamantylphenol (0.43 gram, 1.3 mmol), 2-methyl-4-chlorophenol (0.19 gram, 1.3 mmol), formaldehyde (water solution, 37%) (0.10 gram, 1.3 mmol) in methanol solution refluxed for 10 hours. The formed solid was filtered and the crude product was re-crystallized from cold methanol yielding the ligand precursor Lig$^{12}$H$_2$ as a yellow solid quantitatively.

$^1$H NMR (CDCl$_3$, 400 MHz): δ=8.31 (s, 1H, NCH), 7.08 (d, 1H, J=2.0 Hz, ArH), 7.00 (d, 1H, J=2.0 Hz, ArH), 6.88 (d, 1H, J=1.4 Hz, ArH), 6.79 (d, 1H, J=1.4 Hz, ArH), 3.75 (t, 2H, J=6.4 Hz, NCH$_2$), 3.70 (s, 2H, ArCH$_2$N), 2.85 (t, 2H, J=6.4 Hz, NCH$_2$), 2.38 (s, 3H, NCH$_3$), 2.28 (s, 3H, ArCH$_3$), 2.16 (bs, 6H, Adamantyl), 2.07 (bs, 3H, Adamantyl), 2.14 (s, 3H, ArCH$_3$), 1.78 (m, 6H, Adamantyl).

$^{13}$C NMR (CDCl$_3$, 100.67 MHz): δ=167.8 (CN), 158.9 (CO), 155.3 (CO), 138.1 (CH), 136.2 (C), 131.4 (CH), 130.2 (CH), 127.6 (CH), 127.5 (C), 126.3 (C), 123.6 (C), 122.9 (C), 118.9 (C), 61.9 (CH$_2$), 57.9 (CH$_2$), 42.6 (CH$_2$), 41.0 (NCH$_3$), 37.7 (CH$_2$), 37.6 (C), 29.8 (CH$_3$), 21.4 (CH), 16.2 (CH$_3$).

Using the above-described general procedure (see, Scheme 2), exemplary Salalen ligand precursors referred to herein as Lig$^{18-20}$H$_2$ were prepared, as additional representative ligand precursors having a (methylamino)ethylimino skeleton. These ligands are characterized by electron withdrawing groups (halo-substituents) on the phenol arm proximal to the imine nitrogen (e.g., R$_1$ and R$_2$ in the above general Formula IA), and bulky groups on the phenol arm proximal to the amine nitrogen (e.g., R$_3$ and R$_4$ in the above general Formula IA). The chemical structures of Lig$^{18-20}$H$_2$ are presented in FIG. 2.

Syntheses of Lig$^{18}$H$_2$ (R$_1$=R$_2$=Cl; R$_3$=adamantyl, R$_4$=Me), of Lig$^{19}$H$_2$ (R$_1$=R$_2$=Br; R$_3$=adamantyl, R$_4$=Me) and of Lig$^{18}$H$_2$ (R$_1$=R$_2$=I; R$_3$=adamantyl, R$_4$=Me):

Synthesis of 2-((methylamino)ethylimino)methyl)-3,5-dihalophenol: N-Methylethylenediamine (1.50 gram, 20.2 mmol) was added to a solution of 3,5-dichlorosalicylaldehyde (3.86 grams, 20.2 mmol, for Lig$^{18}$H$_2$, or of equimolar amount of 3,5-dibromosalicylaldehyde for Lig$^{19}$H$_2$ and of 3,5-diiodosalicylaldehyde for Lig$^{20}$H$_2$) in ethanol and the reaction mixture was stirred for 2 hours. The solvent was thereafter removed under vacuum yielding an orange solid (4.92 grams, 99%). The following presents the analytical data obtained for 2-((methylamino)ethylimino)methyl)-3,5-dichlorophenol, as an example:

¹H NMR (CDCl₃, 200 MHz): δ=7.35 (d, 1H, J=2.6 Hz, ArH), 7.09 (d, 1H, J=2.6 Hz, ArH), 3.46 (m, 2H, NCH₂), 2.95 (m, 2H, NCH₂), 2.43 (s, 3H, NCH₃).

Synthesis of the Ligand Precursor: A solution of 2-(bromomethyl)-4-methyl-6-adamantylphenol (0.47 gram, 1.4 mmol) in THF (20 mL) was added dropwise to a solution of 2-((methylamino)ethylimino)methyl)-4,6-dichlorophenol (0.35 gram, 1.4 mmol, or an equimolar amount of the respective dibromophenol or diiodophenol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor as a bright yellow solid in quantitative yield. No further purification steps were required.

The following presents the analytical data of Lig¹⁸H₂:

¹H NMR (CDCl₃, 400 MHz): δ=8.27 (s, 1H, NCH), 7.40 (d, 1H, J=2.5 Hz, ArH), 7.14 (d, 1H, J=2.5 Hz, ArH), 6.90 (d, 1H, J=1.7 Hz, ArH), 6.63 (d, 1H, J=1.7 Hz, ArH), 3.80 (t, 2H, J=5.9 Hz, NCH₂), 3.67 (s, 2H, ArCH₂N), 2.83 (t, 2H, J=5.9 Hz, NCH₂), 2.35 (s, 3H, NCH₃), 2.22 (s, 3H, ArCH₃), 2.02 (bs, 6H, Adamantyl), 1.99 (bs, 3H, Adamantyl), 1.70 (m, 6H, Adamantyl).

¹³C NMR (CDCl₃, 100.67 MHz): δ=167.8 (CN), 158.6 (CO), 157.0 (CO), 135.7 (C), 132.3 (CH), 129.1 (CH), 127.3 (C), 126.9 (CH), 126.7 (CH), 122.7 (C), 122.6 (C), 121.4 (C), 119.5 (C), 61.4 (CH₂), 56.8 (CH₂), 56.5 (CH₂), 42.2 (NCH₃), 40.3 (CH₂), 37.1 (CH₂), 36.7 (C), 29.1 (ArCH₃), 20.8 (CH).

The following presents the analytical data of Lig¹⁹H₂:

¹H NMR (CDCl₃, 400 MHz): δ=8.23 (s, 1H, NCH), 7.69 (d, 1H, J=2.4 Hz, ArH), 7.32 (d, 1H, J=2.4 Hz, ArH), 6.90 (d, 1H, J=1.8 Hz, ArH), 6.62 (d, 1H, J=1.8 Hz, ArH), 3.75 (t, 2H, J=5.8 Hz, NCH₂), 3.61 (s, 2H, ArCH₂N), 2.84 (t, 2H, J=5.8 Hz, NCH₂), 2.39 (s, 3H, NCH₃), 2.20 (s, 3H, ArCH₃), 2.00 (bs, 6H, Adamantyl), 1.76 (bs, 3H, Adamantyl), 1.48 (m, 6H, Adamantyl).

The following presents the analytical data of Lig²⁰H₂:

¹H NMR (CDCl₃, 400 MHz): δ=8.13 (s, 1H, NCH), 8.01 (d, 1H, J=2.0 Hz, ArH), 7.49 (d, 1H, J=2.0 Hz, ArH), 6.90 (d, 1H, J=1.4 Hz, ArH), 6.51 (d, 1H, J=1.4 Hz, ArH), 3.78 (t, 2H, J=6.1 Hz, NCH₂), 3.66 (s, 2H, ArCH₂N), 2.82 (t, 2H, J=6.1 Hz, NCH₂), 2.34 (s, 3H, NCH₃), 2.22 (s, 3H, ArCH₃), 2.02 (bs, 6H, Adamantyl), 1.71 (bs, 3H, Adamantyl), 1.54 (m, 6H, Adamantyl).

¹³C NMR (CDCl₃, 100.67 MHz): δ=164.5 (CN), 161.2 (CO), 154.5 (CO), 148.7 (C), 139.8 (CH), 139.6 (CH), 136.7 (C), 127.3 (CH), 126.9 (CH), 126.7 (C), 121.4 (C), 121.2 (C), 119.8 (C), 61.5 (CH₂), 57.2 (CH₂), 56.1 (CH₂), 42.2 (NCH₃), 40.5 (CH₂), 37.3 (CH₂), 36.7 (C), 29.1 (CH₃), 20.8 (CH).

Using the above-described general procedure (see, Scheme 2), exemplary Salalen ligand precursors referred to herein as Lig²¹⁻²⁵H₂ were prepared, as additional representative ligand precursors having a (methylamino)ethylimino skeleton. These ligands are characterized by electron withdrawing groups (halo-substituents) on both phenol arms (e.g., $R_1$-$R_4$ in the above general Formula 1A). The chemical structures of Lig²¹⁻²⁵H₂ are presented in FIG. 3.

The synthesis of Lig²¹H₂ ($R_1$=$R_2$=$R_3$=$R_4$=Cl) is provided herein in detail as an exemplary procedure. Replacing the chloro substituents on the salicylaldehyde by bromo or iodo and/or replacing the chloro substituents on the 2-(bromomethyl)-4-6-dichlorophenol by bromo or iodo yielded the other ligand precursors of this type.

Synthesis of 2-((methylamino)ethylimino)methyl)-3,5-dichlorolphenol: N-Methylethylenediamine (1.50 gram, 20.2 mmol) was added to a solution of 3,5-dichlorosalicylaldehyde (3.86 grams, 20.2 mmol) in ethanol and the reaction mixture was stirred for 2 hours. The solvent was thereafter removed under vacuum yielding an orange solid (4.92 grams, 99%).

¹H NMR (CDCl₃, 200 MHz): δ=7.35 (d, 1H, J=2.6 Hz, ArH), 7.09 (d, 1H, J=2.6 Hz, ArH), 3.46 (m, 2H, NCH₂), 2.95 (m, 2H, NCH₂), 2.43 (s, 3H, NCH₃).

Synthesis of the Ligand Precursor: A solution of 2-(bromomethyl)-4-6-dichlorophenol (1.39 gram, 5.5 mmol) in THF (20 mL) was added dropwise to a solution of 2-((methylamino)ethylimino)methyl)-4,6-chlorophenol (1.35 gram, 1.4 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor Lig²¹H₂ as a bright orange solid in quantitative yield. No further purification steps were required.

¹H NMR (CDCl₃, 400 MHz): δ=8.16 (s, 1H, NCH), 7.79 (d, 1H, J=2.0 Hz, ArH), 7.04 (d, 1H, J=2.0 Hz, ArH), 6.98 (d, 1H, J=2.0 Hz, ArH), 6.90 (d, 1H, J=2.0 Hz, ArH), 3.57 (t, 2H, J=6.1 Hz, NCH₂), 3.50 (s, 2H, ArCH₂N), 2.68 (t, 2H, J=6.1 Hz, NCH₂), 2.17 (s, 3H, NCH₃).

The following presents the analytical data of Lig²²H₂:

¹H NMR (CDCl₃, 400 MHz): δ=8.27 (s, 1H, NCH), 7.72 (d, 1H, J=2.4 Hz, ArH), 7.56 (d, 1H, J=2.4 Hz, ArH), 7.36 (d, 1H, J=2.4 Hz, ArH), 7.06 (d, 1H, J=2.4 Hz, ArH), 3.87 (t, 2H, J=6.4 Hz, NCH₂), 3.73 (s, 2H, ArCH₂N), 2.87 (t, 2H, J=6.4 Hz, NCH₂), 2.35 (s, 3H, NCH₃).

¹³C NMR (CDCl₃, 100.67 MHz): δ=165.0 (CN), 157.6 (CO), 154.0 (CO), 137.7 (CH), 134.3 (CH), 133.0 (CH), 130.2 (CH), 124.1 (C), 119.9 (C), 112.1 (C), 111.1 (C), 110.5 (C), 109.8 (C), 60.9 (CH₂), 56.4 (CH₂), 55.3 (CH₂), 42.1 (NCH₃).

The following presents the analytical data of Lig²³H₂:

¹H NMR (CDCl₃, 400 MHz): δ=8.15 (s, 1H, NCH), 8.05 (d, 1H, J=2.0 Hz, ArH), 7.90 (d, 1H, J=2.0 Hz, ArH), 7.55 (d, 1H, J=2.0 Hz, ArH), 7.21 (d, 1H, J=2.0 Hz, ArH), 3.80 (t, 2H, J=6.4 Hz, NCH₂), 3.68 (s, 2H, ArCH₂N), 2.87 (t, 2H, J=6.4 Hz, NCH₂), 2.39 (s, 3H, NCH₃).

¹³C NMR (CDCl₃, 100.67 MHz): δ=164.8 (CN), 156.1 (CO), 154.2 (CO), 140.5 (CH), 135.7 (CH), 133.4 (CH), 128.4 (CH), 124.8 (C), 117.9 (C), 115.0 (C), 113.1 (C), 112.5 (C), 111.2 (C), 60.8 (CH₂), 56.9 (CH₂), 55.0 (CH₂), 42.1 (NCH₃).

Anal. Calcd for $C_{17}H_{16}N_2I_4O_2$: C, 25.91; H, 2.05; N, 3.56. Found: C, 25.69; H, 1.88; N, 3.71.

The following presents the analytical data of Lig²⁴H₂:

¹H NMR (CDCl₃, 400 MHz): δ=8.13 (s, 1H, NCH), 8.01 (d, 1H, J=1.9 Hz, ArH), 7.47 (d, 1H, J=2.2 Hz, ArH), 7.22 (d, 1H, J=1.9 Hz, ArH), 6.84 (d, 1H, J=2.2 Hz, ArH), 3.78 (t, 2H, J=6.1 Hz, NCH₂), 3.71 (s, 2H, ArCH₂N), 2.84 (t, 2H, J=6.1 Hz, NCH₂), 2.37 (s, 3H, NCH₃).

¹³C NMR (CDCl₃, 100.67 MHz): δ=164.6 (CN), 160.7 (CO), 152.5 (CO), 148.7 (CH), 140.0 (CH), 129.0 (CH), 126.7 (CH), 123.8 (C), 123.4 (C), 121.6 (C), 119.8 (C), 88.7 (C), 80.6 (C), 61.0 (CH₂), 57.0 (CH₂), 56.2 (CH₂), 42.2 (NCH₃).

The following presents the analytical data of Lig²⁵H₂:

¹H NMR (CDCl₃, 400 MHz): δ=8.21 (s, 1H, NCH), 7.84 (d, 1H, J=1.9 Hz, ArH), 7.34 (d, 1H, J=2.2 Hz, ArH), 7.11 (d, 1H, J=1.9 Hz, ArH), 6.77 (d, 1H, J=2.2 Hz, ArH), 3.74 (t, 2H, J=6.0 Hz, NCH₂), 3.62 (s, 2H, ArCH₂N), 2.81 (t, 2H, J=6.0 Hz, NCH₂), 2.33 (s, 3H, NCH₃).

¹³C NMR (CDCl₃, 100.67 MHz): δ=165.2 (CN), 157.1 (CO), 156.3 (CO), 145.3 (CH), 132.3 (CH), 129.1 (CH), 128.8 (CH), 123.5 (C), 122.8 (C), 122.6 (C), 119.5 (C), 86.3 (C), 81.3 (C), 60.7 ($CH_2$), 56.4 ($CH_2$), 55.3 ($CH_2$), 42.1 ($NCH_3$).

II. Syntheses of Ligand Precursors from an N-alkylaminoethylamine Skeleton in which Alkyl is Other than Methyl:

A general synthetic pathway of preparing Salalen ligand precursors from a N-alkylaminoethylamine skeleton is presented in Scheme 3 below.

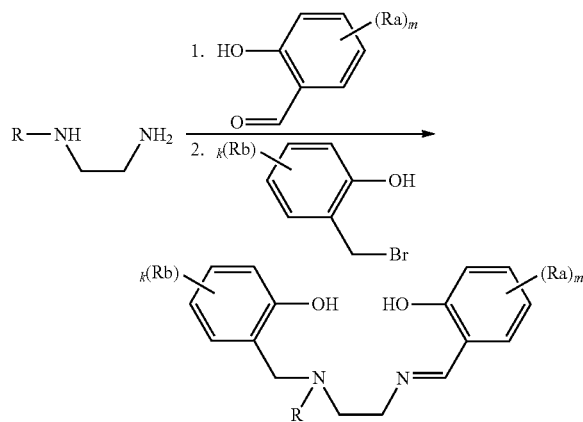

Scheme 3 wherein R is an alkyl such as, but not limited to, phenylmethyl (benzyl), ethyl and isopropyl.

N-alkylethylenediamine (1 molequivalent) is added to a solution of a substituted 2-hydroxy-benzaldehyde in an organic non-polar solvent (e.g., benzene) and the reaction mixture is refluxed for 2 hours. The solvent is thereafter removed under vacuum, yielding a solid residue (>90% yield). The obtained substituted 2-((methylamino)ethylimino)methyl)phenol is dissolved in THF, triethylamine as an exemplary base is added, and to the obtained solution a solution of a substituted 2-(bromomethyl)phenol (1 molequivalent) in THF is added dropwise and the reaction mixture is stirred for 2 hours. The formed solid is thereafter filtered out and the solvent is removed under vacuum. The crude product can be re-crystallized from a cold solvent (e.g., methanol) yielding the respective ligand precursor as a solid, typically in about quantitative yield. Typically, no further purification steps are required.

In a typical general procedure, ligand precursors having the following general Formula IB were prepared:

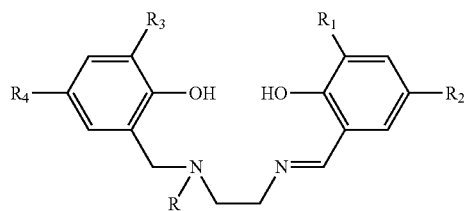

Formula IB such that "m" in scheme 2 above is 2; Ra denotes the substituents $R_1$ and $R_2$; and Rb denotes the substituents $R_3$ and $R_4$, wherein R is other than methyl.

Using the above-described general procedure (see, Scheme 3), exemplary Salalen ligand precursors referred to herein as $Lig^{13-17}H_2$ were prepared, as representative ligand precursors having a (N-alkylamino)ethylimino bridging unit. These exemplary ligands are further characterized by one or more bulky groups on the phenol proximal to the imine nitrogen (e.g., $R_1$ and $R_2$ in the above general Formula 1B) and by electron-withdrawing substituents (halo-substituents) on the other phenol arm (e.g., $R_3$ and $R_4$ in the above general Formula 1B). The chemical structures of $Lig^{13-17}H_2$ are presented in FIG. 4.

The structure of all intermediates and final products was verified by NMR measurements.

The following describes in detail the procedures used for preparing exemplary such ligand precursors.

Syntheses of $Lig^{17}H_2$ ($R_1=R_2$=t-Bu; $R_3=R_4$=Cl in Formula IB, wherein R is Formula IB is isopropyl:

Synthesis of 2-((isopropylamino)ethylimino)methyl)-3,5-tert-butylphenol: N-isopropylethylenediamine (0.65 gram, 6.4 mmol) was added to a solution of 3,5-di-tert-butyl-2-hydroxybenzaldehyde (1.49 gram, 6.4 mmol) in benzene and the reaction mixture was refluxed for 2 hours. The solvent was removed under vacuum yielding a yellow oil (2.02 grams, 100%).

$^1$H NMR ($CDCl_3$, 400 MHz): δ=8.41 (s, 1H, NCH), 7.39 (d, 1H, J=1.8 Hz, ArH), 7.10 (d, 1H, J=1.8 Hz, ArH), 3.73 (t, 2H, J=5.8 Hz, $NCH_2$), 2.94 (t, 2H, J=5.8 Hz, $NCH_2$), 2.84 (septet, 1H, J=6.2 Hz, NCH), 1.45 (s, 9H, $(CH_3)_3$), 1.31 (s, 9H, $(CH_3)_3$), 1.07 (d, 6H, J=6.2 Hz, $CH_3$).

$^{13}$C NMR ($CDCl_3$, 100.67 MHz): δ=167.0 (CN), 157.9 (CO), 139.9 (C), 128.2 (C), 126.8 (CH), 125.8 (CH), 117.7 (C), 59.8 ($CH_2$), 48.4 ($CH_2$), 47.4 (NCH), 34.9 (C), 34.0 (C), 31.4 (($CH_3)_3$), 29.3 (($CH_3)_3$), 22.7 (($CH_3)_3$).

Synthesis of the Ligand Precursor: A solution of 2-(bromomethyl)-4,6-dichlorophenol (0.90 gram, 3.5 mmol,) in THF (20 mL) was added dropwise to a solution of 2-((isopropylamino)ethylimino)methyl)-3,5-tert-butylphenol (1.13 gram, 3.5 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor as a bright yellow solid in quantitative yield. No further purification steps were required.

$^1$H NMR ($CDCl_3$, 400 MHz): δ=8.49 (s, 1H, NCH), 7.52 (d, 1H, J=1.9 Hz ArH), 7.35 (d, 1H, J=0.9 Hz ArH), 7.12 (d, 1H, J=1.9 Hz ArH), 6.95 (d, 1H, J=0.9 Hz ArH), 3.75 (t, 2H, J=5.6 Hz, $NCH_2$), 3.68 (s, 2H, $CH_2$), 2.98 (t, 2H, J=5.6 Hz, $NCH_2$), 2.72 (septet, 1H, J=6.3 Hz, NCH), 1.43 (s, 9H, $(CH_3)_3$), 1.38 (s, 9H, $(CH_3)_3$), 1.14 (d, 6H, J=6.2 Hz, $CH_3$).

Similarly, $Lig^{16}H_2$ ($R_1=R_2$=t-Bu; $R_3=R_4$=Cl in Formula IB, and R is ethyl) was prepared by reacting N-ethylethylenediamine with equimolar amount of 3,5-di-tert-butyl-2-hydroxybenzaldehyde in benzene, followed by reacting the formed intermediate with an equimolar amount of 2-(bromomethyl)-4,6-dichlorophenol in THF. Corresponding ligand precursors with different halo substituents can be similarly prepared using an equimolar amount of 2-(bromomethyl)-4,6-dibromophenol or of 2-(bromomethyl)-4,6-diiodophenol).

The following presents the analytical data for $Lig^{16}H_2$:

$^1$H NMR ($CDCl_3$, 400 MHz): δ=8.31 (s, 1H, NCH), 7.51 (d, 1H, J=2.5 Hz, ArH), 7.20 (d, 1H, J=1.6 Hz, ArH), 7.01 (d, 1H, J=1.6 Hz, ArH), 6.84 (d, 1H, J=2.5 Hz, ArH), 3.91 (quartet, 2H, $CH_2$), 3.73 (s, 2H, $CH_2$), 3.71 (t, 2H, J=6.4 Hz, $NCH_2$), 2.90 (t, 2H, J=6.4 Hz, $NCH_2$), 2.57 (t, 3H, J=1.9 Hz, $CH_3$), 1.44 (s, 9H, $(CH_3)_3$), 1.29 (s, 9H, $(CH_3)_3$).

$Lig^{13}H_2$ ($R_1=R_2$=t-Bu; $R_3=R_4$=Cl in Formula IB); $Lig^{14}H_2$ ($R_1=R_2$=t-Bu; $R_3=R_4$=Br in Formula IB); and $Lig^{15}H_2$ ($R_1=R_2$=t-Bu; $R_3=R_4$=I in Formula IB, wherein R is Formula IB is benzyl, were similarly prepared by reacting N-benzyl-ethylenediamine with equimolar amount of 3,5-di-tert-butyl-2-hydroxybenzaldehyde in benzene, followed by reacting the formed intermediate with an equimolar amount of 2-(bromomethyl)-4,6-dichlorophenol for Lig$^{13}$H$_2$, of 2-(bromomethyl)-4,6-dibromophenol for Lig$^{14}$H$_2$, and of 2-(bromomethyl)-4,6-diiodophenol for Lig$^{15}$H$_2$, in THF.

The following presents the analytical data for Lig$^{13}$H$_2$:

$^1$H NMR (CDCl$_3$, 400 MHz): δ=8.34 (s, 1H, NCH), 7.41 (d, 1H, J=2.4 Hz, ArH), 7.38-7.31 (m, 5H, ArH), 7.28 (d, 1H, J=2.2 Hz, ArH), 7.09 (d, 1H, J=2.4 Hz, ArH), 6.92 (d, 1H, J=2.2 Hz, ArH), 3.88 (s, 2H, CH$_2$), 3.78 (s, 2H, CH$_2$), 3.77 (t, 2H, J=6.8 Hz, NCH$_2$), 2.93 (t, 2H, J=6.8 Hz, NCH$_2$), 1.46 (s, 9H, (CH$_3$)$_3$), 1.33 (s, 9H, (CH$_3$)$_3$).

$^{13}$C NMR (CDCl$_3$, 100.67 MHz): δ=168.4 (CN), 164.2 (CO), 159.9 (CO), 153.2 (C), 137.4 (C), 130.2 (CH), 129.6 (CH), 128.8 (CH), 127.9 (CH), 127.5 (CH), 126.8 (C), 124.7 (CH), 118.4 (C), 59.8 (CH$_2$), 58.4 (CH$_2$), 57.6 (CH$_2$), 54.4 (CH$_2$), 35.7 (C), 34.8 (C), 32.2 ((CH$_3$)$_3$), 30.1 ((CH$_3$)$_3$).

The following presents the analytical data for Lig$^{14}$H$_2$:

$^1$H NMR (CDCl$_3$, 400 MHz): δ=8.30 (s, 1H, NCH), 7.52 (d, 1H, J=1.3 Hz, ArH), 7.38 (d, 1H, J=1.3 Hz, ArH), 7.32-7.28 (m, 5H, ArH), 7.07 (d, 1H, J=2.1 Hz, ArH), 7.05 (d, 1H, J=2.1 Hz, ArH), 3.81 (s, 2H, CH$_2$), 3.71 (s, 2H, CH$_2$), 3.70 (t, 2H, J=6.3 Hz, NCH$_2$), 2.88 (t, 2H, J=6.3 Hz, NCH$_2$), 1.44 (s, 9H, (CH$_3$)$_3$), 1.30 (s, 9H, (CH$_3$)$_3$).

$^{13}$C NMR (CDCl$_3$, 100.67 MHz): δ=167.8 (CN), 157.9 (CO), 154.0 (CO), 140.3 (C), 137.3 (C), 135.7 (CH), 129.9 (CH), 128.9 (CH), 128.5 (CH), 128.1 (CH), 127.1 (C), 126.9 (CH), 124.5 (CH), 117.7 (C), 59.0 (CH$_2$), 57.7 (CH$_2$), 56.9 (CH$_2$), 53.7 (CH$_2$), 35.1 (C), 34.2 (C), 31.6 ((CH$_3$)$_3$), 29.5 ((CH$_3$)$_3$).

The following presents the analytical data for Lig$^{15}$H$_2$:

$^1$H NMR (CDCl$_3$, 400 MHz): δ=8.29 (s, 1H, NCH), 7.89 (d, 1H, J=1.5 Hz, ArH), 7.38 (d, 1H, J=1.9 Hz, ArH), 7.31-7.21 (m, 6H, ArH), 7.07 (d, 1H, J=1.9 Hz, ArH), 3.82 (s, 2H, CH$_2$), 3.71 (s, 2H, CH$_2$), 3.70 (t, 2H, J=6.5 Hz, NCH$_2$), 2.86 (t, 2H, J=6.5 Hz, NCH$_2$), 1.45 (s, 9H, (CH$_3$)$_3$), 1.31 (s, 9H, (CH$_3$)$_3$).

$^{13}$C NMR (CDCl$_3$, 100.67 MHz): δ=168.5 (CN), 158.6 (CO), 157.8 (CO), 146.1 (C), 141.0 (C), 137.9 (CH), 137.4 (CH), 136.3 (CH), 130.3 (CH), 129.6 (CH), 128.8 (C), 128.0 (CH), 126.9 (CH), 124.9 (CH), 118.5 (C), 59.7 (CH$_2$), 58.3 (CH$_2$), 57.6 (CH$_2$), 54.3 (CH$_2$), 35.8 (C), 34.9 (C), 32.3 ((CH$_3$)$_3$), 30.3 ((CH$_3$)$_3$).

III. Syntheses of Ligand Precursors from 3-carbon Atoms Diamino Skeleton:

An exemplary general synthetic pathway of preparing Salalen ligand precursors from 3-carbon atoms diamino skeleton is presented in Scheme 4 below.

Scheme 4

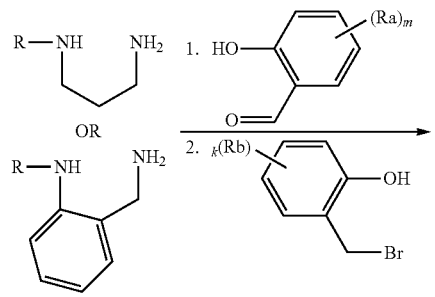

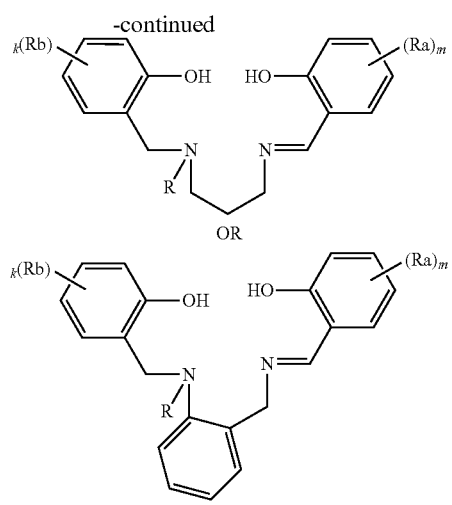

wherein R is an alkyl such as, but not limited to, methyl, benzyl, ethyl and isopropyl, and is preferably methyl.

A solution of N$^1$-alkylpropane-1,3-diamine (e.g., N$^1$-methylpropane-1,3-diamine) or of 2-amino (or alkylamino)-N-methyl-benzenemethanamine.2HCl (1 molequivalent) and triethylamine as an exemplary base in an organic solvent such as benzene is added to a solution of a substituted 2-hydroxybenzaldehyde in an organic solvent such as benzene and the reaction mixture is refluxed for e.g., 5 hours. The solution is then filtered and the solvent is removed under vacuum yielding a solid residue.

The obtained substituted 2-(iminomethyl)phenol is dissolved in THF, triethylamine as an exemplary base is added, and to the obtained solution a solution of a substituted 2-(bromomethyl)phenol (1 molequivalent) in THF is added dropwise and the reaction mixture is stirred for 2 hours. The formed solid is thereafter filtered out and the solvent is removed under vacuum. The crude product can be re-crystallized from a cold solvent (e.g., methanol) yielding the respective ligand precursor as a solid, typically in about quantitative yield. Typically, no further purification steps are required.

In a typical general procedure, ligand precursors having the following general Formulae IC and ID were prepared:

Formula IC

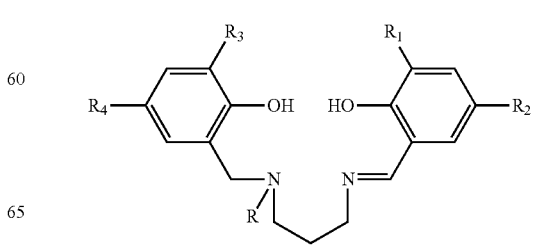

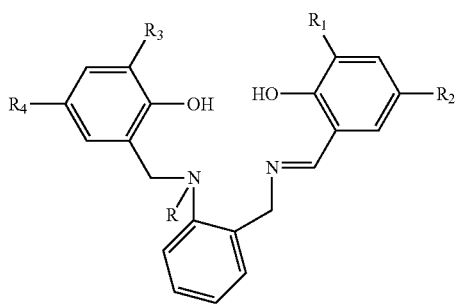

Formula ID such that "m" in scheme 2 above is 2; Ra denotes the substituents $R_1$ and $R_2$; and Rb denotes the substituents $R_3$ and $R_4$.

Using the above-described general procedure (see, Scheme 4), exemplary Salalen ligand precursors referred to herein as $Lig^{26-30}H_2$ were prepared, as representative ligand precursors having a 3-carbon atoms bridging unit. These exemplary ligands are further characterized by one or more bulky groups on the phenol proximal to the imine nitrogen (e.g., $R_1$ and $R_2$ in the above general Formula IB) and by electron-withdrawing substituents (halo-substituents) on the other phenol arm (e.g., $R_3$ and $R_4$ in the above general Formula 1B). The chemical structures of $Lig^{26-30}H_2$ are presented in FIG. 5.

The structure of all intermediates and final products was verified by NMR measurements and in most cases also by elemental analysis.

The following describes in detail the procedures used for preparing exemplary such ligand precursors.

Syntheses of $Lig^{28}H_2$ ($R_1$=adamantyl, $R_2$=Me; $R_3$=$R_4$=Cl in Formula ID); and $Lig^{29}H_2$ (($R_1$=adamantyl, $R_2$=Me; $R_3$=$R_4$=Br in Formula ID), wherein R is Formula ID is methyl:

Synthesis of 2-((methylamino)benzylimino)methyl)-4-methyl-6-adamantylphenol: A solution of 2-amino-N-methyl-benzenemethanamine.2HCl (1.13 gram, 5.4 mmol) and triethylamine (3 mL) in benzene was added to a solution of 3-adamantyl-2-hydroxy-5-methylbenzaldehyde (1.45 gram, 7.6 mmol) in benzene and the reaction mixture was refluxed for 5 hours. The solution was thereafter filtered and the solvent was removed under vacuum yielding a yellow solid (1.80 gram, 86%).

$^1$H NMR (CDCl$_3$, 400 MHz): δ=7.39 (d, 1H, J=0.8 Hz ArH), 7.28 (d, 1H, J=0.8 Hz ArH), 7.13-6.64 (m, 6H, ArH), 4.88 (s, 1H, NH), 4.30 (s, 2H, CH$_2$), 2.45 (s, 3H, NCH$_3$), 2.29 (s, 3H, ArCH$_3$), 2.17 (bs, 6H, Adamantyl), 2.08 (bs, 3H, Adamantyl), 1.79 (m, 6H, Adamantyl).

Synthesis of the Ligand Precursor: A solution of 2-(bromomethyl)-4,6-dichlorophenol (0.24 gram, 0.9 mmol, for $Lig^{28}H_2$, or of 2-(bromomethyl)-4,6-dibromophenol for $Lig^{29}H_2$) in THF (20 mL) was added dropwise to a solution of 2-((methylamino)aminobenzylimine)methyl)-4-methyl-6-adamantylphenol (0.37 gram, 0.9 mmol) and triethylamine (2 mL) in THF (20 mL) and the reaction mixture was stirred for 2 hours. The solid that formed was filtered out and the solvent was removed under vacuum. The crude product was re-crystallized from cold methanol yielding the ligand precursor as a bright yellow solid in quantitative yield. No further purification steps were required.

The following presents the analytical data of $Lig^{28}H_2$:
$^1$H NMR (CDCl$_3$, 400 MHz): δ=8.56 (s, 1H, NCH), 7.38 (d, 1H, J=1.8 Hz, ArH), 7.35-7.27 (m, 2H, ArH), 7.19 (d, 1H, J=2.5 Hz, ArH), 7.16 (d, 1H, J=1.8 Hz, ArH), 7.11-7.07 (m, 2H, ArH), 6.86 (d, 1H, J=2.5 Hz, ArH), 3.83 (s, 2H, CH$_2$), 3.80 (s, 2H, CH$_2$), 2.32 (s, 3H, NCH$_3$), 2.29 (s, 3H, ArCH$_3$), 2.17 (bs, 6H, Adamantyl), 2.07 (bs, 3H, Adamantyl), 1.77 (m, 6H, Adamantyl).

$^{13}$C NMR (CDCl$_3$, 100.67 MHz): δ=165.4 (CN), 159.3 (CO), 153.3 (CO), 148.9 (CH), 138.4 (C), 132.7 (CH), 131.6 (CH), 131.3 (CH), 130.8 (C), 130.2 (C), 129.4 (C), 128.1 (CH), 127.6 (CH), 127.3 (C), 124.7 (CH), 123.8 (CH), 119.6 (C), 60.9 (CH$_2$), 58.1 (CH$_2$), 42.0 (NCH$_3$), 40.3 (CH$_2$), 37.8 (CH$_2$), 37.7 (C), 29.1 (ArCH$_3$), 21.4 (CH).

The following presents the analytical data of $Lig^{29}H_2$:
$^1$H NMR (CDCl$_3$, 400 MHz): δ=8.48 (s, 1H, NCH), 7.39 (d, 1H, J=1.9 Hz, ArH), 7.38-7.24 (m, 3H, ArH), 7.20 (d, 1H, J=1.9 Hz, ArH), 7.11-7.07 (m, 2H, ArH), 6.72 (d, 1H, J=2.7 Hz, ArH), 3.85 (s, 2H, CH$_2$), 3.82 (s, 2H, CH$_2$), 2.32 (s, 3H, NCH$_3$), 2.28 (s, 3H, ArCH$_3$), 2.17 (bs, 6H, Adamantyl), 2.07 (bs, 3H, Adamantyl), 1.78 (m, 6H, Adamantyl).

Similarly, $Lig^{27}H_2$, in which $R_1$=$R_2$=t-Bu; and $R_3$=$R_4$=Cl in Formula ID, and R is methyl, was prepared by adding a solution of 2-amino-N-methyl-benzenemethanamine.2HCl and triethylamine in benzene to a solution of an equimolar amount of 3,5-tert-butyl-salicylaldehyde in benzene, followed by reacting the obtained intermediate with a solution of 2-(bromomethyl)-4,6-dichlorophenol in THF, as described hereinabove.

The following presents the analytical data of $Lig^{27}H_2$:
$^1$H NMR (CDCl$_3$, 400 MHz): δ=8.44 (s, 1H, NCH), 7.51 (d, 1H, J=2.3 Hz, ArH), 7.30-7.28 (m, 2H, ArH), 7.03 (d, 1H, J=2.0 Hz, ArH), 6.98 (d, 1H, J=2.0 Hz, ArH), 7.15-7.09 (m, 2H, ArH), 6.74 (d, 1H, J=2.3 Hz, ArH), 3.86 (s, 2H, CH$_2$), 3.81 (s, 2H, CH$_2$), 2.33 (s, 3H, NCH$_3$), 1.41 (s, 9H, (CH$_3$)$_3$), 1.29 (m, 9H, (CH$_3$)$_3$).

Similarly, $Lig^{26}H_2$, in which $R_1$=$R_2$=$R_3$=$R_4$=Cl in Formula ID, and R is methyl, was prepared by adding a solution of 2-amino-N-methyl-benzenemethanamine.2HCl and triethylamine in benzene to a solution of an equimolar amount of 3,5-dichloro-salicylaldehyde in benzene, followed by reacting the obtained intermediate with a solution of 2-(bromomethyl)-4,6-dichlorophenol in THF, as described hereinabove.

The following presents the analytical data of $Lig^{26}H_2$:
$^1$H NMR (CDCl$_3$, 400 MHz): δ=8.49 (s, 1H, NCH), 7.34-7.28 (m, 4H, ArH), 7.19 (d, 1H, J=2.5 Hz, ArH), 7.12 (d, 1H, J=2.5 Hz, ArH), 6.93 (d, 1H, J=2.5 Hz, ArH), 6.86 (d, 1H, J=2.5 Hz, ArH), 3.78 (s, 2H, CH$_2$), 3.65 (t, 2H, J=6.5 Hz, CH$_2$), 2.34 (s, 3H, NCH$_3$), 2.00 (m, 2H, CH$_2$).

$Lig^{30}H_2$ was prepared similarly to $Lig^{27}H_2$, while replacing the 2-amino-N-methyl-benzenemethanamine by $N^1$-methylpropane-1,3-diamine.

The following presents the analytical data of $Lig^{30}H_2$:
$^1$H NMR (CDCl$_3$, 400 MHz): δ=8.36 (s, 1H, NCH), 7.38 (d, 1H, J=2.1 Hz, ArH), 7.24 (d, 1H, J=1.9 Hz, ArH), 7.08 (d, 1H, J=2.1 Hz, ArH), 6.85 (d, 1H, J=1.9 Hz, ArH), 3.70 (s, 2H, CH$_2$), 3.63 (t, 2H, J=6.5 Hz, CH$_2$), 2.62 (t, 2H, J=6.5 Hz, CH$_2$), 2.33 (s, 3H, NCH$_3$), 1.99 (m, 2H, CH$_2$), 1.43 (s, 9H, (CH$_3$)$_3$), 1.30 (s, 9H, (CH$_3$)$_3$).

IV. Syntheses of Ligand Precursors from a Chiral Diamino Skeleton:

An exemplary general synthetic pathway of preparing Salalen ligand precursors from a chiral diamino skeleton such as, for example, 2-aminomethylpyrrolidine, is presented in Scheme 5 below.

Scheme 5

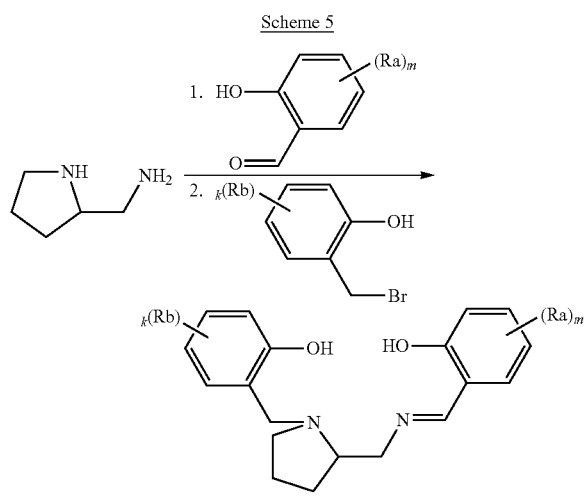

S-(2)-Pyrrolindinemethanamine.2HCl (1 molequivalent) is added to a solution of a substituted 2-hydroxy-benzaldehyde in an organic non-polar solvent (e.g., benzene) and triethylamine as an exemplary base and the reaction mixture is refluxed for 5 hours. The solvent is thereafter removed under vacuum, yielding a solid residue (>70% yield). The obtained substituted 2(iminomethyl)phenol is dissolved in THF, triethylamine as an exemplary base is added, and to the obtained solution a solution of a substituted 2-(bromomethyl) phenol (1 molequivalent) in THF is added dropwise and the reaction mixture is stirred for 2 hours. The formed solid is thereafter filtered out and the solvent is removed under vacuum. The crude product can be re-crystallized from a cold solvent (e.g., methanol) yielding the respective ligand precursor as a solid, typically in about quantitative yield. Typically, no further purification steps are required.

In a typical general procedure, ligand precursors having the following general Formula IE were prepared:

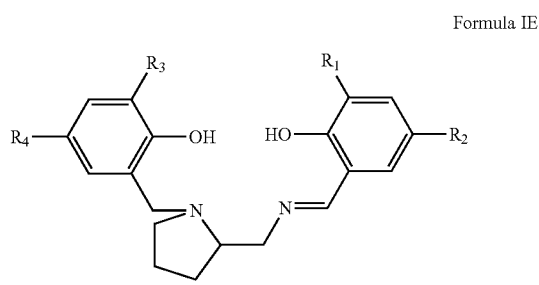

Formula IE such that "m" in scheme 2 above is 2; Ra denotes the substituents $R_1$ and $R_2$; and Rb denotes the substituents $R_3$ and $R_4$.

Using the above-described general procedure (see, Scheme 5), exemplary Salalen ligand precursors referred to herein as $Lig^{31-43}H_2$ were prepared, as representative ligand precursors having a chiral bridging unit. These exemplary ligands are further characterized by one or more bulky groups and/or by electron-withdrawing substituents (halo-substituents) on one or both phenol arms (e.g., $R_1$-$R_4$ in the above general Formula 1E). The chemical structures of $Lig^{31-43}H_2$ are presented in FIG. 6.

The structure of all intermediates and final products was verified by NMR measurements.

The following describes in detail the procedures used for preparing exemplary such ligand precursors.

Syntheses of $Lig^{31}H_2$ ($R_1$=$R_2$=t-Bu; $R_3$=$R_4$=Cl in Formula IE), of $Lig^{32}H_2$ ($R_1$=$R_2$=t-Bu; $R_3$=$R_4$=Br in Formula IE), and of $Lig^{33}H_2$ ($R_1$=$R_2$=t-Bu; $R_3$=$R_4$=I in Formula IE):

S-(2)-Pyrrolindinemethanamine.2HCl (1 molequivalent) was added to a solution of 2-hydroxy-3,5-ditert-butyl-salicylaldehyde in benzene, followed by addition of triethylamine, and the reaction mixture was refluxed for 5 hours. The obtained solution was filtered and the solvent was removed under vacuum yielding a yellow solid.

A solution of 1 molequivalent of 2-(bromomethyl)-4,6-dichlorophenol for $Lig^{31}H_2$, or 2-(bromomethyl)-4,6-dibromophenol for $Lig^{32}H_2$, or 2-(bromomethyl)-4,6-diiodophenol for $Lig^{33}H_2$, in THF (20 mL) was added dropwise to a solution of 2-((S)-(aminomethyl)pyrrolidine)-4,6-ditert-butyl-phenol and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor as a yellow solid quantitatively. No further purification steps were required.

The following presents the analytical data of $Lig^{31}H_2$:
$^1$H NMR (CDCl$_3$, 400 MHz): δ=8.37 (s, 1H, NCH), 7.38 (d, 1H, J=2.4 Hz, ArH), 7.22 (d, 1H, J=2.3 Hz, ArH), 7.09 (d, 1H, J=2.4 Hz, ArH), 6.85 (d, 1H, J=2.3 Hz, ArH), 4.26 (d, 1H, J=14.3 Hz, CH), 3.86 (m, 1H, CH), 3.63 (m, 1H, CH), 3.57 (d, 1H, J=14.3 Hz, CH), 3.11 (m, 1H, CH), 3.05 (m, 1H, CH), 2.40 (m, 1H, CH), 2.14 (m, 1H, CH), 1.94 (m, 3H, CH), 1.42 (s, 9H, (CH$_3$)$_3$), 1.29 (s, 9H, (CH$_3$)$_3$).

The following presents the analytical data of $Lig^{32}H_2$:
$^1$H NMR (CDCl$_3$, 400 MHz): δ=8.38 (s, 1H, NCH), 7.52 (d, 1H, J=2.3 Hz, ArH), 7.21 (d, 1H, J=1.9 Hz, ArH), 6.97 (d, 1H, J=2.3 Hz, ArH), 6.79 (d, 1H, J=1.9 Hz, ArH), 4.28 (d, 1H, J=14.3 Hz, CH), 3.86 (m, 1H, CH), 3.61 (m, 1H, CH), 3.59 (d, 1H, J=14.3 Hz, CH), 3.10 (m, 1H, CH), 3.01 (m, 1H, CH), 2.43 (m, 1H, CH), 2.14 (m, 1H, CH), 1.97 (m, 3H, CH), 1.41 (s, 9H, (CH$_3$)$_3$), 1.30 (s, 9H, (CH$_3$)$_3$).

The following presents the analytical data of $Lig^{33}H_2$:
$^1$H NMR (CDCl$_3$, 400 MHz): δ=8.35 (s, 1H, NCH), 7.87 (d, 1H, J=1.9 Hz, ArH), 7.37 (d, 1H, J=2.4 Hz, ArH), 7.20 (d, 1H, J=1.9 Hz, ArH), 7.08 (d, 1H, J=2.4 Hz, ArH), 4.21 (d, 1H, J=14.3 Hz, CH), 3.85 (m, 1H, CH), 3.60 (m, 1H, CH), 3.51 (d, 1H, J=14.3 Hz, CH), 3.10-3.02 (m, 2H, CH), 2.39 (m, 1H, CH), 2.11 (m, 1H, CH), 2.1.86-1.78 (m, 3H, CH), 1.42 (s, 9H, (CH$_3$)$_3$), 1.30 (s, 9H, (CH$_3$)$_3$).
$^{13}$C NMR (CDCl$_3$, 100.67 MHz): δ=167.8 (CN), 157.9 (CO), 157.3 (CO), 145.0 (CH), 140.3 (C), 136.6 (C), 136.3 (CH), 127.3 (CH), 126.2 (CH), 124.7 (C), 117.7 (C), 86.0 (C), 80.6 (C), 65.1 (CH$_2$), 63.3 (CH$_2$), 57.9 (CH$_2$), 54.8 (CH$_2$), 35.0 (CH$_2$), 34.1 (CH), 31.5 (CH$_3$), 31.3 (CH), 29.6 (C), 29.3 (CH$_3$).

Syntheses of $Lig^{34}H_2$ ($R_1$=adamantyl, $R_2$=Me; $R_3$=$R_4$=Cl in Formula IE), of $Lig^{35}H_2$ ($R_1$=adamantyl, $R_2$=Me; $R_3$=$R_4$=Br in Formula IE), and of $Lig^{36}H_2$ ($R_1$=adamantyl, $R_2$=Me; $R_3$=$R_4$=I in Formula IE):

Synthesis of 2-((S)-(aminomethyl)pyrrolidine)-4-methyl-6-adamantylphenol: S-(2)-Pyrrolindinemethanamine.2HCl (0.23 gram, 1.3 mmol) was added to a solution of 3-adamantyl-2-hydroxy-5-methylbenzaldehyde (0.36 gram, 1.3 mmol) in benzene, followed by addition of triethylamine (3 mL) and the reaction mixture was refluxed for 5 hours. The obtained solution was thereafter filtered and the solvent was removed under vacuum yielding a yellow solid (0.37 gram, 78%).

$^1$H NMR (CDCl$_3$, 400 MHz): δ=8.35 (s, 1H, NCH), 7.08 (s, 1H, ArH), 6.91 (s, 1H, ArH), 3.73 (m, 1H, CH), 3.55 (m, 1H, CH), 3.43 (m, 1H, CH), 3.05 (m, 1H, CH), 2.84 (m, H,

CH), 2.29 (s, 3H, CH$_3$), 2.19 (bs, 6H, Adamantyl), 2.10 (bs, 3H, Adamantyl), 1.98-1.94 (m, 3H, CH), 1.81 (m, 6H, Adamantyl).

$^{13}$C NMR (CDCl$_3$, 100.67 MHz): δ=166.7 (CN), 158.5 (CO), 136.8 (C), 130.5 (CH), 129.4 (C), 128.3 (CH), 126.7 (C), 64.8 (CH$_2$), 58.8 (CH), 46.1 (CH$_2$), 45.8 (CH$_2$), 40.9 (CH$_2$), 37.2 (CH$_2$), 36.9 (CH$_2$), 29.1 (ArCH$_3$), 25.1 (CH$_2$), 20.7 (CH$_2$).

Synthesis of the Ligand Precursor: A solution of 2-(bromomethyl)-4,6-dibromophenol (0.44 gram, 1.3 mmol, for Lig$^{35}$H$_2$, or an equimolar amount of 2-(bromomethyl)-4,6-dichlorophenol for Lig$^{34}$H$_2$, or of 2-(bromomethyl)-4,6-diiodophenol for Lig$^{35}$H$_2$) in THF (20 mL) was added dropwise to a solution of 2-((S)-(aminomethyl)pyrrolidine)-4-methyl-6-adamantylphenol (0.45 gram, 1.3 mmol) and triethylamine (3 mL) in THF (20 mL) and the reaction mixture was stirred for 2 hours. The solid that formed was filtered out and the solvent was removed under vacuum. The crude product was re-crystallized from cold methanol yielding the ligand precursor as a yellow solid quantitatively. No further purification steps were required.

The following presents the analytical data of Lig$^{35}$H$_2$:

$^1$H NMR (CDCl$_3$, 400 MHz): δ=8.34 (s, 1H, NCH), 7.25 (d, 1H, J=2.4 Hz, ArH), 7.09 (d, 1H, J=1.9 Hz, ArH), 6.92 (d, 1H, J=1.9 Hz, ArH), 6.88 (d, 1H, J=2.4 Hz, ArH), 4.30 (d, 1H, J=14.3 Hz, CH), 3.88 (m, 1H, CH), 3.62 (m, 1H, CH), 3.57 (d, 1H, J=14.3 Hz, CH), 3.16 (m, 1H, CH), 3.03 (m, H, CH), 2.41 (m, H, CH), 2.29 (s, 3H, CH3), 2.17 (bs, 6H, Adamantyl), 2.09 (bs, 3H, Adamantyl), 1.90 (m, 2H, CH), 1.80 (m, 6H, Adamantyl).

$^{13}$C NMR (CDCl$_3$, 100.67 MHz): δ=167.5 (CN), 159.1 (CO), 158.3 (CO), 137.4 (C), 130.8 (CH), 129.7 (CH), 128.5 (C), 126.9 (C), 126.1 (C), 124.4 (CH), 123.7 (CH), 123.1 (CH), 118.2 (C), 65.0 (CH$_2$), 63.5 (CH$_2$), 58.1 (CH), 54.8 (CH$_2$), 40.3 (CH$_2$), 37.2 (CH$_2$), 36.9 (C), 30.3 (CH$_2$), 29.6 (CH$_2$), 29.1 (ArCH$_3$), 22.9 (CH$_2$), 20.6 (CH$_2$).

The following presents the analytical data of Lig$^{34}$H$_2$:

$^1$H NMR (CDCl$_3$, 400 MHz): δ=8.34 (s, 1H, NCH), 7.54 (d, 1H, J=2.3 Hz, ArH), 7.10 (d, 1H, J=2.3 Hz, ArH), 7.05 (d, 1H, J=2.0 Hz, ArH), 6.92 (d, 1H, J=2.0 Hz, ArH), 4.30 (d, 1H, J=14.3 Hz, CH), 3.86 (m, 1H, CH), 3.61 (m, 1H, CH), 3.56 (d, 1H, J=14.3 Hz, CH), 3.13 (m, 1H, CH), 3.04 (m, 1H, CH), 2.43 (m, 2H, CH), 2.30 (s, 3H, CH$_3$), 2.17 (bs, 6H, Adamantyl), 2.10 (bs, 3H, Adamantyl), 1.91-1.84 (m, 3H, CH), 1.81 (m, 6H, Adamantyl).

The following presents the analytical data of Lig$^{36}$H$_2$:

$^1$H NMR (CDCl$_3$, 400 MHz): δ=8.33 (s, 1H, NCH), 7.38 (d, 1H, J=2.6 Hz, ArH), 7.23 (d, 1H, J=2.2 Hz, ArH), 7.05 (d, 1H, J=2.6 Hz, ArH), 6.81 (d, 1H, J=2.2 Hz, ArH), 4.31 (d, 1H, J=14.3 Hz, CH), 3.86 (m, 1H, CH), 3.69 (m, 1H, CH), 3.56 (d, 1H, J=14.3 Hz, CH), 3.12 (m, 1H, CH), 3.03 (m, 1H, CH), 2.43 (m, 2H, CH), 2.29 (s, 3H, CH$_3$), 2.17 (bs, 6H, Adamantyl), 2.10 (bs, 3H, Adamantyl), 1.90-1.81 (m, 3H, CH), 1.80 (m, 6H, Adamantyl).

Lig$^{37}$H$_2$ (R$_1$=R$_2$=R$_3$=R$_4$=Cl in Formula IE) was similarly prepared by reacting the S-(2)-Pyrrolindinemethanamine.2HCl with a 3,5-dichlorosalicyaldehyde as described hereinabove followed by reacting the obtained intermediate with 2-(bromomethyl)-4,6-dichlorophenol, as described hereinabove.

The following presents the analytical data of Lig$^{37}$H$_2$:

$^1$H NMR (CDCl$_3$, 400 MHz): δ=8.26 (s, 1H, NCH), 7.40 (d, 1H, J=2.5 Hz, ArH), 7.21 (d, 1H, J=2.5 Hz, ArH), 7.16 (d, 1H, J=2.5 Hz, ArH), 6.85 (d, 1H, J=2.5 Hz, ArH), 4.15 (d, 1H, J=14.2 Hz, CH), 3.82 (m, 1H, CH), 3.68 (m, 1H, CH), 3.63 (d, 1H, J=14.2 Hz, CH), 3.10-3.04 (m, 2H, CH), 2.41 (m, 2H, CH), 2.12 (m, 1H, CH), 1.86-1.84 (m, 3H, CH).

Lig$^{38-43}$H$_2$ (see, FIG. 6) were similarly prepared using the respective reactants (see, Steps 1 and 2 in Scheme 5), already described hereinabove.

The following presents the analytical data of Lig$^{38}$H$_2$:

$^1$H NMR (CDCl$_3$, 400 MHz): δ=8.35 (s, 1H, NCH), 7.36 (d, 1H, J=2.4 Hz, ArH), 7.19 (d, 1H, J=2.3 Hz, ArH), 7.07 (d, 1H, J=2.4 Hz, ArH), 6.83 (d, 1H, J=2.3 Hz, ArH), 4.20 (d, 1H, J=13.5 Hz, CH), 3.81 (m, 1H, CH), 3.60 (m, 1H, CH), 3.56 (d, 1H, J=13.5 Hz, CH), 3.07-2.92 (m, 2H, CH), 2.36 (m, 1H, CH), 2.11 (m, 1H, CH), 1.86-1.77 (m, 3H, CH), 1.43 (s, 9H, (CH$_3$)$_3$), 1.38 (s, 9H, (CH$_3$)$_3$), 1.29 (s, 9H, (CH$_3$)$_3$), 1.27 (s, 9H, (CH$_3$)$_3$).

$^{13}$C NMR (CDCl$_3$, 100.67 MHz): δ=167.5 (CN), 158.0 (CO), 154.3 (CO), 140.4 (CH), 140.0 (C), 136.6 (C), 135.4 (CH), 127.0 (CH), 126.1 (CH), 122.8 (C), 122.7 (C), 121.9 (C), 117.9 (C), 64.9 (CH$_2$), 63.1 (CH$_2$), 59.2 (CH$_2$), 54.4 (CH$_2$), 35.1 (CH$_2$), 34.8 (CH), 31.7 (CH$_3$), 31.5 (CH$_3$), 29.6 (CH$_3$), 29.5 (CH$_3$).

The following presents the analytical data of Lig$^{39}$H$_2$:

$^1$H NMR(C$_6$D$_6$, 200 MHz): δ=8.24 (s, 1H, NCH), 7.63 (d, 1H, J=1.9 Hz, ArH), 7.50 (d, 1H, J=1.9 Hz, ArH), 7.14 (s, 1H, ArH), 6.63 (s, 1H, ArH), 4.04 (d, 1H, J=14.9 Hz, CH$_2$), 4.00-3.76 (m, 2H, CH$_2$), 3.54 (d, 1H, J=14.9 Hz, CH$_2$), 3.15-2.95 (m, 2H, CH$_2$), 2.43-2.26 (m, 4H, CH$_2$), 2.20 (s, 6H, 2ArCH$_3$), 2.12-1.85 (bs, 12H, Adamantyl), 1.84-1.77 (bs, 6H, Adamantyl), 1.72 (m, 12H, Adamantyl).

The following presents the analytical data of Lig$^{40}$H$_2$:

$^1$H NMR (CDCl$_3$, 400 MHz): δ=8.25 (s, 1H, NCH), 7.51 (d, 1H, J=2.6 Hz, ArH), 7.32-7.12 (m, 11H, ArH), 7.03 (d, 1H, J=2.6 Hz, ArH), 6.98 (d, 1H, J=1.9 Hz, ArH), 4.15 (d, 1H, J=15.6 Hz, CH), 3.79-3.69 (m, 2H, CH), 3.46 (d, 1H, J=15.6 Hz, CH), 3.07-2.91 (m, 2H, CH), 2.37 (m, 1H, CH), 2.10-1.92 (m, 3H, CH), 1.64 (s, 6H, (CH$_3$)$_2$), 1.62 (s, 6H, (CH$_3$)$_2$).

The following presents the analytical data of Lig$^{41}$H$_2$:

$^1$H NMR (CDCl$_3$, 400 MHz): δ=8.26 (s, 1H, NCH), 7.39 (d, 1H, J=2.4 Hz, ArH), 7.14 (d, 1H, J=2.4 Hz, ArH), 6.89 (d, 1H, J=1.4 Hz, ArH), 6.63 (d, 1H, J=1.4 Hz, ArH), 4.04 (d, 1H, J=14.3 Hz, CH), 3.91-3.82 (m, 2H, CH), 3.50 (d, 1H, J=14.3 Hz, CH), 3.02 (m, 2H, CH), 2.13 (m, 1H, CH), 2.20 (s, 3H, CH$_3$), 2.05 (bs, 9H, Adamantyl), 1.84-1.77 (m, 3H, CH), 1.72 (m, 6H, Adamantyl).

The following presents the analytical data of Lig$^{42}$H$_2$:

$^1$H NMR (CDCl$_3$, 400 MHz): δ=8.22 (s, 1H, NCH), 7.68 (d, 1H, J=2.2 Hz, ArH), 7.31 (d, 1H, J=2.2 Hz, ArH), 6.88 (d, 1H, J=1.6 Hz, ArH), 6.63 (d, 1H, J=1.6 Hz, ArH), 4.06 (d, 1H, J=13.6 Hz, CH), 3.80-3.68 (m, 2H, CH), 3.51 (d, 1H, J=13.6 Hz, CH), 3.03 (m, 2H, CH), 2.13 (m, 1H, CH), 2.23 (s, 3H, CH$_3$), 2.05 (bs, 9H, Adamantyl), 1.84-1.77 (m, 3H, CH), 1.78 (m, 6H, Adamantyl).

The following presents the analytical data of Lig$^{43}$H$_2$:

$^1$H NMR (CDCl$_3$, 400 MHz): δ=8.27 (s, 1H, NCH), 7.54 (d, 1H, J=2.3 Hz, ArH), 7.29 (d, 1H, J=2.3 Hz, ArH), 6.62 (d, 1H, J=1.9 Hz, ArH), 6.52 (d, 1H, J=1.9 Hz, ArH), 4.09 (d, 1H, J=14.0 Hz, CH), 3.92-3.71 (m, 2H, CH), 3.50 (d, 1H, J=14.0 Hz, CH), 3.05 (m, 2H, CH), 2.15 (m, 1H, CH), 2.25 (s, 3H, CH$_3$), 2.10 (bs, 9H, Adamantyl), 1.92-1.81 (m, 3H, CH), 1.77 (m, 6H, Adamantyl).

Example 2

Synthesis of Metal Complexes

Group IV metal complexes of various Salalen ligands were synthesized by reacting the ligand precursors with the appropriate metal (titanium, zirconium, or hafnium) reagent (referred to herein also as a metallic reagent) in an equimolar ratio as generally depicted in Scheme 6 below.

Scheme 6

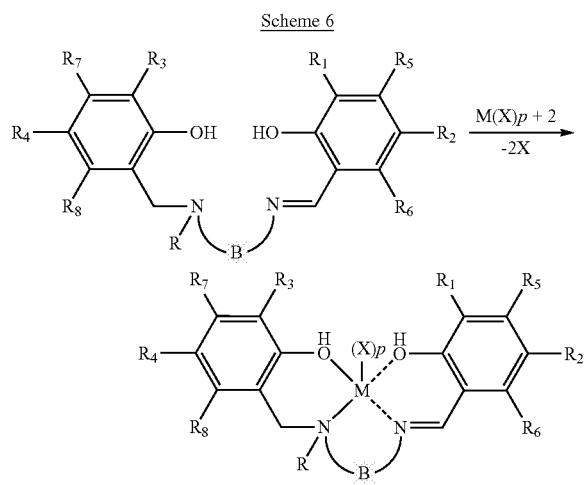

wherein $R_1$-$R_8$ and R are as defined herein; B is a bridge between the two nitrogens, and can be, for example, ethylene, propylene, 2-aminomethylaniline, or can form with R a heterocyclic ring such as aminomethylpyrollidone; M is Hf, Zr or Ti; and X is a labile group, as defined herein, including, for example, Cl, O-iPr, O-tBu, benzyl (Bn), $HNMe_2$, etc.; and "p" is an integer, preferably being 1 or 2.

The formed complex depicted in Scheme 6 can include additional neutral ligands which are not presented in the structure.

Exemplary metallic reagents that were used for obtaining the metal complexes include, without limitation, $TiBn_4$, $Ti(O\text{-}iPr)_4$, $TiCl_4$, $Ti(NMe_2)_4$, $ZrBn_4$, $Zr(O\text{-}t\text{-}Bu)_4$, $HfBn_4$, $Hf(O\text{-}t\text{-}Bu)_4$, etc.

A typical procedure for preparing the metal complexes involves the addition of a (optionally chilled) solution of a ligand precursor as described herein in a common dry organic solvent (e.g., diethyl ether or toluene) to a (optionally chilled) metal reagent (M(X)p+2) in the same solvent, and letting the reaction mixture stir while warming to room temperature, if required. After a time period ranging from several minutes to several hours, the organic solvent and the volatile by-products are removed under reduced pressure. The formed Salalen complex can be purified by common methods including extractions and crystallizations.

All of the reactions for forming the metal complexes proceeded smoothly to give the desired complexes in high to quantitative yields.

Generally, chilled solutions are utilized for thermally unstable complexes such as dibenzyl complexes, and in particular the dibenzyl titanium complexes. Chilling is not required for thermally stable complexes such as dichloro complexes.

Following is a non-limiting list including more than 150 Salalen metal complexes: $Lig^{1\text{-}10}TiBn_2$, $Lig^{13\text{-}15}TiBn_2$, $Lig^{18\text{-}25}TiBn_2$, $Lig^{31\text{-}40}TiBn_2$, $Lig^2TiCl_2$, $Lig^{1\text{-}25}Ti(Oi\text{-}Pr)_2$, $Lig^{31\text{-}43}Ti(Oi\text{-}Pr)_2$, $Lig^2Ti(NMe_2)_2$, $Lig^{4\text{-}6,9,14}ZrBn_2$, $Lig^{34\text{-}36,38}ZrBn_2$, $Lig^{1\text{-}15}Zr(Ot\text{-}Bu)_2$, $Lig^{19}Zr(Ot\text{-}Bu)_2$, $Lig^{31\text{-}43}Zr(Ot\text{-}Bu)_2$, $Lig^2HfBn_2$, $Lig^{4\text{-}6}HfBn_2$, $Lig^{9\text{-}12}HfBn_2$, $Lig^{27,31,35}HfBn_2$, $Lig^{1\text{-}12}Hf(Ot\text{-}Bu)_2$, $Lig^{27}Hf(Ot\text{-}Bu)_2$, $Lig^{31\text{-}43}Hf(Ot\text{-}Bu)_2$. Additional Salalen metal complexes were synthesized, purified and characterized according to the methodology described herein, by combining any of the herein described metallic reagents [M(X)p+2]. The exceptionally broad series of metal complexes was prepared in a relatively short time, while not relying on automated high-throughput methods. The ability to synthesize such a broad variety of well-defined Salalen complexes gives evidence to the applicability of the Salalen ligands, and to their selective binding to metals.

Following are exemplary procedures for the synthesis, work-up, and characterization of various metal complexes of Salalen ligands according to embodiments of the present invention. All other metal complexes were similarly prepared and their structure was verified by NMR measurements.

Synthesis of $Lig^1Ti(O\text{-}i\text{-}Pr)_2$: $Lig^1H_2$ (63 mg, 0.13 mmol) was dissolved in about 1 mL of ether and the solution was added dropwise to a solution of $Ti(Oi\text{-}Pr)_4$ (38 mg, 0.13 mmol) in ether at room temperature. The reaction mixture was stirred for 2 hours, the solvent was thereafter removed under vacuum, and the resulting yellow solid was washed with pentane (ca. 2 mL). The final yield was 74 mg (90%).

$^1H$ NMR($C_6D_6$, 400 MHz): δ=7.71 (d, 1H, J=2.5 Hz, ArH), 7.28 (d, 1H, J=2.6 Hz, ArH), 7.14 (s, 1H, NCH), 6.97 (d, 1H, J=2.5 Hz, ArH), 6.73 (d, 1H, J=2.6 Hz, ArH), 5.03 (septet, 1H, OCH), 4.44 (septet, 1H, OCH), 3.65 (d, J=12.9 Hz, 1H), 3.00 (m, 1H, NCH), 2.87 (d, J=12.9 Hz, 1H), 2.64 (m, 1H, NCH), 2.48 (s, 3H, $NCH_3$), 2.25 (m, 1H, NCH), 2.00 (m, 1H, NCH), 1.77 (s, 9H, $CH_3$), 1.33 (s, 9H, $CH_3$), 1.31 (d, J=6.0 Hz, 3H, $OCH(CH_3)_2$), 1.27 (d, J=6.0 Hz, 3H, $OCH(CH_3)_2$), 1.10 (d, J=6.0 Hz, 3H, $OCH(CH_3)_2$), 1.03 (d, J=6.0 Hz, 3H, $OCH(CH_3)_2$).

$^{13}C$ NMR($C_6D_6$, 100.67 MHz): δ=163.8 (CN), 161.3 (CO), 160.0 (CO), 139.8 (CH), 137.6 (CH), 129.6 (CH), 129.4 (CH), 127.5 (CH), 126.7 (C), 125.6 (C), 123.8 (C), 118.9 (C), 77.6 (CH), 75.6 (CH), 62.7 ($CH_2$), 57.0 ($CH_2$), 55.9 ($CH_2$), 49.3 ($NCH_3$), 35.5 (C), 34.0 (C), 31.4 ($C(CH_3)_3$), 29.9 ($C(CH_3)_3$), 26.1 ($4CH_3$).

Synthesis of $Lig^2Ti(O\text{-}i\text{-}Pr)_2$: $Lig^2H_2$ (94 mg, 0.17 mmol) was dissolved in about 1 mL of ether and the solution was added dropwise to a solution of $Ti(OiPr)_4$ (48 mg, 0.17 mmol) in ether at room temperature. The reaction mixture was stirred for 2 hours, the solvent was removed under vacuum, and the resulting yellow solid was washed with pentane (about 2 mL). The final yield was 87 mg (71%).

$^1H$ NMR($C_6D_6$, 400 MHz): δ=8.03 (d, 1H, J=2.1 Hz, ArH), 7.31 (s, 1H, NCH), 7.06 (d, 1H, J=2.7 Hz, ArH), 6.68 (d, 1H, J=2.1 Hz, ArH), 6.72 (d, 1H, J=2.7 Hz, ArH), 4.98 (septet, 1H, OCH), 4.51 (septet, 1H, OCH), 3.65 (d, J=12.9 Hz, 1H), 3.00 (m, 1H, NCH), 2.87 (d, J=12.9 Hz, 1H), 2.72 (m, 2H, NCH), 2.41 (s, 3H, $NCH_3$), 2.32-2.29 (m, 2H, NCH), 1.76 (s, 9H, $CH_3$), 1.31 (s, 9H, $CH_3$), 1.33 (d, J=6.1 Hz, 3H, $OCH(CH_3)_2$), 1.27 (d, J=6.1 Hz, 3H, $OCH(CH_3)_2$), 1.07 (d, J=6.1 Hz, 3H, $OCH(CH_3)_2$), 1.03 (d, J=6.1 Hz, 3H, $OCH(CH_3)_2$).

$^{13}C$ NMR ($CDCl_3$, 100.67 MHz): δ=162.7 (CN), 161.1 (CO), 157.4 (CO), 139.8 (CH), 137.6 (CH), 129.9 (CH), 129.5 (CH), 127.5 (CH), 126.7 (C), 125.6 (C), 121.2 (C), 119.1 (C), 78.1 (CH), 75.6 (CH), 62.7 ($CH_2$), 58.1 ($CH_2$), 56.8 ($CH_2$), 49.3 ($NCH_3$), 34.2 (C), 39.7 (C), 31.2 ($C(CH_3)_3$), 29.8 ($C(CH_3)_3$), 26.3 ($CH_3$), 26.1 ($3CH_3$).

Synthesis of $Lig^3Ti(O\text{-}i\text{-}Pr)_2$: $Lig^3H_2$ (52 mg, 0.08 mmol) was dissolved in about 1 mL of ether and the solution was added dropwise to a solution of $Ti(OiPr)_4$ (23 mg, 0.08 mmol) in ether at room temperature. The reaction mixture was stirred for 2 hours, the solvent was removed under vacuum, and the resulting yellow solid was washed with pentane (about. 2 mL). The final yield was 62 mg (94%).

$^1H$ NMR($C_6D_6$, 400 MHz): δ=8.20 (d, 1H, J=2.5 Hz, ArH), 7.57 (s, 1H, NCH), 7.14 (d, 1H, J=2.1 Hz, ArH), 6.74 (d, 1H, J=2.1 Hz, ArH), 6.64 (d, 1H, J=2.5 Hz, ArH), 5.03 (septet, 1H, OCH), 4.31 (septet, 1H, OCH), 4.02 (d, J=13.6 Hz, 1H), 2.84 (m, 2H, NCH), 2.71 (d, J=13.6 Hz, 1H), 2.65 (m, 2H, NCH), 2.48 (s, 3H, $NCH_3$), 1.74 (s, 9H, $CH_3$), 1.37 (s, 9H, $CH_3$), 1.33

(d, J=6.6 Hz, 3H, OCH(CH$_3$)$_2$), 1.18 (d, J=6.6 Hz, 3H, OCH (CH$_3$)$_2$), 1.14 (d, J=6.6 Hz, 3H, OCH(CH$_3$)$_2$), 1.08 (d, J=6.6 Hz, 3H, OCH(CH$_3$)$_2$).

$^{13}$C NMR (CDCl$_3$, 100.67 MHz): δ=167.2 (CN), 162.1 (CO), 161.1 (CO), 139.8 (CH), 137.6 (CH), 129.7 (CH), 129.5 (CH), 127.5 (CH), 126.1 (C), 125.5 (C), 123.8 (C), 117.0 (C), 79.8 (CH), 79.2 (CH), 60.9 (CH$_2$), 57.1 (CH$_2$), 54.7 (CH$_2$), 48.2 (NCH$_3$), 32.1 (C), 31.4 (C), 31.0 (C(CH$_3$)$_3$), 29.5 (C(CH$_3$)$_3$), 26.1-26.2 (4CH$_3$).

Synthesis of Lig$^6$Ti(O-i-Pr)$_2$: Lig$^6$H$_2$ (65 mg, 0.09 mmol) was dissolved in about 1 mL of ether and added dropwise to a solution of Ti(Oi-Pr)$_4$ (27 mg, 0.09 mmol) in ether at room temperature. The reaction mixture was stirred for 2 hours, solvent was removed under vacuum, and the resulting yellow solid was washed with pentane (ca. 2 mL). The final yield was 73 mg (91%).

$^1$H NMR(C$_6$D$_6$, 400 MHz): δ=8.05 (d, 1H, J=1.4 Hz, ArH), 7.28 (d, 1H, J=1.7 Hz, ArH), 7.23 (s, 1H, NCH), 7.07 (d, 1H, J=1.7 Hz, ArH), 6.69 (d, 1H, J=1.4 Hz, ArH), 4.92 (septet, 1H, OCH), 4.39 (septet, 1H, OCH), 3.58 (d, J=13.1 Hz, 1H), 2.91 (m, 2H, NCH), 2.79 (d, J=13.1 Hz, 1H), 2.74 (m, 2H, NCH), 2.55-2.46 (m, 6H, Adamantyl), 2.42 (s, 3H, NCH$_3$), 2.24 (s, 3H, CH$_3$), 2.06-1.85 (m, 9H, Adamantyl), 1.26 (d, J=6.0 Hz, 3H, OCH(CH$_3$)$_2$), 1.24 (d, J=6.0 Hz, 3H, OCH(CH$_3$)$_2$), 1.06 (d, J=6.0 Hz, 3H, OCH(CH$_3$)$_2$), 1.03 (d, J=6.0 Hz, 3H, OCH (CH$_3$)$_2$).

$^{13}$C NMR(C$_6$D$_6$, 100.67 MHz): δ=164.2 (CO), 163.3 (CN), 161.7 (CO), 145.9 (CH), 138.0 (CH), 137.0 (CH), 133.4 (CH), 126.4 (C), 125.5 (CH), 122.9 (C), 91.5 (C), 77.4 (CH), 75.7 (CH), 75.3 (C), 62.7 (CH$_2$), 57.1 (CH$_2$), 56.4 (CH$_2$), 49.2 (NCH$_3$), 40.8 (CH$_2$), 37.3 (C), 29.5 (ArCH$_3$), 26.2 (CH$_3$), 26.1 (CH$_3$), 26.0 (CH$_3$), 25.9 (CH$_3$), 20.5 (CH).

Single crystals of Lig$^6$Ti(Oi-Pr)$_2$ were grown from cold toluene and the structure was solved. Crystal data for complex Lig$^6$Ti(Oi-Pr)$_2$: C$_{34}$H$_{46}$I$_2$O$_4$N$_2$Ti; M=878.45; triclinic; space group P-1; a=10.4279(2) Å, b=13.3246(2) Å, c=14.8896(3) Å, α=91.2197(7)°, β=100.9237(8)°, γ=111.1700(9)°, V=1885.18(6) Å$^3$; T=110(2) K; Z=2; D$_c$=1.548 g cm$^{-3}$; μ(Mo Kα)=1.903 mm$^{-1}$; R$_1$=0.0410 and wR$_2$=0.1056 for 7007 reflections with I>2σ (I); R$_1$=0.0556 and wR$_2$=0.1152 for all 8876 unique reflections.

Synthesis of Lig$^7$Ti(O-i-Pr)$_2$: Lig$^7$H$_2$ (53 mg, 0.10 mmol) was dissolved in about 1 mL of ether and the solution was added dropwise to a solution of Ti(OiPr)$_4$ (28 mg, 0.10 mmol) in ether at room temperature. The solution was stirred for 2 hours, the solvent was removed under vacuum, and the resulting yellow solid was washed with pentane (about 2 mL). The final yield was 64 mg (92%).

$^1$H NMR(C$_6$D$_6$, 400 MHz): δ=7.92 (d, 1H, J=1.9 Hz, ArH), 7.09-7.06 (m, 1H, ArH), 7.00 (s, 1H, NCH), 6.95 (d, 1H, J=1.9 Hz, ArH), 6.93-6.88 (m, 3H, ArH), 6.62-6.60 (m, 2H, ArH), 4.88 (septet, 1H, OCH), 4.40 (septet, 1H, OCH), 3.90 (d, J=13.2 Hz, 1H), 2.88 (m, 1H, NCH), 2.47 (d, J=13.2 Hz, 1H), 2.40 (s, 3H, NCH$_3$), 2.31 (m, 1H, NCH), 1.93-1.81 (m, 2H, NCH), 1.35 (d, J=6.1 Hz, 3H, OCH(CH$_3$)$_2$), 1.19 (d, J=6.1 Hz, 3H, OCH(CH$_3$)$_2$), 1.03 (d, J=6.1 Hz, 3H, OCH (CH$_3$)$_2$), 1.00 (d, J=6.1 Hz, 3H, OCH(CH$_3$)$_2$).

Synthesis of Lig$^1$TiBn$_2$: Lig$^1$H$_2$ (37 mg, 0.08 mmol) was dissolved in ca. 1 mL of toluene chilled to about −35° C. and the solution was added dropwise to a stirring red solution of TiBn$_4$ (33 mg, 0.08 mmol) in about 1 mL of toluene chilled to about −35° C. The color of the solution changed to dark red-brown. The reaction mixture was allowed to warm to room temperature, and after 15 minutes of stirring the solvent was removed under vacuum yielding a brown solid, which was washed with ca. 1 mL of pentane and dried in vacuo. The final yield was 53 mg (95%).

$^1$H NMR(C$_6$D$_6$, 400 MHz): δ=7.56 (d, 1H, J=2.9 Hz, ArH), 7.48 (s, 1H, NCH), (7.25 d, 1H, J=2.7 Hz, ArH), (7.05-6.84 (m, 10H, ArH), 6.67 (d, 1H, J=2.7 Hz, ArH), 6.43 (d, 1H, J=2.9 Hz, ArH), 4.79 (d, J=14.3 Hz, 1H), 4.16 (m, 1H, NCH), 3.95 (m, 1H, NCH), 3.66 (m, 1H, NCH), 3.37 (d, J=15.3 Hz, 1H), 3.24 (m, 1H, NCH), 2.95 (d, J=12.1 Hz, 1H), 2.71 (s, 3H, NCH$_3$), 2.49 (d, J=12.1, 1H), 2.42 (d, J=10.8, 2H), 1.99 (d, J=14.4 Hz, 1H), 1.77 (s, 9H, C(CH$_3$)$_3$), 1.30 (s, 9H, C(CH$_3$)$_3$).

Synthesis of Lig$^2$TiBn$_2$: Lig$^2$H$_2$ (48 mg, 0.09 mmol) was dissolved in about 1 mL of cold toluene and the solution was added dropwise to a stirring red solution of TiBn$_4$ (36 mg, 0.09 mmol) in about 1 mL of cold toluene. The color of the solution changed to dark red-brown. The reaction mixture was stirred for 15 minutes and the solvent was thereafter removed under vacuum, yielding a brown solid, which was washed with about 1 mL of pentane and dried in vacuo. The final yield was 61 mg (86%).

$^1$H NMR(C$_6$D$_6$, 400 MHz): δ=7.54 (d, 1H, J=2.6 Hz, ArH), 7.49 (s, 1H, NCH), 7.10-7.07 (m, 2H, ArH), 7.02-6.95 (m, 8H, ArH), 6.70 (d, 1H, J=2.4 Hz, ArH), 6.64 (d, 1H, J=2.6 Hz, ArH), 6.59 (d, 1H, J=2.4 Hz, ArH), 4.83 (d, J=14.4 Hz, 1H), 4.21 (m, 1H, NCH), 3.95 (m, 1H, NCH), 3.66 (m, 1H, NCH), 3.39 (d, J=10.8 Hz, 1H), 3.24 (m, 1H, NCH), 2.79 (d, J=13.9 Hz, 1H), 2.71 (s, 3H, NCH$_3$), 2.47 (d, J=13.9, 1H), 2.41 (d, J=10.8, 2H), 1.99 (d, J=14.4 Hz, 1H), 1.77 (s, 9H, C(CH$_3$)$_3$), 1.31 (s, 9H, C(CH$_3$)$_3$).

$^{13}$C NMR (CDCl$_3$, 100.67 MHz): δ=170.9 (CN), 167.5 (CO), 156.8 (CO), 148.8 (CH), 141.6 (CH), 139.9 (CH), 138.3 (C), 137.5 (C), 135.5 (CH), 135.2 (CH), 134.6 (C), 134.1 (CH), 132.4 (CH), 129.8 (CH), 128.2 (CH) 126.8 (CH), 126.3 (CH), 126.0 (CH), 125.3 (CH), 122.2 (CH), 120.5 (CH), 115.7 (CH), 112.5 (C), 110.3 (C), 109.3 (CH), 74.7 (CH$_2$), 71.9 (CH$_2$), 61.3 (CH$_2$), 55.3 (CH$_2$), 49.8 (CH$_2$), 37.8 (NCH$_3$), 34.4 (C), 33.6 (C), 31.6 (C(CH$_3$)$_3$), 30.5 (C(CH$_3$)$_3$).

Synthesis of Lig$^3$TiBn$_2$: Lig$^3$H$_2$ (80 mg, 0.12 mmol) was dissolved in about 1 mL of cold toluene and the solution was added dropwise to a stirring red solution of TiBn$_4$ (51 mg, 0.12 mmol) in about 1 mL of cold toluene. The color of the solution changed to dark red-brown. The reaction mixture was stirred for 15 minutes and the solvent was thereafter removed under vacuum, yielding a brown solid, which was washed with about 1 mL of pentane and dried in vacuo. The final yield was 110 mg (100%).

$^1$H NMR(C$_6$D$_6$, 400 MHz): δ=8.42 (s, 1H, NCH), 7.85 (d, 1H, J=2.3 Hz, ArH), 7.10-6.98 (m, 4H, ArH), 6.95-6.87 (m, 4H, ArH), 6.73-6.64 (m, 2H, ArH), 6.21 (d, 1H, J=2.3 Hz, ArH), 4.52 (d, J=12.4 Hz, 1H), 4.43 (m, 2H, NCH), 3.69 (d, J=9.1 Hz, 1H), 3.245 (m, 1H, NCH), 2.95 (d, J=12.4 Hz, 1H), 2.70 (s, 3H, NCH$_3$), 2.62 (d, J=13.9 Hz, 1H), 2.54 (d, J=13.9, 2H), 1.76 (d, J=9.1 Hz, 1H), 1.79 (s, 9H, C(CH$_3$)$_3$), 1.41 (s, 9H, C(CH$_3$)$_3$).

$^{13}$C NMR (CDCl$_3$, 100.67 MHz): δ=169.8 (CN), 165.2 (CO), 158.1 (CO), 144.1 (CH), 139.2 (CH), 138.8 (C), 135.9 (C), 135.8 (CH), 135.6 (CH), 134.9 (C), 139.7 (CH), 133.5 (CH), 129.1 (CH), 128.9 (CH) 127.7 (CH), 127.5 (CH), 126.2 (CH), 125.3 (CH), 124.9 (CH), 119.8 (CH), 118.7 (CH), 113.0 (C), 112.7 (C), 74.6 (CH$_2$), 69.4 (CH$_2$), 63.3 (CH$_2$), 52.9 (CH$_2$), 43.8 (CH$_2$), 41.7 (NCH$_3$), 33.4 (C), 31.3 (C(CH$_3$)$_3$), 30.7 (C), 29.4 (C(CH$_3$)$_3$).

Synthesis of Lig$^6$TiBn$_2$: Lig$^6$H$_2$ (83 mg, 0.12 mmol) was dissolved in about 1 mL of toluene chilled to about −35° C. and the solution was added dropwise to a stirring red solution of TiBn$_4$ (50 mg, 0.12 mmol) in about 1 mL of toluene chilled to about −35° C. The color of the solution changed to dark red-brown. The reaction mixture was allowed to warm to room temperature, and after 15 minutes of stirring the solvent was removed under vacuum, yielding a brown solid, which was washed with ca. 1 mL of pentane and dried in vacuo. The final yield was 105 mg (95%).

$^1$H NMR($C_6D_6$, 400 MHz): δ=7.53 (s, 1H, NCH), 7.27 (d, 1H, J=2.6 Hz, ArH), 7.18 (d, 1H, J=1.5 Hz, ArH), 7.09-7.07 (m, 2H, ArH), 7.02-6.93 (m, 6H, ArH), 6.88-6.80 (m, 2H, ArH), 6.45 (d, 1H, J=2.6 Hz, ArH), 6.38 (d, 1H, J=1.5 Hz, ArH), 4.79 (d, J=12.3 Hz, 1H), 4.10 (m, 2H, NCH), 3.96 (d, J=13.8 Hz, 1H), 3.52 (d, J=11.8 Hz, 1H), 3.48 (d, J=11.8 Hz, 1H), 3.32-3.13 (m, 2H, NCH),), 2.81 (d, J=13.9, 1H), 2.70 (s, 3H, $NCH_3$), 2.65 (d, J=10.8, 2H), 2.51-2.26 (m, 9H, Adamantyl), 2.21 (s, 3H, $ArCH_3$), 1.99-1.75 (m, 6H, Adamantyl).

$^{13}$C NMR($C_6D_6$, 100.67 MHz): δ=170.4 (CN), 168.4 (CO), 166.6 (CO), 159.1 (CH), 155.2 (CH), 141.5 (CH), 140.4 (C), 132.4 (C), 132.2 (CH), 129.7-128.7 (7CH), 126.2 (CH), 125.0 (CH), 122.8 (CH), 121.7 (CH), 120.6 (CH), 61.8 ($CH_2$), 55.7 ($CH_2$), 49.7 ($CH_2$), 42.8 ($CH_2$), 41.6 ($CH_2$), 41.1 ($NCH_3$), 37.9 (C), 37.2 ($CH_2$), 29.6 ($ArCH_3$), 29.2 (CH), 20.5 (CH).

Synthesis of $Lig^7TiBn_2$: $Lig^7H_2$ (52 mg, 0.10 mmol) was dissolved in about 1 mL of cold toluene and the solution was added dropwise to a stirring red solution of $TiBn_4$ (40 mg, 0.10 mmol) in about 1 mL of cold toluene. The color of the solution changed to dark red-brown. The reaction mixture was stirred for 15 minutes and the solvent was thereafter removed under vacuum yielding a brown solid, which was washed with about 1 mL of pentane and dried in vacuo. The final yield was 71 mg (96%).

$^1$H NMR($C_6D_6$, 400 MHz): δ=8.16 (s, 1H, NCH), 8.05 (d, 1H, J=1.7 Hz, ArH), 7.12-7.02 (m, 6H, ArH), 6.98-6.73 (m, 8H, ArH), 6.68 (d, 1H, J=1.7 Hz, ArH), 3.86 (d, J=12.7 Hz, 1H), 3.72 (d, J=13.2 Hz, 1H), 3.64 (m, 2H, NCH), 3.51 (m, 2H, NCH), 3.37 (d, J=13.2 Hz, 1H), 2.82 (d, J=14.4 Hz, 1H), 2.77 (s, 3H, $NCH_3$), 2.68 (d, J=12.7 Hz, 1H), 2.55 (d, J=14.4 Hz, 1H).

$^{13}$C NMR ($CDCl_3$, 100.67 MHz): δ=167.8 (CN), 167.1 (CO), 156.8 (CO), 145.7 (CH), 139.7 (CH), 138.9 (CH), 138.8 (C), 137.7 (C), 136.1 (CH), 135.2 (CH), 134.1 (C), 133.5 (CH), 133.4 (CH), 128.8 (CH), 128.7 (CH), 128.5 (CH), 127.9 (CH), 126.9 (CH), 126.5 (CH), 126.0 (CH), 125.4 (CH), 125.2 (CH), 123.2 (CH), 119.5 (CH), 118.1 (CH), 116.7 (C), 81.7 ($CH_2$), 74.7 ($CH_2$), 62.7 ($CH_2$), 55.7 ($CH_2$), 51.5 ($CH_2$), 41.1 ($NCH_3$).

Synthesis of $Lig^{35}TiBn_2$: $Lig^{35}H_2$ (84 mg, 0.14 mmol) was dissolved in about 1 mL of toluene chilled to about −35° C. and the solution was added dropwise to a stirring red solution of $TiBn_4$ (56 mg, 0.14 mmol) in about 1 mL of toluene chilled to about −35° C. The color of the solution changed to dark red-brown. The reaction mixture was allowed to warm to room temperature, and after 15 minutes of stirring the solvent was removed under vacuum, yielding a brown solid, which was washed with about 1 mL of pentane and dried in vacuo. The final yield was 95 mg (80%).

$^1$H NMR($C_6D_6$, 400 MHz): δ=7.74 (s, 1H, NCH), 7.34 (d, 1H, J=2.5 Hz, ArH), 7.19 (d, 1H, J=1.9 Hz, ArH), 7.14-7.08 (m, 2H, ArH), 6.98-6.84 (m, 6H, ArH), 6.83-6.78 (m, 2H, ArH), 6.45 (d, 1H, J=2.5 Hz, ArH), 6.38 (d, 1H, J=1.9 Hz, ArH), 5.12 (d, J=12.8 Hz, 1H), 4.17-4.02 (m, 4H, CH), 3.81 (d, J=12.8 Hz, 1H, CH), 3.67 (m, 4H, CH), 3.50 (m, 2H, CH), 3.05 (m, 2H, CH),), 2.73 (m, 1H, CH), 2.45 (m, 9H, Adamantyl), 2.20 (s, 3H, $ArCH_3$), 1.87 (m, 6H, Adamantyl);

$^{13}$C NMR($C_6D_6$, 100.67 MHz): δ=170.1 (CN), 168.1 (CO), 167.8 (CO), 159.1 (CH), 155.3 (CH), 141.5 (CH), 140.3 (C), 132.4 (C), 130.1-128.7 (8CH), 126.7 (CH), 125.0 (CH), 122.9 (CH), 121.4 (CH), 120.6 (CH), 119.8 (C), 58.9 ($CH_2$), 57.4 ($CH_2$), 51.2 ($CH_2$), 49.9 ($CH_2$), 49.4 ($CH_2$), 42.8 ($CH_2$), 41.6 ($CH_2$), 39.8 (C), 37.2 ($CH_2$), 29.6 ($ArCH_3$), 29.2 (CH), 20.5 ($CH_2$).

Synthesis of $Lig^2TiCl_2$: $TiCl_4$ (0.018 mL, 0.16 mmol) was added to a stirring solution of $Lig^2H_2$ (90 mg, 0.16 mmol) in about 2 mL of toluene. The color of the solution changed to dark red. The reaction mixture was stirred for 15 minutes and the solvent was thereafter removed under vacuum, yielding a red solid, which was washed with about 1 mL of pentane and dried in vacuo. The final yield was 109 mg (100%). The complex showed a very low solubility and was not characterized by NMR.

Synthesis of $Lig^1ZrBn_2$: $Lig^1H_2$ (34 mg, 0.07 mmol) was dissolved in about 1 mL of toluene chilled to about −35° C. and the solution was added dropwise to a stirring solution of $ZrBn_4$ (34 mg, 0.07 mmol) in about 1 mL of toluene chilled to about −35° C. The reaction mixture was allowed to warm to room temperature, and after 2 hours of stirring the solvent was removed under vacuum, yielding a yellow solid, which was washed with about 1 mL of pentane and dried in vacuo. The final yield was 49 mg (90%).

$^1$H NMR($C_6D_6$, 400 MHz): δ=7.72 (d, 1H, J=2.5 Hz, ArH), 7.62 (d, 1H, J=2.4 Hz, ArH), 7.32 (s, 1H, NCH), 7.15-6.95 (m, 10H, ArH), 6.89 (d, 1H, J=2.5 Hz, ArH), 6.78 (d, 1H, J=2.4 Hz, ArH), 2.76 (m, 2H, $CH_2$), 2.53 (m, 4H, $CH_2$), 1.87 (s, 3H, $NCH_3$), 1.73 (m, 2H, $CH_2$), 1.69 (s, 9H, $(CH_3)_3$), 1.30 (s, 9H, $(CH_3)_3$), 1.23 (m, 2H, $CH_2$);

$^{13}$C NMR($C_6D_6$, 100.67 MHz): δ=169.2 (CN), 168.1 (CO), 167.6 (CO), 159.1 (CH), 155.4 (CH), 140.9 (CH), 140.4 (C), 132.1-127.9 (LOCH), 124.5 (CH), 122.5 (CH), 122.4 (CH), 119.6 (CH), 117.1 (C), 59.2 ($CH_2$), 58.8 ($CH_2$), 42.8 ($NCH_3$), 42.1 ($CH_2$), 38.2 ($CH_2$), 35.7 ($CH_2$), 32.1 (C), 31.9 ($CH_3$), 25.2 ($CH_3$), 25.0 (C).

Synthesis of $Lig^{11}HfBn_2$: $Lig^{11}H_2$ (46 mg, 0.09 mmol) was dissolved in about 1 mL of toluene chilled to about −35° C. and the solution was added dropwise to a stirring red solution of $HfBn_4$ (46 mg, 0.09 mmol) in about 1 mL of toluene chilled to about −35° C. The reaction mixture was allowed to warm to room temperature, and after 2 hours of stirring the solvent was removed under vacuum, yielding a white solid, which was washed with about 1 mL of pentane and dried in vacuo. The final yield was 62 mg (90%).

$^1$H NMR($C_6D_6$, 400 MHz): δ=7.45 (d, 1H, J=2.3 Hz, ArH), 7.33 (d, 1H, J=2.0 Hz, ArH), 7.28 (s, 1H, NCH), 7.27-7.26 (m, 2H, ArH), 7.12-6.99 (m, 4H, ArH), 6.82-6.80 (m, 2H, ArH), 6.79 (d, 1H, J=2.3 Hz, ArH), 6.71-6.67 (m, 2H, ArH), 6.62 (d, 1H, J=2.0 Hz, ArH), 3.51 (d, J=13.8 Hz, 1H), 2.90-2.84 (m, 2H, $CH_2$), 2.80 (d, J=9.7 Hz, 1H, CH), 2.72 (d, J=9.7 Hz, 1H, CH), 2.59 (d, J=13.8 Hz, 1H, CH), 2.48-2.36 (m, 9H, Adamantyl), 2.23 (s, 3H, $ArCH_3$), 2.20-2.18 (m, 6H, Adamantyl), 2.15 (s, 3H, $NCH_3$) 2.02 (d, J=11.6 Hz, 1H, CH), 1.91-1.88 (m, 2H, $CH_2$), 1.83 (d, J=11.6 Hz, 1H, CH), 1.42 (s, 9H, $(CH_3)_3$), 1.30 (s, 9H, $(CH_3)_3$).

Analysis of the structural features of the prepared metal complexes was performed by various techniques including $^1$H NMR, $^{13}$C NMR, and crystallography in cases where single crystals were obtained. The complexes were found to be mono-nuclear, containing a single Salalen ligand per metal atom for all the tested complexes. The complexes were also characterized as containing labile groups (see, X in Scheme 6 above). These labile groups can be activated to form a reactive polymerization catalyst.

Spectroscopic characterization showed that the Salalen metal complex is obtained as a single diastereomer. Based on the coordination tendencies of the amine donor (facial) and the imine-donor (meridional), the overall wrapping of the Salalen ligands around octahedral metal centers is expected to be fac-mer, which is $C_1$-symmetric. Such a symmetry is suitable for polymerization catalysis since the two labile groups are cis-related. This mode of wrapping was supported by spectroscopic characterization and crystallographic studies of several complexes, as detailed hereinbelow.

Notably, a single diastereomer is obtained also for the chiral Salalen ligands based on the aminomethyl-pyrrolidine (exemplified by representative structures $Lig^{31-43}H_2$), for which the number of possible diastereomers is double. These complexes have a pre-determined chirality at the metal center.

Crystallographic structure analysis, was performed for the complexes $[Ti(Lig^6)(O-i-Pr)_2]$, $[Ti(Lig^{28})(O-i-Pr)_2]$, and $[Hf(Lig^1)(O-t-Bu)_2]$, as presented in FIGS. 7A-C.

In all of these complexes, the Salalen ligand was found to wrap diastereoselectively such that the {O,N,N} array of donors around the amine donor wraps in a facial fashion, and the {O,N,N} array of donors around the imine donor wraps in a meridional fashion completing an altogether fac-mer wrapping. In the titanium complex of the Salalen ligand having the chiral aminomethyl-pyrrolidine backbone ($[Ti(Lig^{28})(O-i-Pr)_2]$), the relationship between the chirality of the ligand, and the specific fac-mer diastereomer formed could be established, and fit that predicted by simple molecular models.

Example 3

Catalytic Polymerization

The metal complexes described herein were employed in polymerization of olefins. Several polymerization procedures were employed, depending on the pre-catalyst and the monomer of choice. Dibenzyl pre-catalysts are typically activated with either boron-type co-catalysts or with MAO. Other pre-catalysts, such as dichloro complexes, are typically activated with MAO.

In a typical polymerization procedure of a monomer which is liquid at atmospheric pressure like 1-hexene, the metal complex was added to this said monomer and the co-catalyst was added to a second portion of the same monomer. Mixing these two portions led to initiation of the polymerization process which was continued for a period of time that depended on the rate of the polymerization process and ranged from below 1 minute to several hours. The excess of the remaining monomer was removed under reduced pressure, traces of the non-polymeric materials (resulting from the catalyst and co-catalyst) were removed, and the polymer was isolated and analyzed. Such polymerizations may be performed in the presence of a pre-dried organic solvent like toluene.

In a typical polymerization of propylene, a stainless steel reactor that was equipped with a magnetic stir-bar and charged with 500 equivalents of MAO and the metal complex was cooled down with a liquid nitrogen bath. A measured volume of propylene was condensed; the reactor was sealed and was allowed to warm to RT. The polymerization was pursued for 13-14 hours. The remaining monomer was released and the polymer was treated with acidified methanol solution (5% HCl solution) and petroleum ether. The soluble polymer part was extracted from the petroleum ether solution by evaporating the solvent under reduced pressure. The insoluble polymers were obtained by filtration and were air dried.

An alternative polymerization procedure involves the formation of the pre-catalyst in situ by mixing in the polymerization mixture the Salalen ligand precursor and the metal precursor (such as $TiBn_4$) and then adding the co-catalyst and monomer. In the case of 1-hexene polymerizations, using $B(C_6F_5)_3$ as co-catalyst, polymerization runs of 2-4 hours were employed. Polymerizations of 1-hexene with MAO as co-catalyst were faster, and the polymerization runs were between 1 minute (500 molequivalents of MAO) to 10 minutes (50 equivalents of MAO). Propylene was polymerized either without solvent in the liquid form (cryogenically condensed in a stainless-steel reactor, thawed, and thereafter stirred for 14 hours at 25° C.) with 500 molequivalents of MAO as co-catalyst, or in toluene solution with 500 molequivalents of MAO as co-catalyst.

The polymer samples were characterized by several techniques:

$^{13}$C-NMR is employed to determine stereoregularity (%[mmmm]), and a presence of chain ends or low molecular weight oligomers, at room temperature for the soluble poly (1-hexene) and at high temperature for the crystalline polypropylene;

Gel Permeation Chromatography (GPC) is employed to determine molecular weights ($M_w$ and $M_n$) and molecular weight distributions (PDI), at room temperature for the soluble poly(1-hexene) and at higher temperature for the crystalline polypropylene;

Differential Scanning calorimetry (DSC) was employed for characterizing the obtained polypropylene, by determining Meting Transition ($T_m$), and Crystallization temperature ($T_c$).

General Procedures

The Salalen-based systems described herein were employed as catalysts in polymerization of olefins following suitable activation.

Various types of olefins are polymerized by these systems, including, for example, non-substituted olefins such as ethylene, low olefins such as propylene, higher olefins such as 1-hexene, and olefins bearing aromatic substituents such as styrene. The catalytic activity toward such a broad scope of monomers attests to the applicability of the Salalen-based catalytic systems both for polymerization and co-polymerization of a variety of monomers.

A variety of polymerization procedures was tested and found to be suitable for the Salalen-based systems. Salalen complexes including alkyl labile groups (such as benzyl) are typically activated by alkyl elimination with either boron-type co-catalysts or with co-catalysts of the aluminum family such as MAO, or different combinations of co-catalysts of these families. Salalen complexes that include non-alkyl labile groups such as chloro groups are typically alkylated in the activation process, making MAO and related co-catalysts as well as combination of various catalysts suitable for their activation.

In a typical polymerization procedure of a monomer which is liquid at atmospheric pressure, e.g., 1-hexene or styrene, a metal complex as described herein is added to one portion of the monomer and a co-catalyst is added to a second portion of the same monomer. Mixing the two monomer portions leads to initiation of the polymerization process, which is continued for a time period that typically depends on the rate of the polymerization process and can range from less than 1 minute to several hours. Once the reaction is complete, the excess of the remaining monomer is removed under reduced pressure, traces of the non-polymeric materials (resulting from the catalyst and co-catalyst) are removed, and the polymer is isolated and analyzed.

Such polymerization procedures may be performed in the presence of a pre-dried organic solvent such as toluene or heptane.

For monomers which are gaseous at room temperature and may be easily condensed (e.g., propylene), several polymerization procedures are employed.

In a typical solvent-less polymerization of a gaseous monomer such as propylene, a stainless steel reactor equipped with an inner glass sleeve and a magnetic stir-bar is charged with the appropriate number of molequivalents of MAO and with the metal complex, and is cooled down with a liquid nitrogen bath. A measured volume of propylene is condensed; the reactor is sealed and allowed to warm to room temperature. The polymerization is typically pursued for 13-14 hours. The summed weight of monomer and formed polymer are measured, and the remaining monomer is released. The polymer is treated with acidified solution (e.g., 5% HCl/methanol solution) and petroleum ether, and left to stir for 12 hours. The soluble polymer part is thereafter extracted from the petroleum ether solution by evaporating the solvent under reduced pressure. The insoluble polymer part is obtained by filtration and air dried.

In a typical solution polymerization procedure of a gaseous monomer such as propylene or ethylene, a dry solvent such as toluene, containing a predetermined number of molequivalents of a co-catalyst such as MAO, is charged with the monomer up to a given pressure at a pre-determined temperature (e.g., between 0 and 70° C.). The pre-catalyst is injected and the pressure and temperature of the polymerization reaction are monitored. A mass-flow controller is optionally employed to sustain a specific pressure, and the gas consumption is thus monitored as well. A typical pressure is 33.5 psig. The polymerization is stopped by addition of methanol and release of the unreacted monomer. The obtained polymer is treated with an acidified solution (5% HCl/methanol solution) and left to stir for 12 hours. The soluble polymer part is extracted from the solution by evaporating the solvent under reduced pressure. The insoluble polymer part is obtained by filtration and air dried.

An alternative polymerization procedure involves the formation of the pre-catalyst in situ, by mixing of the ligand precursor and the metal reagent in the polymerization mixture. Such a procedure takes advantage of the fast reaction of the Salalen ligand precursor with metal reagents such as $MBn_4$ (M=Ti, Zr, Hf), and of the clean formation of a single diastereomer of the complex, which is suitable for polymerization catalysis. This option alleviates the necessity to isolate a well-defined metal complex, and may be particularly useful in the case of thermally less stable Salalen complexes such as benzyl titanium complexes.

In a typical such procedure, a toluene solution of the metal reagent (e.g., $TiBn_4$) is added to a toluene solution of a Salalen ligand precursor, followed by saturation of solution with the monomer (e.g., propylene, at 33.5 psig). A co-catalyst (e.g., MAO, about 250 molequivalents) is then injected and the polymerization is allowed to proceed as described hereinabove. The obtained polymer is isolated as described hereinabove.

The polymer samples were characterized by one or more of the following techniques:

$^{13}C$-NMR was employed to determine stereoregularity (%[mmmm]), and the possible presence of chain ends or low molecular weight oligomers. The spectra were measured at room temperature in $CDCl_3$ for soluble polymers such as poly(1-hexene) and at high temperature (110-155° C.) in $CD_2Cl_4$ for polymer samples that were insoluble at room temperature (mostly isotactic polypropylene).

Gel Permeation Chromatography (GPC) was employed to determine molecular weights ($M_w$ and $M_n$) and molecular weight distributions (PDI), at room temperature for soluble polymers such as poly(1-hexene) and at high temperature for crystalline polymer samples (e.g., isotactic polypropylene).

Differential Scanning calorimetry (DSC) was employed for characterizing the obtained crystalline polymers by determining Melting Transition ($T_m$, ° C.), and Heat of Melting ($\Delta H$, J/g).

Polymerization of Propylene

The Salalen-based systems described herein were found to be suitable for polymerization of propylene under a broad range of conditions. Salalen metal precatalysts of the form $Lig^xM(X)_p$ where $Lig^x$ is one of the Salalen ligands, M is a group 4 metal, and X is an alkyl (benzyl) or halo (chloro) group, were employed with MAO as a typical co-catalyst. The polymerization was run either in solvent-less liquid propylene or in propylene dissolved in an organic solvent such as toluene, according to the general procedures described hereinabove. The ratio of co-catalyst varied, with a typical ratio being 500:1, and with a ratio of 50:1 still being sufficient for production of substantial quantities of polypropylene. For polymerizations in solution, different temperatures were employed. An active catalytic polymerization of propylene was performed also without the use of an isolated pre-catalyst, but rather with pre-catalyst formed in situ (in the polymerization mixture) by mixing of a Salalen ligand precursor and a metal reagent such as $TiBn_4$.

Polymerization of Propylene by Salalen-Titanium Catalyst Systems:

The titanium Salalen catalyst systems presented herein showed a tendency to produce isotactic polymers, which was found to be affected by the nature of the skeleton and of the substituents of the two phenol rings of the Salalen ligand. For most of the systems studied, highly isotactic polypropylene of high molecular weight was produced (as was immediately apparent from the solid form of the obtained polymers). For several catalytic systems, polypropylene having melting transitions ($T_m$) exceeding 169.5° C. were obtained. These values represent the highest melting transitions ever reported for "as prepared" (not extracted or annealed) isotactic polypropylene prepared by catalytic polymerization—either homogeneous (metallocene or non-metallocene) or heterogeneous, and measured by employing a standard DSC protocol ($2^{nd}$ heating run, 10° C. $min^{-1}$).

The degree of isotacticity was evaluated by the melting transition of the polypropylene, and by $^{13}C$ NMR analysis of the peak of the methyl group, at the pentad level, wherein the mmmm pentad represents an isotactic sequence, and an r relationship signifies a deviation from ideal isotacticity.

For all polymers exhibiting a high degree of isotacticity, a ratio of 2:2:1 of the [mmmr], [mmrr], and [mrrm] pentad peaks were found, which corresponds to an enantiomorphic site control of isoselectivity.

No regioerror or chain-end peaks could be detected in the obtained spectra.

It was generally found that for polymers samples with high enough molecular weights, a higher percent of the [mmmm] was also reflected in a higher melting transition. For the polymers with the highest melting transitions, [mmmm] ≥99.5% was measured. These values are among the highest ever reported for isotactic polypropylene prepared by any catalyst, and correspond to one stereo-error every one thousand repeat units.

Molecular weight analysis of the obtained polypropylene samples showed high molecular weights (e.g., above 200,000 and up to above 1,000,000), and narrow molecular weight distributions (PDI of around 2).

Due to high MW and high isotacticity, many of the samples exhibited low solubility and could not be analyzed by GPC at high temperatures.

Liquid, Solvent-less Polymerization:

The results of the polymerization runs of liquid propylene (condensed propylene, no added solvent) with the titanium pre-catalysts of $Lig^{1-10}TiX_2$ (X=Bn, Cl) are summarized in Table 1 below.

TABLE 1

Polymerization of liquid propylene with titanium catalysts, 500 molequiv of MAO

| Catalyst | Monomer condensed (g) | Polymer obtained (g) | $T_m$ (°C.) | $\Delta H$ (J/g) |
|---|---|---|---|---|
| $Lig^1TiBn_2$ | 7.05 | 3.72 | 150 | 107 |
| $Lig^2TiBn_2$ | 8.27 | 4.49 | 157 | 96.9 |
| $Lig^2TiCl_2$ | 8.42 | 4.95 | 142, 152 | 30.4 |
| $Lig^3TiBn_2$ | 8.65 | 5.21 | 155 | 89.8 |
| $Lig^4TiBn_2$ | 7.15 | 2.73 | 166 | 96.5 |
| $Lig^5TiBn_2$ | 7.88 | 2.97 | 167 | 95.5 |
| $Lig^6TiBn_2$ | 9.52 | 1.10 | 164 | 97.0 |
| $Lig^6TiBn_2{}^a$ | 8.00 | 0.87 | 158.5 | 60.9 |
| $Lig^7TiBn_2$ | 7.63 | 0.72 | 130 | 1.6 |
| $Lig^8TiBn_2$ | 6.72 | 3.46 | 162.1 | 90.0 |
| $Lig^9TiBn_2$ | 10.0 | 2.64 | 126.8 | 56.8 |
| $Lig^{10}TiBn_2$ | 5.94 | 0.896 | 155.7 | 58.2 |

$^a$50 equiv of MAO

In view of the obtained data, the following can be noted: $Lig^{1-3}TiBn_2$, three Salalen titanium complexes including tert-butyl substituents on the imine-side phenol (see, for example, $R_1$ and $R_2$ in the general Formula hereinabove) and Cl, Br or I substituents on the amine-side phenol (see, for example, $R_3$ and $R_4$ in the general Formula hereinabove), yielded highly isotactic polypropylene having [mmmm] of 90, 95, and 95%, melting transitions ($T_m$) of, 149, 157, and 155° C., and molecular weights ($M_w$) of 647000, 415000, and 882000, respectively.

The corresponding series in which the tert-butyl ortho substituent ($R_1$) has been replaced with the bulkier 1-adamantyl substituent, namely $Lig^{4-6}TiBn_2$, yielded polypropylene of even higher isotacticities, with [mmmm] of >99%, >99%, and 99%, melting transitions ($T_m$) of 166, 167, and 164° C., and molecular weights ($M_w$) of 787000, 255000, and 418000, respectively. The very close $T_m$ values by three different catalysts of the same series attests to similar catalytic sites, and to reproducible performance. Reducing the equivalents of MAO to as low as 50, still produced polypropylene, and its melting transition was about 6° C. lower than that produced when 500 equiv were employed—$Lig^6TiBn_2$, $T_m$=158.5° C.

A dichlorotitanium complex, $Lig^2TiCl_2$, led to an active polymerization catalyst upon activation with 500 equiv of MAO. A combination of the bulky ortho-cumyl group on the imine-side phenol and Br substituents on the amine-side phenol ($Lig^8TiBn_2$) also led to a high-melting polypropylene ($T_m$=162° C., $M_w$=283000) Further increasing the bulkiness of the substituent on the imine-side phenol ($Lig^9TiBn_2$) led to a decrease in tacticity as evident in a lower melting transition ($T_m$=127° C.).

Removing the alkyl substituent altogether to obtain a non-bulky Salalen ligand ($Lig^7TiBn_2$), led to polypropylene having a melting transitions of 130° C. with low heats of fusion of 1.6 J/g that indicated a low degree of crystallinity and hence a mostly stereoirregular polypropylene. The low crystallinity, combined with the presence of melting transition, a rubbery appearance, and $^{13}C$ NMR spectrum of the polypropylene that appears like a superposition of an atactic polypropylene and an isotactic polypropylene may indicate a stereoblock structure. Such a material can find applications as a thermoplastic elastomer.

The combination of bulky groups on the two aromatic rings ($Lig^{10}TiBn_2$) led to polypropylene having somewhat lower tacticity in comparison to the values recorded for $Lig^{4-6}TiBn_2$ ($T_m$=155.7° C.), possibly indicating over-crowdedness that may hamper isoselectivity and activity.

The results of the polymerization runs of liquid propylene (condensed propylene, no added solvent) with additional titanium pre-catalysts are summarized in Table 2.

TABLE 2

Polymerization of liquid propylene with titanium catalysts, 500 molequiv of MAO

| Catalyst | Monomer condensed (g) | Polymer obtained (g) | $T_m$ (°C.) | $\Delta H$ (J/g) |
|---|---|---|---|---|
| $Lig^{18}TiBn_2$ | 9.55 | 0.42 | 143 | 30 |
| $Lig^{19}TiBn_2$ | 8.42 | 0.365 | 156.4 | 25.0 |
| $Lig^{20}TiBn_2$ | 5.38 | 3.76 | 148,156 | 46.2 |
| $Lig^{21}TiBn_2$ | 7.86 | 1.03 | 154 | 6.5 |
| $Lig^{22}TiBn_2$ | 8.06 | 0.88 | 116 | 2.9 |
| $Lig^{23}TiBn_2$ | 7.88 | 1.22 | 142 | 43.9 |
| $Lig^{24}TiBn_2$ | 7.50 | 1.81 | 126.6 | 13.1 |
| $Lig^{25}TiBn_2$ | 8.98 | 2.32 | 130.7 | 49.1 |
| $Lig^{31}TiBn_2$ | 8.06 | 5.89 | 153.1 | 105.8 |
| $Lig^{32}TiBn_2$ | 7.85 | 2.19 | 156.2 | 107.7 |
| $Lig^{33}TiBn_2$ | 6.37 | 1.67 | 160.0 | 99.8 |
| $Lig^{34}TiBn_2$ | 6.93 | 4.32 | 168.1 | 129.7 |
| $Lig^{35}TiBn_2$ | 10.0 | 1.49 | 168.3 | 117.1 |
| $Lig^{36}TiBn_2$ | 9.77 | 1.38 | 165.5 | 115.0 |
| $Lig^{38}TiBn_2$ | 9.33 | 0.61 | 159.6 | 74.4 |
| $Lig^{40}TiBn_2$ | 7.46 | 2.41 | 162.4 | 95.8 |

In view of the obtained data, the following can be noted:

$Lig^{18-20}TiBn_2$ include bulky groups and electron withdrawing groups in reverse arrangement to the order described for the complexes described above, namely the bulky groups (adamantyl) are on the phenol proximal to the amine donor, and the electron withdrawing groups (Cl, Br, I) are on the phenol proximal to the imine donor. All these complexes led to isotactic polypropylene upon activation with 500 equiv of MAO, but the melting transitions were somewhat inferior in comparison to the titanium complexes with the original substitution pattern ($Lig^{4-6}TiBn_2$) signifying the clear-cut structure-activity relationships in these systems.

The series of titanium complexes $Lig^{21-25}TiBn_2$ include combinations of halo groups on the two phenol arms. Following activation, these catalyst systems all led to polypropylene, which was generally of lower tacticity in comparison to polypropylene derived from Salalen systems that also include bulky phenolate groups. The polypropylene with the highest melting point was obtained from the catalyst having the bulkiest halo-groups—iodo—on both phenol arms ($Lig^{23}TiBn_2$). $Lig^{21}TiBn_2$ yielded polypropylene having $T_m$ of 154° C., however the low heat of melting signified a low average isotacticity. High molecular weight polypropylene was found for these catalysts with $Lig^{21}TiBn_2$ and $Lig^{23}TiBn_2$ giving $M_w$ values of 1,380,000 (PDI=1.95) and 1,130,000 (PDI=1.85), respectively.

$Lig^{31-36}TiBn_2$ and $Lig^{38,40}TiBn_2$ are dibenzyltitanium complexes whose Salalen ligands are assembled around the chiral aminomethylpyrrolidine backbone. These catalysts exhibited the most spectacular polymerization results in terms of isotacticity of the resulting polypropylene. Remarkably, the performance of these catalysts mirrors (and outperforms) the performance of the catalysts based on the non-chiral N-methylethylenediamine described above, and give further evidence regarding the accurate control of the active site by the phenol substitution pattern, and the reproducibility of the catalysts behavior. An increase in polypropylene melting transitions relative to the series relying on non-chiral Salalen ligands, signifies a more stereoselective monomer insertion, and the suitability of the aminomethyl-pyrrolidine as a backbone for Salalen ligands.

The Salalen catalysts including adamantyl substituents (Lig$^{34-36}$TiBn$_2$) gave polypropylene of higher tacticities than the tert-butyl analogues (Lig$^{31-33}$TiBn$_2$). In particular, Lig$^{35}$TiBn$_2$ gave polypropylene with extremely high T$_m$ of 168.3° C., and Lig$^{34}$TiBn$_2$ gave polypropylene with almost as high T$_m$ of 168.1° C. $^{13}$C NMR characterization of the polypropylene obtained from Lig$^{35}$TiBn$_2$, presented in FIGS. 8A and 8B, indicated an ultra-high degree of isotacticity of [mnimm]=99.6%, which corresponds to one stereoerror in ca. 1200 repeat units. No evidence for regio-errors could be found in that spectrum. Presumably, this is one of the most regular polypropylene samples ever produced.

It can be seen that the results are highly reproducible, as the change of polymerization conditions (including higher and lower polymerization temperatures) leads to a maximum difference of melting transition of 2.1° C. Some of the melting transitions recorded are higher than that obtained in solventless liquid propylene, with the maximum value being 168.3° C. for polymerization at 0° C. The molecular weights of the polymers exceeded 230,000 and the molecular weight distributions were low (PDI of about 2.0), signifying homogenous catalysis. It can further be seen that the activities recorded are high and attained at very short times, indicating a lack of an induction period.

TABLE 3

Solution polymerization of propylene with Lig$^5$TiBn$_2$

| Catalyst (polymerization Temp) | Amount of catalyst | Equiv MAO | Time (seconds) | Activity (g mmol$^{-1}$ h$^{-1}$) | Polymer (g) | T$_m$ (° C.) | ΔH (J/g) |
| --- | --- | --- | --- | --- | --- | --- | --- |
| Lig$^5$TiBn$_2$ (room temperature) | 8 mg [10 μmol] | 500 | 34 | 39,600 | 3.31 | 167.8 | 92.4 |
| Lig$^5$TiBn$_2$ (room temperature) | 1.2 mg [1.4 μmol] | 3000 | 480 | 4,300 | 0.71 | 165.3 | 57.1 |
| Lig$^5$TiBn$_2$ (room temperature) | 5 mg [6.1 μmol] | 500 | 10 | 71,200 | 1.21 | 166.9 | 79.4 |
| Lig$^5$TiBn$_2$ (room temperature) | 3 mg [3.7 μmol] | 500 | 10 | 32,500 | 0.331 | 166.2 | 84.1 |
| Lig$^5$TiBn$_2$ (0-5° C.) | 3 mg [3.7 μmol] | 500 | 10 | 31,100 | 0.316 | 168.3 | 99.3 |
| Lig$^5$TiBn$_2$ (50-60° C.) | 3 mg [3.7 μmol] | 1000 | 30 | 12,500 | 0.382 | 166.9 | 89.2 |

A somewhat lower T$_m$ of 162.4° C. was recorded when the imine side phenol included cumyl substituents (Lig$^{40}$TiBn$_2$). When the substitution pattern on both phenol groups included the bulky tert-butyl groups a further decrease in melting transition was found (Lig$^{38}$TiBn$_2$, T$_m$=159.6° C.).

Solution Polymerization:

Selected catalysts were employed in polymerization of propylene in solution. Toluene was the solvent, and the polymerization conditions including the concentration of the pre-catalyst, the ratio of co-catalyst to pre-catalyst, and the effect of polymerization temperature on catalyst performance and polymer properties were studied. The solution polymerizations enabled the evaluation of catalyst activity. In certain cases, extremely high activities were recorded, and the rates of polymerizations may be diffusion-controlled, as instantaneous formation of polymer was found upon addition of pre-catalyst to a toluene solution containing the pre-catalyst and propylene. The activity values in those cases include the formal time elapsing until the quencher was added (methanol), and should represent a lower limit of activity. Notably, the degree of tacticity obtained by those catalysts in solution, as evident in the melting transitions of the resulting polypropylene was even higher than that obtained in liquid propylene.

Propylene polymerization results under different conditions employing Lig$^5$TiBn$_2$ as precatalyst are summarized Table 3 below. Generally, polymerization was performed using propylene of an initial pressure of 33.5 psig dissolved in 50 mL of toluene; no additional monomer was added during polymerization.

Table 4 below presents the results obtained with pre-catalysts Lig$^{34-36}$TiBn$_2$ in toluene solution, which were found to produce the best results. As can be seen, all of these catalysts exhibited high activities, and led to ultra-highly isotactic polypropylene samples with melting transitions of T$_m$≥169.6° C., as presented in FIG. 9. To our knowledge such T$_m$ figures have never been described in the art for "as obtained" isotactic polypropylene (not annealed, extracted, etc.) and measured with differential scanning calorimetry by the accepted standard protocol. The very close values reflect again on the reproducibility of these catalytic systems, and on the accurate control of monomer approach by the designed Salalen-based catalyst systems.

TABLE 4

Polymerization of propylene in toluene solution (50 mL) with titanium complexes Lig$^{34-36}$TiBn$_2$ (10 μmol catalyst) at room temperature

| Catalyst Mol | Equiv MAO | Time (seconds) | Activity (g mmol$^{-1}$ h$^{-1}$) | Polymer (g) | T$_m$ (° C.) | ΔH (J/g) |
| --- | --- | --- | --- | --- | --- | --- |
| Lig$^{34}$TiBn$_2$ | 500 | 45 | 8,160 | 1.02 | 169.7 | 135.9 |
| Lig$^{35}$TiBn$_2$ | 500 | 30 | 11,400 | 0.95 | 169.9 | 104.2 |
| Lig$^{36}$TiBn$_2$ | 500 | 30 | 10,560 | 0.88 | 169.6 | 135.9 |

Solution Polymerization of In-situ Prepared Pre-catalyst:

To test the possibility of producing polypropylene with in-situ formed metal complex, the following exemplary protocol was employed: 16 mg (0.020 mmol) of the ligand precursor Lig$^{35}$H$_2$ was added to a solution of 1 molequivalent of TiBn$_4$ in 280 mL of toluene at room-temperature, and the solution was saturated with propylene at a pressure of 33.5 psig. 250 molequiv of MAO dissolved in toluene were added and the polymerization was allowed to proceed at room temperature for 3 hours. Following the work-up procedure described hereinabove 1.94 grams of isotactic polypropylene were obtained, having a $T_m$ of 169.5° C. ($\Delta H$=90.5 J/g). The melting transition is thus similar to that obtained by employing pre-prepared Lig$^{35}$Bn$_2$, and attests to the applicability of this alternative procedure for the production of highly isotactic polypropylene. Other procedures for in-situ Salalen catalyst formation are also contemplated.

Scheme 7 below presents the general synthetic scheme of producing highly isotactic polypropylene using exemplary Salalen catalyst systems as described herein:

Scheme 7

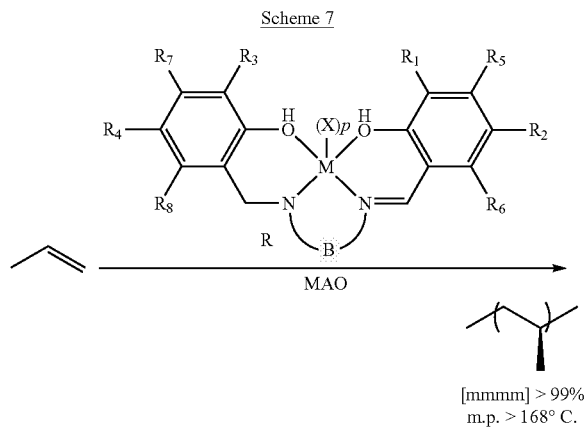

[mmmm] > 99%
m.p. > 168° C.

Polymerization of Propylene by Salalen-Zirconium and Salalen-Hafnium Systems:

The zirconium and hafnium Salalen-based catalytic systems were found to be suitable catalysts for propylene polymerization upon activation with the appropriate co-catalysts. Tables 5 and 6 below present the data obtained for the polymerization of propylene in liquid propylene by dibenzyl-zirconium and dibenzyl-hafnium complexes, respectively, activated by 500 molequiv of MAO.

TABLE 5

Polymerization of liquid propylene, 500 equiv of MAO, Zr-Bn complexes

| Catalyst | Monomer condensed (g) | Polymer obtained (g) | $T_m$ (° C.) | $\Delta H$ (J/g) |
|---|---|---|---|---|
| Lig$^4$ZrBn$_2$ | 8.26 | 7.86 | 100 | 30 |
| Lig$^5$ZrBn$_2$ | 9.03 | 6.67 | 112 | 50 |
| Lig$^6$ZrBn$_2$ | 7.87 | 5.51 | 120.6 | 48.5 |
| Lig$^9$ZrBn$_2$ | 8.24 | 4.39 | atactic | — |
| Lig$^{34}$ZrBn$_2$ | 10.98 | 7.23 | 90 | 10 |
| Lig$^{35}$ZrBn$_2$ | 8.11 | 4.76 | 97.6 | 25.2 |
| Lig$^{37}$ZrBn$_2$ | 9.80 | 2.95 | 146.0 | 29.2 |

TABLE 6

Polymerization of liquid propylene, 500 equiv of MAO, Hf-Bn complexes

| Catalyst | Monomer condensed (g) | Polymer obtained (g) | $T_m$ (° C.) | $\Delta H$ (J/g) |
|---|---|---|---|---|
| Lig$^2$HfBn$_2$ | 8.73 | 8.04 | 91 | 16 |
| Lig$^4$HfBn$_2$ | 7.73 | 6.05 | 136.6 | 68.7 |
| Lig$^5$HfBn$_2$ | 7.67 | 7.06 | 142.4 | 83.3 |
| Lig$^6$HfBn$_2$ | 9.91 | 9.21 | 145.5 | 98.1 |
| Lig$^9$HfBn$_2$ | 8.51 | 3.91 | atactic | — |
| Lig$^{10}$HfBn$_2$ | 8.28 | 0.54 | 155.2 | 83.7 |
| Lig$^{11}$HfBn$_2$ | 7.16 | 0.39 | 154.9 | 116.1 |
| Lig$^{31}$HfBn$_2$ | 8.93 | 5.70 | atactic | — |
| Lig$^{35}$HfBn$_2$ | 6.24 | 3.53 | 137.4 | 54.2 |
| Lig$^{37}$HfBn$_2$ | 7.02 | 1.17 | 138, 146, 155 | 39 |

Notably, for the catalyst systems based on both metals, a higher conversion of the propylene to polypropylene was observed, when the Salalen ligand did not contain bulky substituents on both of the phenol rings. This conversion was almost quantitative in several cases, attesting to the stability of these catalytic systems.

The polymers obtained were of lower tacticity in comparison to the titanium-based catalyst system, probably because of the larger radius of these heavier metals.

In contrast to the titanium series, the chiral skeleton of aminomethyl-pyrrolidine did not show superior performance compared to the simpler methylaminoethylamine, as evident by lower heat of melting of the obtained polymers.

The hafnium-based catalysts were more iso-selective than the zirconium-based systems, as apparent when comparing the series of Lig$^4$MBn$_2$-Lig$^5$MBn$_2$-Lig$^6$MBn$_2$ for the two metals.

In contrast to the titanium series, wherein the isotactic polypropylene produced by the Salalen ligands with Cl, Br, and I substituents on the amine side phenol showing close $T_m$ values, a substantial increase in $T_m$ values is observed in the zirconium series on increasing the size of the halo substituent. A shallower but still apparent behavior is observed for the hafnium complexes with a maximal $T_m$ value of 145.5° C. ($\Delta H$=98.1 J/g) found for Lig$^6$HfBn$_2$.

Increasing the size of the imine side phenol substituent to trityl (Lig$^9$MBn$_2$) led to atactic polypropylene for both metals. On the other hand, hafnium catalysts featuring bulky groups on both phenol rings (Lig$^{10,11}$HfBn$_2$) led to polypropylene of higher $T_m$ values of about 155° C. $^{13}$C NMR analysis of the polypropylene derived from Lig$^{10}$HfBn$_2$ revealed a high degree of isotacticity of [mmmm]=94.7%.

Lower quantities of polypropylene were obtained by the latter sterically encumbered hafnium catalysts, that may signify a hindered access to the catalytic site under these conditions, or to early precipitation of these less soluble samples.

Polymerization of 1-hexene

The Salalen-based systems described herein were found to be suitable for polymerization of 1-hexene, following the general procedures described herein, under different conditions and with activation of different co-catalysts (see, Table 7 below). Salalen metal pre-catalysts of the form Lig$^x$MBn$_p$ where Lig$^x$ is one of the Salalen ligands described herein, M is a group 4 metal (Ti or Zr), Bn denotes benzyl and p is typically 2, were employed with either B(C$_6$F$_5$)$_3$ or MAO as typical co-catalysts in polymerization. The polymerization was successfully performed either in solvent-less liquid 1-hexene or in 1-hexene diluted in an inert dry solvent such as n-heptane. When B(C$_6$F$_5$)$_3$ was employed as a co-catalyst, it was taken in slight excess of 1.2 equivalents. For MAO, The ratio of co-catalyst to pre-catalyst was typically 500:1, but a lower ratio of 50:1 also led to an active catalyst.

Table 7 below presents the data obtained for polymerization of 1-hexene with titanium and zirconium Salalen catalyst systems at room temperature.

TABLE 7

Polymerization of neat 1-hexene (unless specified otherwise) with titanium and zirconium complexes (RT).

| Catalyst | Cat employed | Co-catalyst | Equiv co-catalyst | Time min | Activity (g mmol$^{-1}$ h$^{-1}$) | Polymer (g) | % mmmm |
|---|---|---|---|---|---|---|---|
| Lig$^1$TiBn$_2$ | 7 mg [10 μmol] | B(C$_6$F$_5$)$_3$ | 1.2 | 120 | 4.5 | 0.13 | 63 |
| Lig$^1$TiBn$_2$ | 7 mg [10 μmol] | MAO | 500 | 1 | 11,600 | 2.80 | 76 |
| Lig$^1$TiBn$_2$[a] | 7 mg [10 μmol] | MAO | 500 | 1 | 10,200 | 2.46 | 92 |
| Lig$^2$TiBn$_2$ | 8 mg [10 μmol] | B(C$_6$F$_5$)$_3$ | 1.2 | 120 | 18 | 0.47 | 79 |
| Lig$^2$TiBn$_2$ | 8 mg [10 μmol] | MAO | 500 | 1 | 10,800 | 2.30 | 91 |
| Lig$^3$TiBn$_2$ | 9 mg [10 μmol] | B(C$_6$F$_5$)$_3$ | 1.2 | 240 | 8 | 0.38 | 94 |
| Lig$^3$TiBn$_2$ | 9 mg [10 μmol] | MAO | 500 | 3 | 1,200 | 0.68 | 95 |
| Lig$^6$TiBn$_2$ | 9 mg [10 μmol] | B(C$_6$F$_5$)$_3$ | 1.2 | 120 | 10 | 0.21 | 89 |
| Lig$^6$TiBn$_2$ | 9 mg [10 μmol] | MAO | 500 | 10 | 1,500 | 2.78 | 96 |
| Lig$^6$TiBn$_2$ | 9 mg [10 μmol] | MAO | 50 | 10 | 613 | 1.12 | >99 |
| Lig$^7$TiBn$_2$ | 8 mg [10 μmol] | B(C$_6$F$_5$)$_3$ | 1.2 | 120 | 24 | 0.63 | 87 |
| Lig$^7$TiBn$_2$ | 8 mg [10 μmol] | MAO | 500 | 60 | 68 | 0.89 | 86 |
| Lig$^1$ZrBn$_2$ | 8 mg [10 μmol] | B(C$_6$F$_5$)$_3$ | 1.2 | 60 | 7 | 0.10 | atactic |
| Lig$^2$ZrBn$_2$ | 8 mg [10 μmol] | B(C$_6$F$_5$)$_3$ | 1.2 | 60 | 28 | 0.34 | atactic |
| Lig$^{13}$ZrBn$_2$ | 8 mg [10 μmol] | B(C$_6$F$_5$)$_3$ | 1.2 | 60 | 27 | 0.27 | 40 |

[a]15 mL n-heptane and 5 mL of 1-hexene.

As can be seen in Table 7, polymerization of 1-hexene with the Salalen-titanium complexes and B(C$_6$F$_5$)$_3$ as co-catalyst led to poly(1-hexene) polymers with high molecular weights and narrow molecular weight distributions. For example, the five titanium complexes of the Salalen ligands Lig$^{1-3,6,7}$TiBn$_2$ gave poly(1-hexene) samples with molecular weights in the range of M$_n$=300,000-400,000 and molecular weight distributions of PDI=1.04-1.09.

The polymers were isotactic to different degrees. For example, Lig$^1$TiBn$_2$ gave poly(1-hexene) with an average degree of isotacticity [mmmm] of 63%, Lig$^2$TiBn$_2$ gave poly (1-hexene) with a higher degree of isotacticity [mmmm] of 79%, whereas Lig$^3$TiBn$_2$ gave poly(1-hexene) with a high degree of isotacticity [mmmm] of 94%, as determined by $^{13}$C-NMR spectra of the corresponding polymer samples. The activity of these titanium catalysts was found to range between about 4.5-24 g mmol$^{-1}$ h$^{-1}$ for polymerization runs of 2-4 hours.

The zirconium complexes Lig$^1$ZrBn$_2$ and Lig$^2$ZrBn$_2$ showed similar activity in 1-hexene polymerization upon activation with B(C$_6$F$_5$)$_3$ and gave rise to stereoirregular poly (1-hexene). Lig$^{13}$ZrBn$_2$ (featuring a benzyl substituent on the amine-donor) activated with B(C$_6$F$_5$)$_3$ led to an isotactically enriched poly(1-hexene with an isotacticity [mmmm] of about 40%.

Changing the co-catalyst from B(C$_6$F$_5$)$_3$ to MAO was found to lead to improved activity of the resulting catalysts and of the degree of isotacticity of the resulting poly(1-hexene). For example, upon activation of Lig$^{1-3,6,7}$TiBn$_2$ with 500 molequiv. of MAO as co-catalyst in neat 1-hexene, a fast reaction was observed, as apparent from the boiling of the monomer within a few seconds. Activities of up to 11,000 grams mmol$^{-1}$ h$^{-1}$ were recorded. Most pre-catalysts led to poly(1-hexene) of high isotacticities (with [mmmm] commonly above 90%).

To test if the isotacticity of the MAO-activated titanium catalysts was hampered by the fast temperature rise during polymerization, some polymerization processes were performed with n-heptane as an inert solvent added to absorb the released heat. Thus, upon activation with MAO in the presence of 3:1 volume ratio of n-heptane to 1-hexene, Lig$^3$TiBn$_2$ showed almost the same activity and yielded poly(1-hexene) of improved isotacticity ([mmmm] of 92% vs 76%).

As little as 50 molequiv of MAO were sufficient to produce highly active catalysts (400 grams mmol$^{-1}$ h$^{-1}$). For example, when Lig$^6$TiBn$_2$ was activated with 50 molequiv of MAO, a poly(1-hexene) sample was obtained with isotacticity so high that stereoerrors could not be detected ([mmmm]>99%), as reflected in the $^{13}$C NMR of the polymer presented in FIG. 10.

The narrow molecular weight distributions and high molecular weights testify to the homogeneous nature of the catalyst and the negligible chain transfer to MAO.

Polymerization of Ethylene

The Salalen-based catalyst systems described herein were found to be suitable for the synthesis of high molecular weight linear polyethylene. Polymerization reactions were run in toluene solutions with MAO as a representative co-catalyst. Different polymerization temperatures—either 0° C. or 70° C., and different polymerization times were employed. The co-catalyst to pre-catalyst ratio was varied by retaining the volume of toluene and quantity of MAO employed, while changing the quantity of pre-catalyst.

The obtained data is presented in Table 8 below.

TABLE 8

Polymerization of ethylene in toluene solutions (70 mL toluene).

| Catalyst | Cat employed | MolEquiv MAO | Temp. (° C.) | Time (min) | Activity (g mmol$^{-1}$ h$^{-1}$) | Polymer (g) | T$_m$ (° C.) | ΔH (J/g) |
|---|---|---|---|---|---|---|---|---|
| Lig$^6$TiBn$_2$ | 9.1 mg [10 μmol] | 500 | 0 | 10 | 1,900 | 3.13 | 133.5 | 134.9 |
| Lig$^6$TiBn$_2$ | 0.22 mg [0.24 μmol] | 19000 | 70 | 10 | 13,500 | 0.54 | 133.9 | 77.6 |
| Lig$^{21}$TiBn$_2$ | 6.5 mg [10 μmol] | 500 | 0 | 240 | 39 | 1.56 | 135.03 | 150.9 |
| Lig$^{22}$TiBn$_2$ | 7.1 mg [10 μmol] | 500 | 0 | 240 | 34 | 1.35 | 133.70 | 146.0 |
| Lig$^{23}$TiBn$_2$ | 10.1 mg [10 μmol] | 500 | 0 | 240 | 61 | 2.43 | 133.87 | 143.1 |
| Lig$^{24}$TiBn$_2$ | 8 mg [10 μmol] | 500 | 0 | 240 | 50 | 1.98 | 133.70 | 101.8 |
| Lig$^{25}$TiBn$_2$ | 8 mg [10 μmol] | 500 | 0 | 240 | 126 | 5.05 | 131.70 | 21.9 |
| Lig$^{36}$TiBn$_2$ | 3 mg [3 μmol] | 1500 | 0 | 10 | 2,800 | 1.42 | 127.7 | 58.1 |
| Lig$^{36}$TiBn$_2$ | 0.22 mg [0.24 μmol] | 19000 | 0 | 30 | 5,750 | 0.69 | 134.03 | 92.4 |

As can be seen in Table 8, all complexes were successfully employed in polyethylene polymerization catalysis. The activities changed as a function of the catalyst employed. Salalen catalysts featuring halo-substituents on both of the phenol rings led to lower activities, whereas complexes of Salalen ligands combining bulky and electron withdrawing groups led to higher activities. The typical melting transitions of the obtained polyethylene samples were 133° C. The very high catalyst activity for Lig$^6$TiBn$_2$ at 70° C. attests to the stability of the Salalen complexes.

Polymerization of Styrene

The Salalen-based catalyst systems described herein were found to be suitable for polymerization of styrene.

In typical polymerizations, the dibenzyltitanium complex Lig$^{5,32,38}$TiBn$_2$ (10 μmol) were dissolved in 1 mL of styrene and added to a stirred solution of MAO (500 equiv) in 2 mL styrene. The resulting mixture was stirred for 1 hour, during which the solution became viscous. The polymer was treated with acidified methanol solution (5% HCl solution). The insoluble polymer was obtained by filtration and was dried in air. These catalysts showed mild activity (23-74 g mmol$^{-1}$ h$^{-1}$) and produced syndiotactic polystyrene with typical Tm=269.9° C., Tm=268.1° C. and Tm=268.1° C., respectively (see, Table 9). The relatively low heat of melting may indicate the co-presence of amorphous polystyrene.

Table 9 below presents the data obtained for exemplary polymerization reactions performed according to the general procedure described hereinabove for liquid, solvent-less polymerization of styrene.

As can be seen in Table 9, dibenzyl titanium complexes were found to lead to syndiotactic polystyrene. This finding is uncommon because, typically, homogeneous titanium catalysts of oxidation state of (IV) polymerize α-olefins to isotactic polymers whereas homogeneous titanium catalysts of oxidation state of (III) polymerize styrene to syndiotactic polystyrene. The unique combination of activities of the Salalen-based catalytic systems may enable them to produce polymers with unusual compositions and microstructures.

Copolymerizations

The Salalen-based systems described herein were found to be suitable for copolymerizations of alpha-olefin monomers as well. The physical properties of the polymers could be tuned by changing of polymerization parameters.

Following is an example of copolymerization of ethylene and 1-hexene, which is representative of copolymerizations of high-olefins and low olefins, employing a representative Salalen complex.

A 250 mL glass reactor equipped with a magnetic stir-bar was charged with 500 molequiv of MAO, 3 mL of 1-hexene and 50 mL of heptane at room-temperature. Ethylene was passed through the reaction mixture at atmospheric pressure for 20 minutes, and for all of the duration of the polymerization. The polymerization was started by injection of 10 μmol of catalyst Lig$^6$TiBn$_2$. The polymerization was stopped after 1 hour, by injection of methanol and venting-off of the remaining ethylene. The solution was treated with acidified methanol solution (5% HCl solution), and the insoluble polymer was filtered off and dried in air. The insolubility is con-

TABLE 9

Polymerization of styrene (room temperature).

| Catalyst | Cat employed | Equiv MAO | Time hours | Activity (g mmol$^{-1}$ h$^{-1}$) | Polymer (g) | T$_m$ (° C.) | ΔH (J/g) |
|---|---|---|---|---|---|---|---|
| Lig$^5$TiBn$_2$ | 9 mg [10 μmol] | 500 | 1 | 23.3 | 0.233 | 269.9 | 19.1 |
| Lig$^{32}$TiBn$_2$ | 7 mg [10 μmol] | 500 | 1 | 50.9 | 0.509 | 268.1 | 9.5 |
| Lig$^{38}$TiBn$_2$ | 7 mg [10 μmol] | 500 | 1 | 73.9 | 0.739 | 268.1 | 19.5 | sistent with high-molecular weight polymer, which is not a poly(1-hexene) homopolymer. The total weight of resulting polymer was 2.54 g. (activity 254 g mmol$^{-1}$ h$^{-1}$). The physical appearance of this polymer was that of an elastomer. This is not characteristic of either of the homopolymers—polyethylene (solid thermoplastic material) or poly(1-hexene) (waxy oil). Thus, the microstructure of this polymer is consistent with that of a random copolymer of these two monomers having a high proportion of the higher monomer, 1-hexene. $^{13}$C NMR analysis at 130° C. in deuterated o-dichlorobenzene as solvent supported this notion. The spectrum was not a superposition of the spectra of the homopolymers, but was consistent with a random copolymer structure (Hsieh, E. T. et. al., *Macromolecules* 1982, 15, 1402). The relatively high proportion of the peak at 13.7 ppm, which corresponds to the methyl group of the 1-hexene repeat unit, relative to the peak at 29.7 ppm, which corresponds to a sequence of ethylene repeat units, supports the high incorporation of 1-hexene.

By changing the polymerization conditions: Toluene instead of heptane as solvent, and reducing the volume of employed 1-hexene to 2 mL, while keeping the other conditions without change, a copolymer weighing 1.2 grams was obtained having a less elastic appearance. $^{13}$C NMR analysis at 130° C. in deuterated o-dichlorobenzene as solvent showed the presence of the same peaks, but in a different proportion, the peak typical of 1-hexene repeat unit now being of lower proportion. As is clear to anyone skilled in the art, the further change of conditions like high-monomer concentration, the nature of solvent, the polymerization temperature and the ethylene pressure can produce co-polymers with a very broad range of physical properties and suitable for different applications. Other combinations of monomers can be copolymerized by Salalen-based catalytic systems by employing known procedures.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of polymerizing an alpha-olefin, the process comprising contacting the alpha-olefin with a catalyst system which comprises:
   (i) a pre-catalyst comprising a metal complex of a Group IV metal atom and a salalen ligand complexed therewith; and
   (ii) a co-catalyst,
   said metal complex having the general Formula II*:

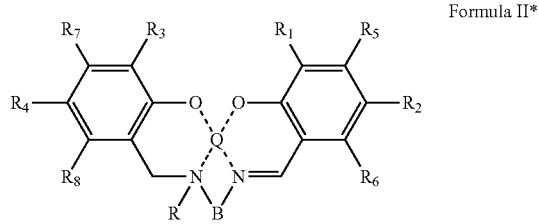

Formula II* wherein
Q is MXp,
whereas M is a group IV element; X is a labile group; and p is an integer ranging from 0 to 4;
B is a bridging moiety being at least 2 carbon atoms in length;
R is alkyl, cycloalkyl, aryl, heteroaryl and heteroalicyclic, or, alternatively, forms a 5-membered or 6-membered heterocyclic ring with a carbon atom of said bridging moiety; and
$R_1$-$R_8$ are each independently selected from the group consisting of hydrogen, alkyl, cycloalkyl, aryl, halogen, alkoxy, aryloxy, heteroalicyclic, heteroaryl, and nitro, provided that:
at least one of $R_1$-$R_4$ is independently a rigid bulky group selected from the group consisting of a cycloalkyl and a heteroalicyclic, each having at least 7 carbon atoms;
each of $R_1$-$R_4$ is independently a halogen; and/or
said R forms a 5-membered or 6-membered heterocyclic ring with a carbon atom of said bridging moiety,
thereby producing a polymer of the alpha-olefin.

2. The process of claim 1, wherein said alpha-olefin is propylene.

3. The process of claim 1, wherein said co-catalyst is an aluminoxane.

4. The process of claim 1, wherein said bridging moiety has a general Formula IVA or IVB:

   Formula IVA

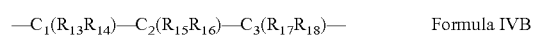   Formula IVB wherein $R_9$-$R_{14}$, $R_{17}$ and $R_{18}$ are each independently selected from the group consisting of hydrogen, alkyl, cycloalkyl, aryl, heteroaryl and heteroalicyclic,
$R_{15}$ and $R_{16}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively,
at least two of R and $R_9$-$R_{12}$ in Formula IVA or at least two of R and $R_{13}$-$R_{18}$ in Formula IVB form a 5-membered or 6-membered cyclic or heterocyclic ring.

5. The process of claim 1, wherein R is alkyl.

6. The process of claim 1, wherein at least one of $R_1$-$R_4$ is an alkyl.

7. The process of claim 6, wherein said alkyl is a bulky alkyl selected from the group consisting of tert-butyl, isobutyl, isopropyl, trityl, cumyl and tert-hexyl.

8. The process of claim 1, wherein at least one of $R_1$-$R_4$ is halogen.

9. The process of claim 8, wherein at least one of $R_3$ and $R_4$ is halogen.

10. The process of claim 1, wherein $R_1$ is adamantyl.

11. The process of claim 9, wherein $R_1$ is adamantyl.

12. A metal complex having the general formula II*:

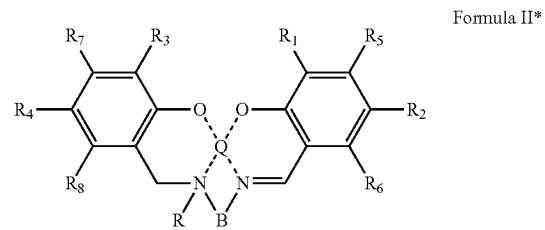

Formula II* wherein:

Q is MXp, whereas M is a group IV element; X is a labile group; and p is an integer ranging from 0 to 4;

B is a bridging moiety being at least 2 carbon atoms in length;

R is alkyl, cycloalkyl, aryl, heteroaryl and heteroalicyclic, or, alternatively, forms a 5-membered or 6-membered heterocyclic ring with a carbon atom of said bridging moiety; and $R_1$-$R_8$ are each independently selected from the group consisting of hydrogen, alkyl, cycloalkyl, aryl, halogen, alkoxy, aryloxy, heteroalicyclic, heteroaryl, and nitro, provided that:

(i) at least one of $R_1$-$R_4$ is independently a rigid bulky group selected from the group consisting of a cycloalkyl and a heteroalicyclic, each having at least 7 carbon atoms;

(ii) each of $R_1$-$R_4$ is independently a halogen; and/or (iii) said R forms a 5-membered or 6-membered heterocyclic ring with a carbon atom of said bridging moiety.

13. The complex of claim 12, wherein said bridging moiety has a general Formula IVA or IVB:

—$C_1(R_9R_{10})$—$C_2(R_{11}R_{12})$—  Formula IVA

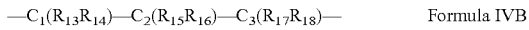
—$C_1(R_{13}R_{14})$—$C_2(R_{15}R_{16})$—$C_3(R_{17}R_{18})$—  Formula IVB wherein $R_9$-$R_{14}$, $R_{17}$ and $R_{18}$ are each independently selected from the group consisting of hydrogen, alkyl, cycloalkyl, aryl, heteroaryl and heteroalicyclic, $R_{15}$ and $R_{16}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of R and $R_9$-$R_{12}$ in Formula IVA or at least two of R and $R_{13}$-$R_{18}$ in Formula IVB form a 5-membered or 6-membered cyclic or heterocyclic ring.

14. The complex of claim 12, wherein R is alkyl.

15. The complex of claim 12, wherein at least one of $R_1$ and $R_3$ is said bulky rigid group.

16. The process of claim 4, wherein said bridging moiety has said general Formula IVA.

17. The process of claim 16, wherein each of $R_9$-$R_{12}$ is hydrogen.

18. The process of claim 16, wherein $R_9$ and R form said heterocyclic ring.

19. The process of claim 4, wherein said bridging moiety has said general Formula IVB.

20. The process of claim 19, wherein each of $R_{13}$-$R_{18}$ is hydrogen.

21. The process of claim 19, wherein at least two of $R_{13}$-$R_{18}$ form said cyclic ring.

22. The process of claim 1, wherein said co-catalyst is selected from the group consisting of an aluminoxane, a boron Lewis acid, a boron salt and any mixture thereof.

23. The complex of claim 13, wherein said bridging moiety has said general Formula IVA.

24. The complex of claim 23, wherein each of $R_9$-$R_{12}$ is hydrogen.

25. The complex of claim 23, wherein $R_9$ and R form said heterocyclic ring.

26. The complex of claim 13, wherein said bridging moiety has said general Formula IVB.

27. The complex of claim 26, wherein each of $R_{13}$-$R_{18}$ is hydrogen.

28. The complex of claim 26, wherein at least two of $R_{13}$-$R_{18}$ form said cyclic ring.

29. The complex of claim 12, wherein $R_1$ is adamantyl.

30. The complex of claim 29, wherein at least one of $R_3$ and $R_4$ is halogen.

31. A metal complex having the general formula II*:

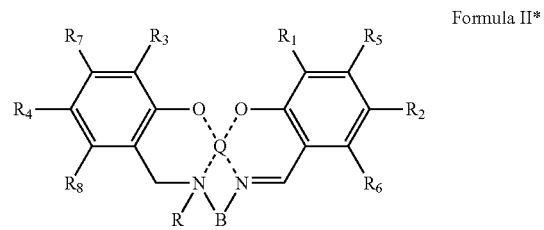

Formula II* wherein:

Q is MXp, whereas M is a group IV element; X is a labile group; and p is an integer ranging from 0 to 4;

B is a bridging moiety being at least 2 carbon atoms in length;

R is hydrogen, alkyl, cycloalkyl, aryl, heteroaryl and heteroalicyclic, or, alternatively, forms a 5-membered or 6-membered heterocyclic ring with a carbon atom of said bridging moiety; and $R_1$-$R_8$ are each independently selected from the group consisting of hydrogen, alkyl, cycloalkyl, aryl, halogen, alkoxy, aryloxy, heteroalicyclic, heteroaryl, and nitro, provided that:

(i) at least one of $R_1$-$R_4$ is independently a rigid bulky group selected from the group consisting of a cycloalkyl and a heteroalicyclic, each having at least 7 carbon atoms; and/or (ii) said bridging moiety in being at least 3 carbon atoms in length; and/or (iii) when said bridging moiety has 2 carbon atoms and has a general Formula IVA:

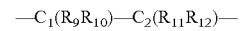
—$C_1(R_9R_{10})$—$C_2(R_{11}R_{12})$—  Formula IVA then each of $R_9$-$R_{12}$ is hydrogen.

32. The complex of claim 31, wherein said bridging moiety has a general Formula IVA or IVA:

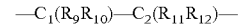
—$C_1(R_9R_{10})$—$C_2(R_{11}R_{12})$—  Formula IVA

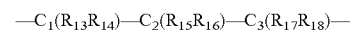
—$C_1(R_{13}R_{14})$—$C_2(R_{15}R_{16})$—$C_3(R_{17}R_{18})$—  Formula IVB wherein $R_9$-$R_{14}$, $R_{17}$ and $R_{18}$ are each independently selected from the group consisting of hydrogen, alkyl, cycloalkyl, aryl, heteroaryl and heteroalicyclic, $R_{15}$ and $R_{16}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of R and $R_9$-$R_{12}$ in Formula IVA or at least two of R and $R_{13}$-$R_{18}$ in Formula IVB form a 5-membered or 6-membered cyclic or heterocyclic ring.

33. The complex of claim 31, wherein at least one of $R_1$ and $R_3$ is said bulky rigid group.

34. The complex of claim 32, wherein said bridging moiety has said general Formula IVB.

35. The complex of claim 34, wherein each of $R_{13}$-$R_{18}$ is hydrogen.

36. The complex of claim 34, wherein at least two of $R_{13}$-$R_{18}$ form said cyclic ring.

37. The complex of claim 31, wherein $R_1$ is adamantyl.

38. The complex of claim 37, wherein at least one of $R_3$ and $R_4$ is halogen.

39. A process of polymerizing an alpha-olefin, the process comprising contacting the alpha-olefin with a catalyst system which comprises:
  (i) a pre-catalyst comprising the metal complex of claim 31; and
  (ii) a co-catalyst,
thereby producing a polymer of the alpha-olefin.

40. The process of claim 39, wherein said alpha-olefin is propylene.

41. The process of claim 39, wherein said co-catalyst is an aluminoxane.

* * * * *